US012691128B2

(12) United States Patent
Nezamis et al.

(10) Patent No.: US 12,691,128 B2
(45) Date of Patent: Jul. 28, 2026

(54) METHODS OF TREATING EOSINOPHILIC ESOPHAGITIS AND REDUCING CANDIDIASIS

(71) Applicant: Ellodi Pharmaceuticals, L.P., Blue Bell, PA (US)

(72) Inventors: James Nezamis, Blue Bell, PA (US); Gina Eagle, Blue Bell, PA (US); Mark Marino, Blue Bell, PA (US); Peter Richardson, Blue Bell, PA (US)

(73) Assignee: Ellodi Pharmaceuticals, L.P., Blue Bell, PA (US)

( * ) Notice: Subject to any disclaimer, the term of this patent is extended or adjusted under 35 U.S.C. 154(b) by 1052 days.

(21) Appl. No.: 17/765,068

(22) PCT Filed: Oct. 1, 2020

(86) PCT No.: PCT/US2020/053778
§ 371 (c)(1),
(2) Date: Mar. 30, 2022

(87) PCT Pub. No.: WO2021/067585
PCT Pub. Date: Apr. 8, 2021

(65) Prior Publication Data
US 2022/0347189 A1      Nov. 3, 2022

Related U.S. Application Data

(60) Provisional application No. 63/072,830, filed on Aug. 31, 2020, provisional application No. 62/908,697, filed on Oct. 1, 2019.

(51) Int. Cl.
*A61K 31/568*      (2006.01)
*A61K 9/00*      (2006.01)
*A61P 1/00*      (2006.01)

(52) U.S. Cl.
CPC ............ *A61K 31/568* (2013.01); *A61K 9/008* (2013.01); *A61P 1/00* (2018.01)

(58) Field of Classification Search
CPC ...... A61K 31/568; A61K 9/008; A61K 31/58; A61K 45/06; A61K 31/56; A61K 31/573; A61P 1/00; A61P 1/04; A61P 37/02
(Continued)

(56) References Cited

U.S. PATENT DOCUMENTS

| | | | |
|---|---|---|---|
| 3,705,172 A | 12/1972 | Buchel et al. | |
| 3,929,768 A | 12/1975 | Brattsand et al. | |

(Continued)

FOREIGN PATENT DOCUMENTS

| | | |
|---|---|---|
| CA | 1027864 A | 3/1978 |
| CA | 2430481 A1 | 6/2002 |

(Continued)

OTHER PUBLICATIONS

Gentile et al., "Oesophageal narrowing is common and frequently under-appreciated at endoscopy in patients with oesophageal eosinophilia". Alimentary Pharmacology & Therapeutics (Dec. 2014); 40(11-12): 1333-1340. Epub Oct. 7, 2014.

(Continued)

*Primary Examiner* — Taylor V Oh
(74) *Attorney, Agent, or Firm* — COOLEY LLP

(57) ABSTRACT

Disclosed herein are methods for treating eosinophilic oesophagitis with corticosteroids. The methods for treating eosinophilic oesophagitis disclosed herein result in reduced corticosteroid side effects, e.g. candidiasis. Dosages, formulations, and methods for administration of corticosteroids are provided.

32 Claims, 9 Drawing Sheets

(58) Field of Classification Search

USPC .......................................................... 514/182

See application file for complete search history.

(56) References Cited

U.S. PATENT DOCUMENTS

| | | | |
|---|---|---|---|
| 4,080,448 | A | 3/1978 | Mirsky |
| 4,335,121 | A | 6/1982 | Phillipps et al. |
| 4,363,806 | A | 12/1982 | Bergstrom et al. |
| 4,472,393 | A | 9/1984 | Shapiro |
| 4,985,418 | A | 1/1991 | Richards |
| 5,135,740 | A | 8/1992 | Katz et al. |
| 5,252,337 | A | 10/1993 | Powell |
| 5,278,175 | A | 1/1994 | Ray et al. |
| 5,403,893 | A | 4/1995 | Tanaka et al. |
| 5,446,070 | A | 8/1995 | Mantelle |
| 5,482,934 | A | 1/1996 | Calatayud et al. |
| 5,639,475 | A | 6/1997 | Bettman et al. |
| 5,776,433 | A | 7/1998 | Tzou et al. |
| 5,863,910 | A | 1/1999 | Bolonick et al. |
| 6,139,865 | A | 10/2000 | Friend et al. |
| 6,171,617 | B1 | 1/2001 | Gruber |
| 6,316,027 | B1 | 11/2001 | Johnson et al. |
| 6,495,160 | B2 | 12/2002 | Esposito et al. |
| 6,534,549 | B1 | 3/2003 | Newton et al. |
| 6,596,298 | B2 | 7/2003 | Leung et al. |
| 6,596,311 | B1 | 7/2003 | Dobetti |
| 6,740,332 | B2 | 5/2004 | Zyck et al. |
| 7,033,606 | B1 | 4/2006 | Besse et al. |
| 7,122,198 | B1 | 10/2006 | Singh et al. |
| 7,125,564 | B2 | 10/2006 | Chen et al. |
| 7,229,641 | B2 | 6/2007 | Cherukuri |
| 7,384,921 | B2 | 6/2008 | Tang et al. |
| 8,077,288 | B2 | 12/2011 | Kawashima |
| 8,324,192 | B2 | 12/2012 | Dohil et al. |
| 8,545,881 | B2 | 10/2013 | Venkatesh et al. |
| 8,580,300 | B2 | 11/2013 | Wilhelm et al. |
| 8,679,545 | B2 | 3/2014 | Dohil et al. |
| 8,771,729 | B2 | 7/2014 | Perrett et al. |
| 8,932,596 | B2 | 1/2015 | Benhamou et al. |
| 9,387,167 | B2 | 7/2016 | Perrett et al. |
| 9,486,407 | B2 | 11/2016 | Perrett et al. |
| 9,782,347 | B2 | 10/2017 | Dohil et al. |
| 9,849,084 | B2 | 12/2017 | Perrett et al. |
| 9,867,780 | B2 | 1/2018 | Greinwald et al. |
| 10,076,494 | B2 | 9/2018 | Pevzner et al. |
| 10,105,315 | B2 | 10/2018 | Meltzer et al. |
| 10,176,301 | B2 | 1/2019 | Hill et al. |
| 10,272,037 | B2 | 4/2019 | Dohil et al. |
| 10,471,071 | B2 | 11/2019 | Gosselin et al. |
| 10,632,069 | B2 | 4/2020 | Perrett et al. |
| 10,869,592 | B2 | 12/2020 | Ouyang et al. |
| 11,026,887 | B2 | 6/2021 | Meltzer et al. |
| 11,166,961 | B2 | 11/2021 | Gosselin et al. |
| 11,246,828 | B2 | 2/2022 | Perrett et al. |
| 11,260,061 | B2 | 3/2022 | Gosselin et al. |
| 11,266,598 | B2 | 3/2022 | Perrett et al. |
| 11,684,571 | B2 | 6/2023 | Meltzer et al. |
| 11,896,710 | B2 | 2/2024 | Meltzer et al. |
| 12,059,494 | B2 | 8/2024 | Meltzer et al. |
| 12,290,598 | B2 | 5/2025 | Perrett et al. |
| 12,310,976 | B2 | 5/2025 | Gosselin et al. |
| 12,447,157 | B2 | 10/2025 | Gosselin et al. |
| 2001/0006625 | A1 | 7/2001 | Bohn et al. |
| 2001/0014340 | A1 | 8/2001 | Ohta et al. |
| 2003/0050312 | A1 | 3/2003 | Hjorth et al. |
| 2003/0054036 | A1 | 3/2003 | Liggins et al. |
| 2003/0099701 | A1 | 5/2003 | Takaishi et al. |
| 2003/0124184 | A1 | 7/2003 | Mezaache et al. |
| 2003/0215500 | A1 | 11/2003 | Ohta et al. |
| 2004/0009212 | A1 | 1/2004 | Tsai |
| 2004/0053902 | A1 | 3/2004 | Smith |
| 2004/0106663 | A1 | 6/2004 | Talley et al. |
| 2004/0228919 | A1 | 11/2004 | Houghton et al. |
| 2004/0265375 | A1 | 12/2004 | Platteeuw et al. |
| 2005/0009848 | A1 | 1/2005 | Brantl |
| 2005/0019393 | A1 | 1/2005 | Augsburger et al. |
| 2005/0112188 | A1 | 5/2005 | Eliaz et al. |
| 2005/0232988 | A1 | 10/2005 | Venkatesh et al. |
| 2006/0051414 | A1 | 3/2006 | Ramalho et al. |
| 2006/0105038 | A1 | 5/2006 | Lai et al. |
| 2006/0134054 | A1 | 6/2006 | Kulkarni et al. |
| 2006/0292099 | A1 | 12/2006 | Milburn et al. |
| 2007/0020330 | A1 | 1/2007 | Dang et al. |
| 2007/0059361 | A1 | 3/2007 | Rawas-Qalaji et al. |
| 2007/0111978 | A1 | 5/2007 | Dohil et al. |
| 2008/0132535 | A1 | 6/2008 | Singh et al. |
| 2009/0022799 | A1 | 1/2009 | Barman |
| 2009/0074862 | A1 | 3/2009 | Schioppi et al. |
| 2009/0123390 | A1 | 5/2009 | Hill |
| 2009/0123550 | A1 | 5/2009 | Phillips et al. |
| 2009/0123551 | A1 | 5/2009 | Phillips et al. |
| 2009/0131386 | A1 | 5/2009 | Phillips |
| 2009/0149433 | A1 | 6/2009 | Phillips |
| 2009/0155360 | A1 | 6/2009 | Venkatesh et al. |
| 2009/0169620 | A1 | 7/2009 | Venkatesh et al. |
| 2009/0181099 | A1 | 7/2009 | Dohil et al. |
| 2009/0191275 | A1 | 7/2009 | Dohil et al. |
| 2009/0264392 | A1 | 10/2009 | Warndahl et al. |
| 2010/0034894 | A1 | 2/2010 | Szymczak et al. |
| 2010/0215753 | A1 | 8/2010 | Sherwood et al. |
| 2010/0216754 | A1 | 8/2010 | Hill |
| 2011/0081411 | A1 | 4/2011 | Perrett et al. |
| 2011/0097401 | A1 | 4/2011 | Phillips et al. |
| 2011/0123460 | A1 | 5/2011 | Wilhelm et al. |
| 2011/0129530 | A1 | 6/2011 | Venkatesh et al. |
| 2011/0189299 | A1 | 8/2011 | Okubo et al. |
| 2012/0128764 | A1 | 5/2012 | Venkatesh et al. |
| 2012/0164080 | A1 | 6/2012 | Hill et al. |
| 2012/0282335 | A1 | 11/2012 | Venkatesh et al. |
| 2013/0296286 | A1 | 11/2013 | Dohil et al. |
| 2013/0310661 | A1 | 11/2013 | Jedwab et al. |
| 2014/0187523 | A1 | 7/2014 | Dohil et al. |
| 2014/0228714 | A1 | 8/2014 | Chau et al. |
| 2014/0287051 | A1 | 9/2014 | Perrett et al. |
| 2014/0303131 | A1 | 10/2014 | Perrett et al. |
| 2014/0328861 | A1 | 11/2014 | Payton et al. |
| 2015/0209432 | A1 | 7/2015 | Konda et al. |
| 2015/0231156 | A1 | 8/2015 | Phillips et al. |
| 2016/0045518 | A1 | 2/2016 | Dohil et al. |
| 2016/0078186 | A1 | 3/2016 | Hill et al. |
| 2016/0206627 | A1 | 7/2016 | Gosselin et al. |
| 2016/0213681 | A1 | 7/2016 | Santus et al. |
| 2016/0324772 | A1 | 11/2016 | Greinwald et al. |
| 2017/0071855 | A1 | 3/2017 | Perrett et al. |
| 2017/0183719 | A1 | 6/2017 | Rothenberg et al. |
| 2018/0071211 | A1 | 3/2018 | Dohil et al. |
| 2018/0133145 | A1 | 5/2018 | Meltzer et al. |
| 2018/0153802 | A1 | 6/2018 | Perrett et al. |
| 2019/0008760 | A1 | 1/2019 | Meltzer et al. |
| 2019/0201333 | A1 | 7/2019 | Dohil et al. |
| 2020/0016171 | A1 | 1/2020 | Gosselin et al. |
| 2020/0214979 | A1 | 7/2020 | Perrett et al. |
| 2020/0368147 | A1 | 11/2020 | Meltzer et al. |
| 2020/0381097 | A1 | 12/2020 | Meltzer |
| 2021/0205328 | A1 | 7/2021 | Gosselin et al. |
| 2021/0244660 | A1 | 8/2021 | Perrett et al. |
| 2021/0275438 | A1 | 9/2021 | Meltzer et al. |
| 2021/0346278 | A1 | 11/2021 | Meltzer et al. |
| 2022/0110945 | A1 | 4/2022 | Gosselin et al. |
| 2022/0339098 | A1 | 10/2022 | Perrett |
| 2023/0414498 | A1 | 12/2023 | Meltzer et al. |
| 2024/0207288 | A1 | 6/2024 | Eagle |
| 2025/0170057 | A1 | 5/2025 | Meltzer et al. |
| 2025/0255884 | A1 | 8/2025 | Gosselin et al. |
| 2025/0322925 | A1 | 10/2025 | Meltzer |

FOREIGN PATENT DOCUMENTS

| CA | 2704946 | A1 | 5/2009 |
|---|---|---|---|
| CA | 2776164 | A1 | 4/2011 |
| CL | 38272008 | | 12/2007 |
| CN | 1186428 | A | 7/1998 |
| CN | 102348407 | A | 2/2012 |
| CN | 102665722 | A | 9/2012 |

(56) References Cited

FOREIGN PATENT DOCUMENTS

| | | | |
|---|---|---|---|
| CN | 105392497 | A | 3/2016 |
| DE | 2323215 | A1 | 11/1973 |
| DE | 4129535 | A1 | 3/1992 |
| DE | 60202794 | T2 | 5/2006 |
| DE | 202010018594 | U1 | 2/2018 |
| EP | 0057401 | A1 | 8/1982 |
| EP | 0440372 | A1 | 8/1991 |
| EP | 1310243 | A1 | 5/2003 |
| EP | 1323417 | A1 | 7/2003 |
| EP | 1595533 | A1 | 11/2005 |
| EP | 2886108 | A1 | 6/2015 |
| EP | 2211896 | B1 | 1/2018 |
| EP | 2482822 | B1 | 8/2018 |
| EP | 2214679 | B1 | 3/2019 |
| EP | 3041476 | B1 | 11/2019 |
| EP | 3354276 | B1 | 1/2020 |
| JP | S56138200 | A | 10/1981 |
| JP | 11130679 | A | 5/1999 |
| JP | H11511162 | A | 9/1999 |
| JP | 2001524094 | A | 11/2001 |
| JP | 2002521321 | A | 7/2002 |
| JP | 2003509359 | A | 3/2003 |
| JP | 2003261439 | A | 9/2003 |
| JP | 2003292459 | A | 10/2003 |
| JP | 2006077018 | A | 3/2006 |
| JP | 2006516616 | A | 7/2006 |
| JP | 2006516646 | A | 7/2006 |
| JP | 2006524650 | A | 11/2006 |
| JP | 2009519793 | A | 5/2009 |
| JP | 2009521523 | A | 6/2009 |
| JP | 2009173552 | A | 8/2009 |
| JP | 2011503073 | A | 1/2011 |
| JP | 2013506683 | A | 2/2013 |
| KR | 20060123160 | A | 12/2006 |
| KR | 20100087007 | A | 8/2010 |
| KR | 20120104975 | A | 9/2012 |
| KR | 20160058829 | A | 5/2016 |
| RU | 2011134040 | A | 2/2013 |
| RU | 2016104400 | A | 8/2017 |
| TW | 201808304 | A | 3/2018 |
| WO | WO-9632095 | A1 | 10/1996 |
| WO | WO-9706786 | A1 | 2/1997 |
| WO | WO-9847535 | A1 | 10/1998 |
| WO | WO-9947144 | A1 | 9/1999 |
| WO | WO-0044351 | A1 | 8/2000 |
| WO | WO-0064450 | A1 | 11/2000 |
| WO | WO-0119342 | A2 | 3/2001 |
| WO | WO-2002015884 | A2 | 2/2002 |
| WO | WO-02092057 | A1 | 11/2002 |
| WO | WO-03039520 | A1 | 5/2003 |
| WO | WO-03074029 | A1 | 9/2003 |
| WO | WO-03093344 | A1 | 11/2003 |
| WO | WO-2004064810 | A1 | 8/2004 |
| WO | WO-2004067004 | A1 | 8/2004 |
| WO | WO-2004069225 | A1 | 8/2004 |
| WO | WO-2004091585 | A1 | 10/2004 |
| WO | WO-2005087194 | A1 | 9/2005 |
| WO | WO-2007071179 | A1 | 6/2007 |
| WO | WO-2007074472 | A2 | 7/2007 |
| WO | WO-2008098634 | A1 | 8/2008 |
| WO | WO-2009006516 | A1 | 1/2009 |
| WO | WO-2009064457 | A2 | 5/2009 |
| WO | WO-2009064458 | A2 | 5/2009 |
| WO | WO-2009064819 | A2 | 5/2009 |
| WO | WO-2009078872 | A1 | 6/2009 |
| WO | WO-2009086046 | A1 | 7/2009 |
| WO | WO-2009098595 | A2 | 8/2009 |
| WO | WO-2010021636 | A1 | 2/2010 |
| WO | WO-2010082986 | A1 | 7/2010 |
| WO | WO-2010127345 | A2 | 11/2010 |
| WO | WO-2010127346 | A1 | 11/2010 |
| WO | WO-2010144865 | A2 | 12/2010 |
| WO | WO-2011041509 | A1 | 4/2011 |
| WO | WO-2015006571 | A1 | 1/2015 |
| WO | WO-2015034678 | A2 | 3/2015 |
| WO | WO-2015035114 | A1 | 3/2015 |
| WO | WO-2017189805 | A1 | 11/2017 |
| WO | WO-2018035393 | A1 | 2/2018 |
| WO | WO-2019165138 | A1 | 8/2019 |
| WO | WO-2021067585 | A1 | 4/2021 |
| WO | WO-2022020464 | A1 | 1/2022 |
| WO | WO-2022225892 | A1 | 10/2022 |
| ZA | 6805392 | | 6/1969 |

OTHER PUBLICATIONS

German Patent Complaint Proceedings in the Regional Court, Mannheim, *Ellodi Pharmaceuticals, L.P.* vs. *Dr. Falk Pharma GmbH*, Docket No. 7 O 75/19, communication from the Regional Court of Mannheim giving Dr. Falk Pharma GmbH the opportunity to comment on the withdrawal of the complaint, dated Jul. 12, 2022, and Machine English translation, 2 pages.

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Notice of termination of proceedings dated Aug. 16, 2022, and English translation, 2 pages.

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Withdrawal of cancellation action dated Jul. 20, 2022, 1 page.

Opposition Proceedings in European Patent No. EP 2482822, Appeal No. T1954/21-3.3.01 (Appln. No. 10821232.5), filed by Dr. Falk Pharma GmbH on Mar. 1, 2019; EPO Communication dated Jul. 25, 2022 regarding Termination of opposition proceedings, 1 page.

Opposition Proceedings in European Patent No. EP 3086782 (Appln. No. 14814872.9), (in the name of Dr. Falk Pharma GmbH) filed by Ellodi Pharmaceuticals, L.P. on Jun. 26, 2019; Written decision on rejection of the opposition dated May 9, 2022, and English translation, 63 pages.

Opposition Proceedings in European Patent No. EP 3403654 (Appln. No. 18178891.0), filed by Dr. Falk Pharma GmbH; Decision to discontinue the opposition proceedings dated Sep. 5, 2022, 2 pages.

PCT/US2022/025297, International Search Report and Written Opinion mailed Jul. 29, 2022, 10 pages.

Takita et al., "Successful esophageal endoscopic submucosal dissection with a transoral endoscope after stepwise scope bougienage of post-endoscopic submucosal dissection stricture". JGH Open (Oct. 22, 2020); 5(1): 163-165. eCollection Jan. 2021.

Aceves, et al., "Oral viscous budesonide: a potential new therapy for eosinophilic esophagitis in children". Am J Gastroenterol. (Oct. 2007); 102(10): 1-9. Epub Jun. 20, 2007.

Aceves, et al., "Topical viscous budesonide suspension for treatment of eosinophilic esophagitis". The Journal of Allergy and Clinical Immunology (Sep. 1, 2005); vol. 116, Issue 3, pp. 705-706. Epub Jul. 1, 2005.

Ahmed and Shah, "Formulation of low dose medicines—theory and practice." Am. Pharm. Rev (2000); 3(3): 9-14.

Ahmed, Monjur, "Eosinophilic esophagitis in adults: An update". World J Gastrointest Pharmacol Ther. (May 6, 2016); 7(2): 207-213.

Alexander, et al., "Review. Therapeutic Options for Eosinophilic Esophagitis". Gastroenterology & Hepatology (Jan. 1, 2011.); 7(1): 59-61.

Auszug von European Pharmacopeia 6.0 (English language) 2.9.8; Jul. 23, 2007, 2 pages.

Auszug von European Pharmacopeia 8.0 (German language) 2.9.8; Jul. 15, 2013, 1 page.

Auszug von US Pharmacopeia 35 1217; May 1, 2012, 3 pages.

[Author Unknown] Definition of slow-release (downloaded from Merriam-Webster online athttps://www.merriam-webster.com/medical/slow-release); accessed Jul. 31, 2019, 1 page.

[Author Unknown] Definition of sustained-release (downloaded from Merriam-Webster online athttps://www.merriam-webster.com/dictionary/sustainedrelease#medicalDictionary); accessed Jul. 31, 2019, 1 page.

(56) References Cited

OTHER PUBLICATIONS

[Author unknown] DrugBank Accession Number, first approved 1990, DrugBank Accession No. DB00588, https://go.drugbank.com/drugs/DB00588, 14 pages.

[Author Unknown] Jorveza package leaflet (downloaded from the European Medicines Agency atwww.ema.europa.eu/en/medicines/human/EPAR/jorveza#product-informationsection); accessed Aug. 1, 2019, 8 pages.

[Author Unknown] Jorveza package leaflet, Jorveza 1mg orodispersible tablets, tablets package leaflet (PIL) for United Kingdom-Ireland, Mat-No. 1147370 (Losan Pharma), Dated Mar. 15, 2018, Date Code Falk: GB-IE/03.18, 2 pages.

[Author Unknown] Jorveza summary of product characteristics (downloaded from the European Medicines Agency atwww.ema. europa.eu/en/medicines/human/EPAR/jorveza#product-informationsection); first published Jan. 18, 2018, accessed Aug. 1, 2019, 9 pages.

[Author Unknown] Povidone (polyvinylpyrrolidone (PVP)) compound summary (downloaded from Wikipedia at https://en.wikipedia.org/wiki/Polyvinylpyrrolidone); accessed Jul. 31, 2019, 5 pages.

[Author Unknown] Solubility of budesonide (downloaded fromhttps://pubchem.ncbi.nlm.nih.gov/compound/Budesonide#section=Solubility&fullsc reen=true); information available as of Oct. 15, 2015, accessed Aug. 1, 2019, 1 page.

Author Unknown, WHT 3ME brochure Version 2.0; Fully Automated 4 in 1 Tablet Testing Instrument Pharma Test; publication date unknown.

Bauer, et al., "106 Chapter 5 Methods and Basic Operations". Lehrbuch der Pharmazeutischen Technologie (Textbook of pharmaceutical technology), With an introduction to biopharmacy (2006); (eds) LIPPOLD, et al., 8th revised and updated edition, and English translation, 12 pages.

Beveridge, et al., "Novel Therapeutic Approaches to Eosinophilic Esophagitis". Gastroenterology & Hematology (Jun. 2020); 16(6): 294-301.

Bonnet, et al., "Formulation of a 3-months Stability Oral Viscous Budesonide Gel and Development of an Indicating Stability HPLC Method", Pharm Technol Hosp Pharm (2018); 3(2): 91-99.

Bower et al., "Manifestations and Treatment of Laryngeal Sarcoidosis". Am. Rev. Respir. Dis., 122(2): 325-332 (1980).

Breuer, et al., "Glossary of Terms Related to Pharmaceutics (IUPAC Recommendations 2009)" Pure Appl. Chem. (2009); 81 (5): 971-999.

Brunner, et al., "Gastrointestinal transit, release and plasma pharmacokinetics of a new oral budesonide formulation." British Journal of Clinical Pharmacology (2005); 61(1): 31-38.

Buckton, G., "Water sorption and near IR spectroscopy to study the differences between microcrystalline cellulose and silicified microcrystalline cellulose before and after wet granulation." International Journal of Pharmaceutics (Apr. 1999); 181 (1): 41-47.

Budesonid, https://www.chemie.de/lexikon/Budesonid.html, Jul. 12, 2019, and English version, Sep. 10, 2020, 3 pages.

Campieria et al., "Oral budesonide is as effective as oral prednisolone in active Crohn's disease," Gut, 41: 209-214 (1997).

Certified Priority Document U.S. Appl. No. 61/186,777, filed Jun. 12, 2009, 104 pages.

Daley-Yates, Peter T. "Inhaled corticosteroids: potency, dose equivalence and therapeutic index." British Journal of Clinical Pharmacology (2015); 80(3): 372-380.

Declaration of Stephen Perrett, MBA, Ph.D. dated Jul. 16, 2020, 6 pages.

Dellon, et al., "Efficacy of Budesonide vs Fluticasone for Initial Treatment of Eosinophilic Esophagitis in a Randomized Controlled Trial". Gastroenterology (2019); 157: 65-73.

Dilger, K., et al. "Active eosinophilic esophagitis is associated with impaired elimination of budesonide by cytochrome P450 3A enzymes." Digestion (2013); 87(2):110-117. Epub Jan. 25, 2013.

Dohil, et al., "Oral Viscous Budesonide Is Effective in Children With Eosinophilic Esophagitis in a Randomized, Placebo-Controlled Trial". Gastroenterol. (Aug. 2010); 139(2): 418-429.

Dolo-Dobendan®, 1.4 mg/10 mg lozenges package insert, Reference ID 3030657, Revised: Jan. 2015, with English translation, 7 pages.

Dr. Schleuniger, "Key factors influencing measured tablet hardness"; Pharmatron; 2011, 5 pages.

EPO Communication dated Apr. 25, 2019 in connection with Application No. EP 08848597.4, 13 pages.

Eurasian Application No. 201491358, Search Report (with English translation), issued Jan. 22, 2015, 4 pages.

European Application No. EP 19757814.9, Extended European Search Report dated Nov. 4, 2021, 11 pages.

European Application No. EP 10821232.5, Extended European Search Report dated Feb. 6, 2014, 10 pages.

European Application No. EP 14184844.0, Extended European Search Report dated Feb. 9, 2015, 7 pages.

European Application No. EP 14842811.3, Extended European Search Report dated Mar. 23, 2017, 6 pages.

European Application No. EP 17842162.4, Extended European Search Report dated Apr. 1, 2020, 8 pages.

European Application No. EP 18178891.0, Extended European Search Report dated Aug. 13, 2018, 3 pages.

European Application No. EP 19189185.2, Extended European Search Report dated Aug. 29, 2019, 9 pages.

European Application No. EP 19207287.4, Extended European Search Report dated Apr. 6, 2020, 9 pages.

Falcoz, et al., "Bioavailability of Orally Administered Micronised Fluticasone Propionate." Clinical Pharmacokinetics (2000); 39 Suppl. 1: 9-15.

Forum of the National Formulary of Japan, compilation, Drugs in Japan, 2009 edition, published 2008, p. 2161-2165 (and English translation/summary of pertinent paragraphs), 8 pages.

Furuta, et al., "Review article: the pathogenesis and management of eosinophilic oesophagitis". Alimentary Pharmacology & Therapeutics (2006); 24: 172-182.

Furuta, Glenn T., "Eosinophils in the Esophagus: Acid is Not the Only Cause". Journal of Pediatric Gastroenterology & Nutrition (Apr. 1998); 26(4): 468-471.

Furuta, Glenn T., et al. "Eosinophilic esophagitis in children and adults: a systematic review and consensus recommendations for diagnosis and treatment: sponsored by the American Gastroenterological Association (AGA) Institute and North American Society of Pediatric Gastroenterology, Hepatology, and Nutrition." Gastroenterology (2007); 133(4): 1342-1363.

Georgia Application No. AP 2010012674, Search Report (with English translation) dated Nov. 28, 2013, 11 pages.

German Patent Complaint Proceedings in the Regional Court, Mannheim, *Ellodi Pharmaceuticals, L.P.* (formerly Adare Development I, L.P.) vs. *Dr. Falk Pharma GmbH*, Docket No. 7 O 75/19, Defendant's Consent to Withdrawal filed Jul. 15, 2022, and English translation, 2 pages.

German Patent Complaint Proceedings in the Regional Court, Mannheim, *Ellodi Pharmaceuticals, L.P.* vs. *Dr. Falk Pharma GmbH*, Docket No. 7 O 75/19, Order concerning value under dispute dated Jul. 18, 2022, and English translation, 4 pages.

German Patent Complaint Proceedings in the Regional Court, Mannheim, *Ellodi Pharmaceuticals, L.P.* vs. *Dr. Falk Pharma GmbH*, Docket No. 7 O 75/19, Withdrawal Submission filed by Ellodi Pharmaceuticals, L.P., dated Jul. 11, 2022, and English translation, 2 pages.

German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 12, 2020, and English translation, 5 pages.

German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 13, 2020, and English translation, 3 pages.

German Patent Complaint Proceedings in the Regional Court, Mannheim, Germany, *Adare Development I, L.P.* vs. *Dr. Falk Pharma GmbH*, Docket No. 7 O 75/19, Pleadings as filed, dated Dec. 16, 2019, and English translation, 66 pages.

German Patent Complaint Proceedings in the Regional Court, Mannheim, Germany, *Adare Development I, L.P.* vs. *Dr. Falk*

(56)                    References Cited

OTHER PUBLICATIONS

*Pharma GmbH*, Docket No. 7 O 75/19, Response to Rejoinder as filed, dated Feb. 6, 2020 (and English translation), 36 pages.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk—rejoinder dated Jan. 30, 2020 (and English translation), 38 pages.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk—statement of defense, filed Oct. 7, 2019 (and English translation), 14 pages.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk dated Feb. 10, 2020, 6 pages, in German and English.
German Patent Complaint Proceedings in the Regional Court, Mannheim, Germany, *Adare Development I, L.P.* vs. *Dr. Falk Pharma GmbH*, Docket No. 7 O 75/19, Writ as filed, dated Feb. 11, 2020, and English translation, 5 pages.
German Patent Infringement Proceedings in the Regional Court, Mannheim, Germany, *Adare Development I, L.P.* vs. *Dr. Falk Pharma GmbH*, Docket No. 7 O 75/19, Patent Complaint dated Jul. 3, 2019, with English translation, 107 pages.
German Utility Model Cancellation Action, Request for Cancellation, filed by Dr. Falk Pharma GmbH on Mar. 1, 2019 with the German Patent Office, in connection with DE Patent No. 202010018594 U1 in the name of Adare Pharmaceuticals, Inc., and English translation, 21 pages.
German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Statement of Grounds of Appeal dated Feb. 26, 2021 (and English translation), and Exhibit B817—Current EPA register extract on D5 dated Nov. 27, 2020, 117 pages.
German Utility Model Cancellation Proceedings, *Dr. Falk Pharma GmbH* (Plaintiff) vs. *Adare Development I, L.P.* (Patentee), Utility model DE 20201 018594 U1, Adare—Further Submission as filed dated Jul. 12, 2019, and English translation, 56 pages.d
German Utility Model Cancellation Proceedings, *Dr. Falk Pharma GmbH* (Plaintiff) vs. *Adare Development I, L.P.* (Patentee), Utility model DE 20201 018594 U1, Auxiliary Request I-IV (marked-up) dated and as filed Jul. 1, 2020, and English translation, 17 pages.
German Utility Model Cancellation Proceedings, *Dr. Falk Pharma GmbH* (Plaintiff) vs. *Adare Development I, L.P.* (Patentee), Utility model DE 20201 018594 U1, Official Communication—Interlocutory Notice dated Jan. 22, 2020 (and English translation), 12 pages.
German Utility Model Cancellation Proceedings, *Dr. Falk Pharma GmbH* (Plaintiff) vs. *Adare Development I, L.P.* (Patentee), Utility model DE 20201 018594 U1, Response to Dr. Falk and Summons dated Jul. 2, 2020, and English translation, 18 pages.
German Utility Model Cancellation Proceedings, *Dr. Falk Pharma GmbH* (Plaintiff) vs. *Adare Development I, L.P.* (Patentee), Utility model DE 20201 018594 U1, Response to Pleadings as filed dated Oct. 17, 2019, and English translation, 25 pages.
German Utility Model Cancellation Proceedings, *Dr. Falk Pharma GmbH* (Plaintiff) vs. *Adare Development I, L.P.* (Patentee), Utility model DE 20201 018594 U1, Submission of Dr. Falk - Pleadings dated Sep. 13, 2019 (and English translation), 27 pages.
German Utility Model Cancellation Proceedings, *Dr. Falk Pharma GmbH* (Plaintiff) vs. *Adare Development I, L.P.* (Patentee), Utility model DE 202010018594 U1, Adare's Response dated Apr. 6, 2020 to Interlocutory Decision, and English translation, 29 pages.
German Utility Model Cancellation Proceedings, *Dr. Falk Pharma GmbH* (Plaintiff) vs. *Adare Development I, L.P.* (Patentee), Utility model DE 202010018594 U1, Communication from Adare to German Patent Office, Auxiliary Requests 1 and 2 (clean, marked-up and English translations) as filed Apr. 6, 2020, 23 pages.

German Utility Model Cancellation Proceedings, *Dr. Falk Pharma GmbH* (Plaintiff) vs. *Adare Development I, L.P.* (Patentee), Utility model DE 202010018594 U1, Submission of Dr. Falk—response to Adare and summons, dated Jul. 8, 2020 (and English translation), 11 pages.
German Utility Model Cancellation Proceedings, *Dr. Falk Pharma GmbH* (Plaintiff) vs. *Adare Development I, L.P.* (Patentee), Utility model DE 202010018594 U1, submission/Response by Dr. Falk Pharma GmbH dated Apr. 8, 2020 (and English translation), 18 pages.
Hahm and Augsburger, Orally Disintegrating Tablets and Related Tablet Formulations, Pharmaceutical Dosage Forms: Tablets, Third Edition, Ch. 9, vol. 2, Herausgeber: (eds) Larry L. Augsburger, Stephen W. Hoag, CRC Press (2008), 21 pages.
Ham, et al., "Quantitation of esophagal transit by means of 81mKr." European Journal of Nuclear Medicine (1984); 9: 362-365.
Handbook of Pharmaceutical Excipients (2009); Sixth Edition, ISBN 978 1 58212 135 2, (eds.) Rowe, et al., Cover Page, Print/Copyright and Preface Pages, 4 pages.
International Preliminary Report on Patentability for International Application No. PCT/US2017/047474, dated Feb. 19, 2019, 8 pages.
International Search Report and Written Opinion for International Application No. PCT/US2017/047474, mailed Dec. 26, 2017,11 pages.
Jorveza (budesonide) Update by the Committee for Medicinal Products for Human Use (CHMP), Summary of opinion1 (post authorisation) dated Mar. 26, 2020, European Medicines Agency, 1 page.
Katdare and Chaubal (eds)., Excipient Development for Pharmaceutical, Biotechnology and Drug Delivery Systems, Herausg. CRC Press, Taylor & Francis Group, Boca Raton, USA, 2006; dart: Excipients for Oral Liquid Formulations, S. 155-180, 28 pages.
Khan and Orenstein, "Eosinophilic Gastroenteritis: Epidemiology, Diagnosis and Management." Paediatr Drugs. (2002); 4(9): 563-570.
Koukourakis, et al., "Oral Administration of Recombinant Human Granulocyte Macrophage Colony-stimulating Factor in the Management of Radiotherapy-induced Esophagitis", Clinical Cancer Research (Dec. 1999); 5(12): 3970-3976.
Krishna, et al., "Treatment of Eosinophilic Esophagitis Is Oral Viscous Budesonide Superior to Swallowed Fluticasone Spray?" Gastroenterol Hepatol (Jan. 2011); 7(1): 55-59.
Kumari and Rajendran, "Effect of topical nasal steroid spray in the treatment of non-specific recurrent/chronic pharyngitis-a trial study." Indian Journal of Otolaryngology and Head & Neck Surgery, 60(3): 199-201 (2008).
Langdon, BA and Mullamey, (2006) Handbook of Pharmaceutical Excipients. (eds.) Rowe, R.C., Sheskey, PJ and Owen, S.C., London: Pharmaceutical Press and American Pharmacists Association (extract—pp. 53-55 and 742-743), 14 pages.
Lee, Geoffrey, Professor, Report of Professor Geoffrey Lee, Ph.D. on measurement of disintegration time of "Jorveza 1 mg orodispersible tablet" dated Nov. 15, 2019, 16 pages.
Li, Xiaowei, et al., "Advances in Injectable Thermosensitive Polymers". Polymer Bulletin, No. 3, pp. 109-115, Jun. 30, 2015 (with English Abstract), 7 pages.
Liacouras, et al., "Primary Eosinophilic Esophagitis in Children: Successful Treatment with Oral Corticosteroids". Journal of Pediatric Gastroenterology & Nutrition (1998); 26(4): 380-385.
Lipka, et al., "The natural history of steroid-nave eosinophilic esophagitis in adults treated with endoscopic dilation and proton pump inhibitor therapy over a mean duration of nearly 14 years." Gastrointest Endosc. (2014); 80(4): 592-598.
Mahmoudi et al. "Effect of drug particle size on blend segregation and content uniformity". Contributed poster, AAPS Annual Meeting (USA) 2010, 1 page. (non-English).
Mahmoudi et al. "Influence of filler in blend uniformity of micronized drugs". Contributed poster, AAPS Annual Meeting (USA) 2010, 1 page.
Malaysian Application No. PI 2012001434, Search Report dated Jan. 29, 2016, 1 page.

(56) References Cited

OTHER PUBLICATIONS

Martin, et al., "Pediatric Eosinophilic Esophagitis Symptom Scores (PEESS® v2.0) identify histologic and molecular correlates of the key clinical features of disease". J Allergy Clin Immunol. (Jun. 2015); 135(6): 1519-1528.e8.

Mcginity, J. W., et al. "Dissolution and uniformity properties of ordered mixes of micronized griseofulvin and a directly compressible excipient." Drug Development and Industrial Pharmacy, 11(4): 891-900 (1985).

Merck Index, "Budesonide," 14th Edition, p. 240 (2006).

Merck Index, "Ciclesonide," 14th Edition, p. 376 (2006).

Merck Index, "Clotrimazole," 14th Edition, p. 407 (2006).

Merck Index, "Mometasone Furoate," 14th Edition, pp. 1077-1078 (2006).

Merck Index, "Voriconazole," 14th Edition, p. 1728 (2006).

Miehlke, et al., "A randomised, double-blind trial comparing budesonide formulations and dosages for short-term treatment of eosinophilic oesophagitis", Gut (2016); 65: 390-399.

Moreton, R. Christian, "Disintegrants in Tableting". In book: Pharmaceutical Dosage Forms: Tablets, vol. 2, Herausgeber Augsburger & Hoag, CRC Press, Taylor and Francis Group (2008); Ch. 6, pp. 217-249, 33 pages.

New World Encyclopedia, "Gastrointestinal tract", https://web.archive.org/web/20090917122455/https://www.newworldencyclopedia. or . . . , Jul. 8, 2019, 7 pages.

New World Encyclopedia, "Gastrointestinal tract", https://www.newworldencyclopedia.org/entry/Gastrointestinal_tract, Jul. 8, 2019, 6 pages.

Nishimura, S., et al. "Factors associated with esophageal candidiasis and its endoscopic severity in the era of antiretroviral therapy." PLoS One (2013); 8(3): e58217, 6pgs.

Novopulmon E Novolizer, Instructions for the medical use of the medicament, [Instrukciya po medicinskomu primeneniyu preparata Novopulmon Novolizer (international nonproprietary name: budesonide), registracionniy nomer N LS-002405-231211, Nov. 23, 2011], MEDA Manufacturing, GmbH Registration No. LS-002405, Date of Registration Dec. 23, 2011 (with English summary of relevant portions), 9 pages.

"Nurofen" tablet package insert, 200 MG Tablets and Capsules, Date of revision: Feb. 2018, Reference ID 3039860, and English version, 2 pages.

Opposition Proceedings in European Patent No. 2886108 (Appln. No. 13199278.6), filed by Adare Development, I, L.P on Nov. 6, 2019, EPO Communication dated Apr. 6, 2021, enclosing Patentee's Response to Submissions dated Mar. 30, 2021, and English translation, 9 pages.

Opposition Proceedings in European Patent No. EP 2482822 (Appln. No. 10821232.5), filed by Dr. Falk Pharma GmbH on Mar. 1, 2019; Appeal No. T1954/21-3.3.01 dated Jan. 4, 2022, 20 pages.

Opposition Proceedings in European Patent No. EP 2886108 (Appln. No. 13199278.6), filed by Ellodi Pharmaceuticals, L.P., on Nov. 6, 2019, Interlocutory Decision dated Jan. 5, 2022, and English translation, 43 pages.

Opposition Proceedings in European Patent No. EP 2886108 (Appln. No. 13199278.6), filed by Ellodi Pharmaceuticals, L.P., on Nov. 6, 2019, Minutes of Oral Proceedings dated Jan. 5, 2022, and English translation, 25 pages.

Opposition Proceedings in European Patent No. EP 3041476 (Appln. No. 14842811.3), filed by Dr. Falk Pharma GmbH on Jul. 22, 2020; EPO's Communication dated Nov. 18, 2021 enclosing Opponent's, Dr. Falk Pharma GmbH's Further Submissions dated Nov. 15, 2021, and English translation, 21 pages.

Opposition Proceedings in European Patent No. EP 3041476 (Appln. No. 14842811.3), filed by Dr. Falk Pharma GmbH on Jul. 22, 2020; Interlocutory Decision dated Feb. 14, 2022, 61 pages.

Opposition Proceedings in European Patent No. 2482822 (Appln. No. 1082123205), filed by Dr. Falk Pharma GmbH on Mar. 1, 2019, D18—Dr F's novelty table 2020, 2 pages.

Opposition Proceedings in European Patent No. 2482822 (Appln. No. 1082123205), filed by Dr. Falk Pharma GmbH on Mar. 1, 2019, EPO Communication—communication of notice of opposition dated May 13, 2019, 1 page.

Opposition Proceedings in European Patent No. 2482822 (Appln. No. 1082123205), filed by Dr. Falk Pharma GmbH on Mar. 1, 2019, EPO Communication dated Nov. 5, 2019, enclosing Opponent's Further Written Submissions dated/filed on Oct. 29, 2019 (and English translation) including consolidated list of prior art, 29 pages.

Opposition Proceedings in European Patent No. 2482822 (Appln. No. 1082123205), filed by Dr. Falk Pharma GmbH on Mar. 1, 2019, EPO Communication dated Sep. 26, 2019, transmitting Adare's submission filed Sep. 20, 2019, 88 pages.

Opposition Proceedings in European Patent No. 2482822 (Appln. No. 1082123205), filed by Dr. Falk Pharma GmbH on Mar. 1, 2019, Notice of Opposition dated Mar. 1, 2019, and English translation, 23 pages.

Opposition Proceedings in European Patent No. 2482822 (Appln. No. 1082123205), filed by Dr. Falk Pharma GmbH on Mar. 1, 2019, Patentee, Adare Development I, L.P.'s Response dated Dec. 16, 2019 in response to further submissions filed by Dr. Falk Pharma GmbH on Oct. 29, 2019, 16 pages.

Opposition Proceedings in European Patent No. 2482822 (Appln. No. 1082123205), filed by Dr. Falk Pharma GmbH on Mar. 1, 2019, Submission filed by Adare Development I, L.P., on Sep. 20, 2019, 91 pages.

Opposition Proceedings in European Patent No. 2482822 (Appln. No. 10821232.5), filed by Dr. Falk Pharma GmbH on Mar. 1, 2019, EPO Communication dated Nov. 5, 2019, forwarding Letter from Opponent dated Oct. 29, 2019, 247 pages.

Opposition Proceedings in European Patent No. 2886108 (Appln. No. 13199278.6), filed by Adare Development, I, L.P on Nov. 6, 2019, Consolidated List of Cited Opposition Documents, 1 page.

Opposition Proceedings in European Patent No. 2886108 (Appln. No. 13199278.6), filed by Adare Development, I, L.P on Nov. 6, 2019, EPO Communication dated Jul. 24, 2020 regarding oral proceedings, 6 pages.

Opposition Proceedings in European Patent No. 2886108 (Appln. No. 13199278.6), filed by Adare Development, I, L.P on Nov. 6, 2019, EPO Communication dated Mar. 25, 2020 transmitting communication from Dr. Falk Pharma GmbH dated Mar. 20, 2020, and English translation, 34 pages.

Opposition Proceedings in European Patent No. 2886108 (Appln. No. 13199278.6), filed by Adare Development, I, L.P on Nov. 6, 2019, EPO Communication re Summons to Attend Oral Proceedings and Preliminary Opinion, dated Jul. 2, 2020, and English translation, 18 pages.

Opposition Proceedings in European Patent No. 2886108 (Appln. No. 13199278.6), filed by Ellodi Pharmaceuticals, L.P., on Nov. 6, 2019, Adare's Written Submissions in Preparation for Oral Proceedings on Apr. 23, 2021, dated Feb. 23, 2021, 25 pages.

Opposition Proceedings in European Patent No. 3086782 (Appln. No. 14814872.9), filed by Adare Development, I, L.P on Jun. 26, 2019, EPO Communication dated Jul. 2, 2019, transmitting Notice of Opposition filed Jun. 26, 2019, 43 pages.

Opposition Proceedings in European Patent No. 3086782 (Appln. No. 14814872.9), filed by Adare Development, I, L.P on Jun. 26, 2019, EPO Communication dated Jul. 22, 2020 regarding date of oral proceedings, 3 pages.

Opposition Proceedings in European Patent No. 3086782 (Appln. No. 14814872.9), filed by Adare Development, I, L.P on Jun. 26, 2019, EPO Communication dated Nov. 19, 2019, with Patentee's response to Opposition dated Nov. 8, 2019, and English translation, 22 pages.

Opposition Proceedings in European Patent No. 3086782 (Appln. No. 14814872.9), filed by Adare Development, I, L.P on Jun. 26, 2019, EPO Communication to Adare regarding oral proceedings dated Mar. 2, 2020, and English translation, 14 pages.

Opposition Proceedings in European Patent No. 3086782 (Appln. No. 14814872.9), filed by Adare Development, I, L.P on Jun. 26, 2019, Patentee, Dr. Falk's Written Submissions, Auxiliary Request

(56) References Cited

OTHER PUBLICATIONS

I and Test Report Jorveza® 1 mg (dated Aug. 18, 2020, produced by Patentee, Dr. Falk Pharma), filed Sep. 10, 2020, and English translation, 22 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; communication from the European Patent Office (EPO) dated May 18, 2022 enclosing Opponent's response to appeal dated May 12, 2022 and D27, and English translation, 44 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; Ellodi's Withdrawal of Appeal dated Jul. 11, 2022, 3 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; EPO's Communication—Minutes of Oral Proceeding, dated Aug. 25, 2021, and English translation, 11 pages.

Opposition Proceedings in European Patent No. EP 2482822 (Appln. No. 1082123205), filed by Dr. Falk Pharma GmbH on Mar. 1, 2019, Adare—Letter to EPO re Oral Proceedings dated Jul. 17, 2020, 5 pages.

Opposition Proceedings in European Patent No. EP 2482822 (Appln. No. 1082123205), filed by Dr. Falk Pharma GmbH on Mar. 1, 2019; Adare's Communication to the EPO re oral proceedings, dated Aug. 11, 2020, 4 pages.

Opposition Proceedings in European Patent No. EP 2482822 (Appln. No. 1082123205), filed by Dr. Falk Pharma GmbH on Mar. 1, 2019; EPO Communication dated Jul. 23, 2020, with Written Submission from Adare (Proprietor) dated Jul. 17, 2020, 126 pages.

Opposition Proceedings in European Patent No. EP 2482822 (Appln. No. 1082123205), filed by Dr. Falk Pharma GmbH on Mar. 1, 2019, EPO Communication dated Mar. 8, 2019 regarding notice of opposition, 1 page.

Opposition Proceedings in European Patent No. EP 2482822 (Appln. No. 1082123205), filed by Dr. Falk Pharma GmbH on Mar. 1, 2019; EPO's Communication re oral proceedings, dated Aug. 5, 2020, 1 page.

Opposition Proceedings in European Patent No. EP 2482822 (Appln. No. 1082123205), filed by Dr. Falk Pharma GmbH on Mar. 1, 2019, EPO Communication re Oral Proceedings dated Jul. 13, 2020, 3 pages.

Opposition Proceedings in European Patent No. EP 2482822 (Appln. No. 1082123205), filed by Dr. Falk Pharma GmbH on Mar. 1, 2019; EPO's consolidated list of cited opposition documents, Jul. 18, 2020, 1 page.

Opposition Proceedings in European Patent No. EP 2482822 (Appln. No. 1082123205), filed by Dr. Falk Pharma GmbH on Mar. 1, 2019, Summons to Attend Oral Hearing and Preliminary Opinion in opposition dated Feb. 13, 2020, 15 pages.

Opposition Proceedings in European Patent No. EP 2482822 (Appln. No. 1082123205), filed by Dr. Falk Pharma GmbH on Mar. 1, 2019, Summons to attend oral proceedings dated Feb. 13, 2020, 13 pages.

Opposition Proceedings in European Patent No. EP 2482822 (Appln. No. 1082123205), filed by Dr. Falk Pharma GmbH on Mar. 1, 2019; Written Submissions of the Patentee in Preparation for Oral Proceedings on Mar. 8, 2021, dated Jan. 8, 2021, with Auxiliary Requests 1-14, 52 pages.

Opposition Proceedings in European Patent No. EP 2482822 (Appln. No. 10821232.5), filed by Dr. Falk Pharm a GmbH on Mar. 1, 2019; EPO's Decision revoking European Patent No. 2482822, dated Aug. 25, 2021, 23 pages.

Opposition Proceedings in European Patent No. EP 2482822 (Appln. No. 10821232.5), filed by Dr. Falk Pharma GmbH on Mar. 1, 2019; EPO Communication in connection with Summons to attend oral proceedings, dated Nov. 20, 2020, 12 pages.

Opposition Proceedings in European Patent No. EP 2482822 (Appln. No. 10821232.5), filed by Dr. Falk Pharma GmbH on Mar. 1, 2019; Falk's Communication to the EPO re oral proceedings, dated Aug. 12, 2020, 3 pages.

Opposition Proceedings in European Patent No. EP 2482822 (Appln. No. 10821232.5), filed by Dr. Falk Pharma GmbH on Mar. 1, 2019, Opponent's response to Summons dated Jul. 17, 2020, and English translation, 15 pages.

Opposition Proceedings in European Patent No. EP 2482822 (Appln. No. 10821232.5), filed by Dr. Falk Pharma GmbH on Mar. 1, 2019; Opponent's submissions dated Mar. 1, 2021, and English translation, 11 pages.

Opposition Proceedings in European Patent No. EP 2482822 (Appln. No. 10821232.5), filed by Dr. Falk Pharma GmbH on Mar. 1, 2019; Written Submissions of the Opponent in response to the Summons to attend Oral Proceedings, dated and filed Dec. 8, 2020, and English translation, 37 pages.

Opposition Proceedings in European Patent No. EP 2886108, Appeal No. T0611/22-3.3.07 (Appln. No. 13199278.6), (in the name of Dr. Falk Pharma GmbH) filed by Ellodi Pharmaceuticals, L.P. on Nov. 6, 2019; EPO Communication dated May 27, 2022 confirming Termination of Appeal Proceedings filed May 16, 2022, 4 pages.

Opposition Proceedings in European Patent No. EP 2886108 (Appln. No. 13199278.6), filed by Adare Development I, L.P., on Nov. 6, 2019, Dr. Falk Pharma's Response to Summons and Adare's Written Submissions and clean and marked versions of Auxiliary Requests I and II, dated Dec. 18, 2020, and English translation, 26 pages.

Opposition Proceedings in European Patent No. EP 2886108 (Appln. No. 13199278.6), filed by Ellodi Pharmaceuticals, L.P., on Nov. 6, 2019, Datasheet for the decision of Oct. 14, 2019, Case No. T 1621/16-3.3.06, Application No. 09163237.2, 28 pages.

Opposition Proceedings in European Patent No. EP 2886108 (Appln. No. 13199278.6), filed by Ellodi Pharmaceuticals, L.P., on Nov. 6, 2019, Ellodi's Notice of Appeal against decision filed Mar. 4, 2022, 5 pages.

Opposition Proceedings in European Patent No. EP 2886108 (Appln. No. 13199278.6), filed by Ellodi Pharmaceuticals, L.P., on Nov. 6, 2019, Ellodi's Withdrawal of Appeal filed May 16, 2022, 3 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jul. 22, 2022 confirming withdrawal of appeal as filed Jul. 14, 2022 by Opponent, 4 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jun. 20, 2022 enclosing Opponent's Grounds of Appeal dated Jun. 10, 2022, and English translation, 27 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; Withdrawal of Appeal filed by Ellodi Pharmaceuticals, L.P. dated Jun. 14, 2022, 3 pages.

Opposition Proceedings in European Patent No. EP 3041476 (Appln. No. 14842811.3), filed by Dr. Falk Pharma GmbH on Jul. 22, 2020; EPO Communication dated Feb. 22, 2021 enclosing Opponent's Submissions (and English translation), dated Feb. 16, 2021, 11 pages.

Opposition Proceedings in European Patent No. EP 3041476 (Appln. No. 14842811.3), filed by Dr. Falk Pharma GmbH on Jul. 22, 2020; EPO Communication dated Jul. 29, 2020 advising of and enclosing Notice of Opposition filed by Dr. Falk Pharma GmbH on Jul. 22, 2020, 82 pages.

Opposition Proceedings in European Patent No. EP 3041476 (Appln. No. 14842811.3), filed by Dr. Falk Pharma GmbH on Jul. 22, 2020; Minutes of Oral Proceedings dated Feb. 14, 2022, 15 pages.

Opposition Proceedings in European Patent No. EP 3041476 (Appln. No. 14842811.3), filed by Dr. Falk Pharma GmbH on Jul. 22, 2020; Notice of Appeal filed by Ellodi Pharmaceuticals, L.P. dated Apr. 22, 2022, 5 pages.

Opposition Proceedings in European Patent No. EP 3041476 (Appln. No. 14842811.3), filed by Dr. Falk Pharma GmbH on Jul. 22, 2020; Notice of Opposition and Statement of Grounds of Opposition (with

(56)                    References Cited

OTHER PUBLICATIONS

English translation of Statement of Grounds of Opposition), and Consolidated List of references relied upon, filed Jul. 22, 2020, 513 pages.
Opposition Proceedings in European Patent No. EP 3041476 (Appln. No. 14842811.3), filed by Dr. Falk Pharma GmbH on Jul. 22, 2020; Patentee Adare's Response to Opposition dated .Jan. 11, 2021, 15 pages.
Opposition Proceedings in European Patent No. EP 3041476 (Appln. No. 14842811.3), filed by Dr. Falk Pharma GmbH on Jul. 22, 2020; Patentee Ellodi Pharmaceuticals, L.P.'s Written Submission in Preparation for Oral Proceedings on Dec. 8, 2021 with new Auxiliary Requests 1-3, dated Oct. 8, 2021, 51 pages.
Opposition Proceedings in European Patent No. EP 3403654 (Appln. No. 18178891.0), filed by Dr. Falk Pharma GmbH; Adare's Response to the Grounds of Opposition, filed Nov. 2, 2020, 78 pages.
Opposition Proceedings in European Patent No. EP 3403654 (Appln. No. 18178891.0), filed by Dr. Falk Pharma GmbH; Consolidated List of References dated and filed Dec. 8, 2020, 1 page.
Opposition Proceedings in European Patent No. EP 3403654 (Appln. No. 18178891.0), filed by Dr. Falk Pharma GmbH; EPO Communication of a notice of opposition dated Jun. 22, 2020, 1 page.
Opposition Proceedings in European Patent No. EP 3403654 (Appln. No. 18178891.0), filed by Dr. Falk Pharma GmbH; EPO Communication of a notice of opposition dated May 8, 2020, 1 page.
Opposition Proceedings in European Patent No. EP 3403654 (Appln. No. 18178891.0), filed by Dr. Falk Pharma GmbH; Opponent's Further Written Submissions dated and filed Dec. 8, 2020, and English translation, 30 pages.
Opposition Proceedings in European Patent No. EP 3403654 (Appln. No. 18178891.0), filed by Dr. Falk Pharma GmbH; Opponent's Submission/Withdrawal of Opposition dated Jul. 20, 2022, and English translation, 2 pages.
Opposition Proceedings in European Patent No. EP 3403654 (Appln. No. 18178891.0), filed by Dr. Falk Pharma GmbH; Statement of Grounds of Opposition filed on Apr. 28, 2020, and English translation, 38 pages.
Opposition Proceedings re Patent No. EP 2886108 (EP 13199278.6).
Patent Complaint Proceedings in the Regional Court, Mannheim, Germany, *Adare Development I, L.P.* vs. *Dr. Falk Pharma GmbH*, Reference No. 4c O Oct. 2019, Decision (and English translation) dated Oct. 26, 2020, pronounced in the oral hearing of Jul. 21, 2020, 45 pages.
PCT Application No. PCT/US2010/050860, International Preliminary Report on Patentability dated Apr. 3, 2012.
PCT Application No. PCT/US2010/050860, International Search Report dated Feb. 10, 2011.
PCT Application No. PCT/US2010/050860, Written Opinion of the International Search Authority dated Feb. 10, 2011.
PCT Application No. PCT/US2014/052073, International Preliminary Report on Patentability dated Mar. 8, 2016.
PCT Application No. PCT/US2014/052073, International Search Report dated Nov. 20, 2014.
PCT Application No. PCT/US2014/052073, Written Opinion of the International Searching Authority dated Nov. 20, 2014.
PCT Application No. PCT/US2014/054203, International Preliminary Report on Patentability dated Mar. 8, 2016.
PCT Application No. PCT/US2014/054203, International Search Report dated Dec. 23, 2014.
PCT Application No. PCT/US2014/054203, Written Opinion of the International Searching Authority dated Dec. 23, 2014.
PCT Application No. PCT/US2019/019040, International Preliminary Report on Patentability, dated Aug. 27, 2020, 8 pages.
PCT Application No. PCT/US2019/019040, International Search Report and Written Opinion, mailed Jun. 25, 2019, 12 pages.
PCT Application No. PCT/US2019/019040, Invitation to Pay Additional Fees, mailed Apr. 25, 2019, 2 pages.
PCT/US2020/053778, International Preliminary Report on Patentability mailed Apr. 5, 2022, 7 pages.

PCT/US2020/053778, International Search Report and Written Opinion mailed Jan. 8, 2021, 9 pages.
PCT/US2021/042566, International Search Report and Written Opinion, mailed Nov. 5, 2021, 9 pages.
Pelle, et al., "Using defined daily doses to study the use of antibacterials in UK hospitals". Hosp Pharm (2006); 13: 133-136.
Ponchel, Gilles, "Formulation of oral mucosal drug delivery systems for the systemic delivery of bioactive materials". Advanced Drug Delivery Reviews, vol. 13, Issues 1-2, Jan.-Feb. 1994, pp. 75-87.
Ratnaparkhi, et al., "Review On: Fast Dissolving Tablet", Journal of Pharmacy Research. (Jan. 2009); 2(1): 5-12.
Remedios, et al., "Eosinophilic esophagitis in adults: clinical, endoscopic, histologic findings, and response to treatment with fluticasone propionate". Gastrointestinal Endoscopy (2006); 63(1): 3-12.
Robertson, et al., "Oesophageal transit of small tablets", J. Pharm. Pharmacol. (1988); 40: 595-596.
Schaefer, et al., "Comparison of Oral Prednisone and Topical Fluticasone in the Treatment of Eosinophilic Esophagitis: A Randomized Trial in Children". Clinical Gastroenterology and Hepatology (2008); 6: 165-173.
Schoepfer, et al., "Development and validation of a symptom-based activity index for adults with eosinophilic esophagitis". Gastroenterology (Dec. 1, 2014); 147(6): 1255- 1266.
Singh, Arun, et al. "Oral candidiasis: An overview." Journal of Oral and Maxillofacial Pathology: JOMFP (2014); 18.Suppl 1: S81.
Sjostrom and Cairncross, "What Makes Flavor Leadership." Food Technology (1953); (7) 2: 56-58.
Supplementary European Search Report in European Patent Application No. EP 20192973.4, dated Nov. 18, 2020, 5 pages.
Taft, et al., "The adult eosinophilic oesophagitis quality of life questionnaire: a new measure of health-related quality of life". Alimentary Pharmacology & Therapeutics (Oct. 2011); 34(7): 790-798.
Taiwanese Application No. TW 099133628, Search Report (English translation) dated Nov. 16, 2014, 9 pages.
Taiwanese Application No. TW 104107443, Search Report (English translation) dated May 29, 2015,1 page.
Takaku, Fumimaro, et al. Manual of Therapeutic Agents 2007, Published 2007, p. 617-619 (and English translation/summary of pertinent paragraphs), 5 pages.
Tayebi and Mortazavi, "Formulation and Evaluation of a Novel Matrix-Type Orally Disintegrating Ibuprofen Tablet". Iran J Pharm Res. (2011 Summer); 10(3): 469-479.
Teitelbaum et al. "Eosinophilic esophagitis in children: immunopathological analysis and response to fluticasone propionate." Gastroenterology (2002), 122(5): 1216-1225.
Thorburn and Ferguson, "Topical corticosteroids and lesions of the oral mucosa". Advanced Drug Delivery Reviews, vol. 13, Issues 1-2, Jan.-Feb. 1994, pp. 135-149.
UM Complaint Proceedings in the Regional Court, Mannheim, Germany, *Adare Development I, L.P.* vs. *Dr. Falk Pharma GmbH*, Reference No. 4c O Oct. 2019, Replica dated Jul. 19, 2019, and English translation, 25 pages.
UM Complaint Proceedings in the Regional Court, Mannheim, Germany, *Adare Development I, L.P.* vs. *Dr. Falk Pharma GmbH*, Complaint dated Jul. 3, 2019, and English translation, 34 pages.
UM Complaint Proceedings in the Regional Court, Mannheim, Germany, *Adare Development I, L.P.* vs. *Dr. Falk Pharma GmbH*, Reference No. 4c O Oct. 2019, submission by Dr. Falk Pharma GmbH—statement of defense, dated May 24, 2019, and English translation, 16 pages.
UM Complaint Proceedings in the Regional Court, Mannheim, Germany, *Adare Development I, L.P.* vs. *Dr. Falk Pharma GmbH*, Reference No. 4c O Oct. 2019, Submission of Dr. Falk—Rejoinder dated Sep. 13, 2019 (English translation), 8 pages.
UM Complaint Proceedings in the Regional Court, Mannheim, Germany, *Ellodi Pharmaceuticals, L.P.* (formerly Adare Development I, L.P.) vs. *Dr. Falk Pharma GmbH*, Reference No. 4c O Oct. 2019, Defendant's Consent to Withdrawal filed Jul. 15, 2022, and English translation, 2 pages.

(56) References Cited

OTHER PUBLICATIONS

UM Complaint Proceedings in the Regional Court, Mannheim, Germany, *Ellodi Pharmaceuticals, L.P.* (formerly Adare Development I, L.P.) vs. *Dr. Falk Pharma GmbH*, Reference No. 4c O Oct. 2019, Order concerning value under dispute dated Jul. 20, 2022, and English translation, 2 pages.

UM Complaint Proceedings in the Regional Court, Mannheim, Germany, *Ellodi Pharmaceuticals, L.P.* (formerly Adare Development I, L.P.) vs. *Dr. Falk Pharma GmbH*, Reference No. 4c O Oct. 2019, Withdrawal Submission filed by Ellodi Pharmaceuticals, L.P., dated Jul. 11, 2022, and English translation, 2 pages.

Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB1 "Breakdown of Features", and English translation, 2 pages.

Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB4—Letter from Lederer & Keller dated Sep. 27, 2018 regarding European Patent No. 2211896, and Machine English translation, 28 pages.

Vogt et al., "Biowaiver monographs for immediate release solid oral dosage forms: Prednisolone," Journal of Pharmaceutical Sciences, 96(1): 27-37 (2007).

Von Arnim and Malfertheiner, "Eosinophilic Esophagitis—Treatment of Eosinophilic Esophagitis with Drugs: Corticosteroids", Digestive Diseases (2014); 32: 126-129.

Webb, Paul A., "Surface Area, Porosity, and Related Physical Characteristics". In book: Pharmaceutical Dosage Forms: Tablets, 3rd Edition, vol. 3, CRC Press, Taylor and Francis Group, Boca Raton, London, New York (2008); Chapter 11, pp. 277-302.

Wechsler, Joshua B., et al. "Eosinophilic esophagitis reference score accurately identifies disease activity and treatment effects in children." Clinical Gastroenterology and Hepatology (2018); 16(7): 1056-1063.

Wei et al., "Efficacy of Single-Dose Dexamethasone as Adjuvant Therapy for Acute Pharyngitis" The Laryngoscope, 112(1):87-93 (2002).

Wen, Hong, (ed. Swarbick, James) "Adsorption at Solid Surfaces: Pharmaceutical Applications". Encyclopedia of Pharmaceutical Technology, Third Edition, vol. 1 (2007); pp. 34-38, 7 pages.

Wikipedia, "Retard", https://de.wikipedia.org/wiki/Retard, Jun. 13, 2019, and Google machine translation, 7 pages.

Yalkowsky and Bolton. "Particle size and content uniformity." Pharmaceutical Research, 7(9): 962-966 (1990).

Co-pending U.S. Appl. No. 18/287,416, inventor Eagle; Gina , filed Oct. 18, 2023.

Faubion Jr., et al., "Treatment of eosinophilic esophagitis with inhaled corticosteroids". Journal of Pediatric Gastroenterology and Nutrition. Jul. 1, 1998; 27(1): 90-93, 6 pages.

International Preliminary Report on Patentability for International Application No. PCT/US2022/025297 dated Nov. 2, 2023, 8 pages.

Dellon E.S., "Safety and Efficacy of Budesonide Oral Suspension Maintenance Therapy in Patients With Eosinophilic Esophagitis", Clin Gastroenterol Hepatol. Mar. 2019; 17(4): 666-673.e8. Epub Jun. 12, 2018.

Extended European Search Report for European Application No. EP 20873169.5 dated Sep. 22, 2023, 9 pages.

Hirano, I., et al. "Randomised clinical trial: the safety and tolerability of fluticasone propionate orally disintegrating tablets versus placebo for eosinophilic oesophagitis", Aliment Pharmacol Ther. Apr. 2020;51(8):750-759. Epub Mar. 9, 2020.

Konikoff, et al., "A Randomized, Double-Blind, Placebo-Controlled Trial of Fluticasone Propionate for Pediatric Eosinophilic Esophagitis". Gastroenterology. Nov. 2006; 131(5): 1381-1391. Epub Aug. 16, 2006.

Schoepfer, et al., "Delay in diagnosis of eosinophilic esophagitis increases risk for stricture formation in a time-dependent manner". Gastroenterology. Dec. 2013; 145(6): 1230-1236. Epub Aug. 13, 2013.

Straumann et al., "Budesonide Orodispersible Tablets Maintain Remission in a Randomized, Placebo-Controlled Trial of Patients With Eosinophilic Esophagitis". Gastroenterology. Nov. 2020; 159(5): 1672-1685. e5. Epub Jul. 25, 2020.

Sodikoff et al., "Therapeutic strategies in eosinophilic esophagitis: Induction, maintenance and refractory disease", Best Pract Res Clin Gastroenterol. (Oct. 2015); 29(5): 829-839.

Straumann et al., "Budesonide is effective in adolescent and adult patients with active eosinophilic esophagitis", Gastroenterology (Nov. 2010); 139(5): 1526-1537.

Straumann et al., "Long-term budesonide maintenance treatment is partially effective for patients with eosinophilic esophagitis", Clin Gastroenterol Hepatol. (May 2011); 9(5): 400-409.

Allen, L.V. and Luner, P.E., "Magnesium Stearate", Date of Revision: Aug. 9, 2005, In: Handbook of Pharmaceutical Excipients, 5th Ed. (2006), Raymond C. Rowe, et al. (eds); pp. 430-433, 7 pages.

Armstrong, N.A., "Mannitol", Date of Revision: Aug. 16, 2005, In: Handbook of Pharmaceutical Excipients, 5th Ed. (2006), Raymond C. Rowe, et al. (eds); pp. 449-453, 7 pages.

Budenofalk®, Budenofalk®3mg, Dr. Falk Pharma GMBH, Brochure (6th Revised Edition 2005), 136 pages.

Budenofalk®, Budesonide Budenofalk®3mg, First-line-corticosteroid, Dr. Falk Pharma GMBH, Advertisement (2007), 1 page.

Conway, B.R., "Solid Dosage Forms", In: Pharmaceutical Manufacturing Handbook: Production and Processes (2008); by GAD, Shayne Cox; Ch. 4.1, pp. 235-265, 36 pages.

Curriculum Vitae of Alan F. Parr, Pharm.D., Ph.D., filed Jul. 22, 2024 in Petition for Inter Partes Review of U.S. Pat. No. 8,771,729 filed Jul. 22, 2024, 12 pages.

Danckwerts, M.D., "Intraoral Drug Delivery: A Comparative Review," American Journal of Drug Delivery (Sep. 2003); 1(3): 171-186.

Declaration of Alan F. Parr, Pharm.D., Ph.D., in Support of Petition for Inter Partes Review (IPR2025-00052) of U.S. Pat. No. 10,632,069 dated Oct. 8, 2024, filed Oct. 24, 2024, 165 pages.

Declaration of Alan F. Parr, Pharm.D., Ph.D., in Support of Petition for Inter Partes Review (IPR2025-00054) of U.S. Pat. No. 11,246,828 dated Oct. 8, 2024, filed Oct. 24, 2024, 197 pages.

Declaration of Alan F. Parr, Pharm.D., Ph.D., in Support of Petition for Inter Partes Review (IPR2025-00055) of U.S. Pat. No. 9,486,407 dated Oct. 22, 2024, filed Oct. 24, 2024, 220 pages.

Declaration of Alan F. Parr, Pharm.D., Ph.D., in Support of Petition for Inter Partes Review (IPR2025-00056) of U.S. Pat. No. 11,260,061 dated Oct. 21, 2024, filed Oct. 24, 2024, 195 pages.

Declaration of Alan F. Parr, Pharm.D., Ph.D., in Support of Petition for Inter Partes Review of U.S. Pat. No. 8,771,729 dated Apr. 17, 2024, filed Jul. 22, 2024, 174 pages.

Definition of "Adsorption", McGraw-Hill Dictionary of Scientific and Technical Terms, Sixth Edition (2003); p. 41, 3 pages.

Dellon, E.S. et al., "Budesonide Oral Suspension Improves Symptomatic, Endoscopic, and Histologic Parameters Compared With Placebo in Patients With Eosinophilic Esophagitis". Gastroenterology. Mar. 2017; 152(4): 776-786.e5. Epub Nov. 23, 2016.

Dr. Falk Pharma, "Where medicine and pharmaceuticals meet—a tried and trusted link", Dr. Falk Pharma GmbH, Brochure (2008), 29 pages.

"Draft Guidance: Guidance for Industry: Orally Disintegrating Tablets," U.S. Department of Health and Human Services, Food & Drug Administration, Center for Drug Evaluation and Research (CDER), Apr. 2007, 6 pages.

El-Arini, S.K., et al., "Evaluation of disintegration testing of different fast dissolving tablets using the texture analyzer", Pharm Dev Technol. 2002; 7(3): 361-371.

Elsing et al., "Budesonide for the treatment of obstructive eosinophilic jejunitis," Z. Gastroenterology Feb. 2007; 45(2): 187-189.

European Application No. EP 22792291.1, Extended European Search Report dated Feb. 21, 2025, 11 pages.

Fu et al., "Orally fast disintegrating tablets: developments, technologies, taste-masking and clinical studies," Critical Reviews in Therapeutic Drug Carrier Systems (2004); 21(6): 433-475.

(56)                References Cited

OTHER PUBLICATIONS

Fujiwara, J., et al., "A Case Report of Eosinophilic Esophagitis with a Stricture Successfully Treated Using Fluticasone Swallowing Therapy". Gastroenterological Endoscopy. Nov. 2, 20118; 53(11): 3523-3528.

Goodman & Gilman's: The Pharmacological Basis of Therapeutics, 11th edition, eds. Brunton, Lazo, Parker, 2006, Ch. 38, pp. 1014-1015, pp. 1246-1256, 15 pages.

"Guidance for Industry: Orally Disintegrating Tablets," U.S. Department of Health and Human Services, Food & Drug Administration, Center for Drug Evaluation and Research (CDER), Dec. 2008, 6 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Decision Granting Institution of Inter Partes Review 35 U.S.C. § 314 dated Jan. 27, 2025, 43 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Decision Granting Patent Owner's Motion for Admission Pro Hac Vice of Isha Agarwal 37 C.F.R. § 42.10 entered Apr. 1, 2025, 4 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Exhibit 2005, Biography of Isha Agarwal, filed Mar. 5, 2025, 1 page.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Exhibit 2006, Declaration of Isha Agarwal in Support of Motion for Pro Hac Vice Admission, 2 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Notice of Deposition of Alan F. Parr, Pharm.D, Ph.D. dated Mar. 19, 2025, 3 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Objections Pursuant to 37 C.F.R. § 42.64(b)(1) dated Feb. 10, 2025, 12 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Preliminary Response, dated and filed Oct. 29, 2024, 59 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Surreply, dated and filed Dec. 4, 2024, 8 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Updated Exhibit List dated Mar. 5, 2025, 3 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Petition for Inter Partes Review of U.S. Pat. No. 8,771,729, dated and filed Jul. 22, 2024, including Exhibits and Petitioner Power of Attorney dated Mar. 24, 2024, 1079 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Petitioner's Reply to Patent Owner's Preliminary Response dated and filed Nov. 26, 2024, 8 pages.

Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Petitioner's Supplemental Mandatory Notice: Related Matters Section dated and filed Nov. 26, 2024, 4 pages.

Inter Partes Review Proceedings No. IPR2025-00052 filed Oct. 24, 2024, Dr. Falk Pharma GMBH (Petitioner) vs. Ellodi Pharmaceuticals LP (Patent Owner), Petition for Inter Partes Review of U.S. Pat. No. 10,632,069 (U.S. Appl. No. 15/816,154), dated and filed Oct. 24, 2024, and Petitioner Power of Attorney dated Jun. 8, 2024, 83 pages.

Inter Partes Review Proceedings No. IPR2025-00052 filed Oct. 24, 2024, Dr. Falk Pharma GMBH (Petitioner) vs. Ellodi Pharmaceuticals LP (Patent Owner), U.S. Pat. No. 10,632,069 (U.S. Appl. No. 15/816,154), Petitioner's Supplemental Mandatory Notice: Related Matters Section dated and filed Dec. 17, 2024, 3 pages.

Inter Partes Review Proceedings No. IPR2025-00054 filed Oct. 24, 2024, Dr. Falk Pharma GMBH (Petitioner) vs. Ellodi Pharmaceuticals LP (Patent Owner), Petition for Inter Partes Review of U.S. Pat. No. 11,246,828 (U.S. Appl. No. 16/821,464), dated and filed Oct. 24, 2024, and Petitioner Power of Attorney dated Jun. 8, 2024, 91 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Supplemental Mandatory Notice: Related Matters Section dated and filed Dec. 17, 2024, 3 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), dated and filed Oct. 24, 2024, and Petitioner Power of Attorney dated Jun. 8, 2024, 103 pages.

Inter Partes Review Proceedings No. IPR2025-00056 filed Oct. 24, 2024, Dr. Falk Pharma GMBH (Petitioner) vs. Ellodi Pharmaceuticals L.P., Declaration of Martyn Christopher Davies dated and filed Mar. 12, 2025, 62 pages.

Inter Partes Review Proceedings No. IPR2025-00056 filed Oct. 24, 2024, Dr. Falk Pharma GMBH (Petitioner) vs. Ellodi Pharmaceuticals L.P., Exhibit 2002, Merriam-Webster's Collegiate Dictionary, 11th ed. (2006)—definitions of "adsorption" and "disposition", filed Mar. 12, 2025, 4 pages.

Inter Partes Review Proceedings No. IPR2025-00056 filed Oct. 24, 2024, Dr. Falk Pharma GMBH (Petitioner) vs. Ellodi Pharmaceuticals L.P., Exhibit 2003, Curriculum Vitae Martyn Christopher Davies CBE DSc FRPharmS CChem FRSC Emeritus Professor in Biomedical Surface Chemistry, filed Mar. 12, 2025, 57 pages.

Inter Partes Review Proceedings No. IPR2025-00056 filed Oct. 24, 2024, Dr. Falk Pharma GMBH (Petitioner) vs. Ellodi Pharmaceuticals L.P., Patent Owner), Patent Owner's Response 37 C.F.R. § 42.107 dated and filed Mar. 12, 2025, 65 pages.

Inter Partes Review Proceedings No. IPR2025-00056 filed Oct. 24, 2024, Dr. Falk Pharma GMBH (Petitioner) vs. Ellodi Pharmaceuticals L.P. (Patent Owner), Petition for Inter Partes Review of U.S. Pat. No. 11,260,061 (U.S. Appl. No. 17/211,119), dated and filed Oct. 24, 2024, and Petitioner Power of Attorney dated Jun. 8, 2024, 107 pages.

Inter Partes Review Proceedings No. IPR2025-00056 filed Oct. 24, 2024, Dr. Falk Pharma GMBH (Petitioner) vs. Ellodi Pharmaceuticals L.P. (Patent Owner), Redline comparison of Dohil (US2007/0111978) and Dohil 2009 (US2009/0191275), Exhibit 1059 filed Oct. 24, 2024, 47 pages.

Inter Partes Review Proceedings No. IPR2025-00056 filed Oct. 24, 2024, Dr. Falk Pharma GMBH (Petitioner) vs. Ellodi Pharmaceuticals L.P. (Patent Owner), U.S. Pat. No. 11,260,061 (U.S. Appl. No. 17/211,119), Petitioner's Supplemental Mandatory Notice: Related Matters Section dated and filed Dec. 17, 2024, 3 pages.

Invitation to Pay Additional fees for International Application No. PCT/US2024/059722, mailed Feb. 18, 2025, 2 pages.

Khan et al., "An Approach for Rapid Disintegrating Tablet: a Review", IJPRD, May 2011; vol. 3(3): 21; pp. 170-183.

(56) References Cited

OTHER PUBLICATIONS

Kibbe, A.H., "Povidone", Date of Revision: Aug. 30, 2005, In: Handbook of Pharmaceutical Excipients, 5th Ed. (2006), Raymond C. Rowe, et al. (eds); pp. 611-616, 9 pages.

Kolkman et al., "Evaluation of oral budesonide in the treatment of active distal ulcerative colitis," Drugs of Today Jul. 2004; 40(7): 589-601.

Martin, Alfred, et al., "Adsorption at Solid Interfaces", (with the participation of Pilar Bustamente), In: Physical Pharmacy: Physical Chemical Principles in the Pharmaceutical Sciences, Fourth Edition (1993); Print. No. 10, Ch. 14, pp. 379-386, 11 pages.

Moreton, R.C., "Cellulose, Silicified Microcrystalline", Date of Revision: Aug. 26, 2005, In: Handbook of Pharmaceutical Excipients, 5th Ed. (2006), Raymond C. Rowe, et al. (eds); pp. 139-141, 5 pages.

Noel et al., "Clinical and immunopathologic effects of swallowed fluticasone for eosinophilic esophagitis," Clinical Gastroenterology and Hepatology Jul. 2004; 2(7): 568-575.

Notice of Publication of FDA Guidance for Industry on Orally Disintegrating Tablets, Federal Register, vol. 73, No. 242 at 76366, Dec. 16, 2008, 1 page.

Opposition Proceedings in European Patent No. 2482822 B1 (Appln. No. 10821232.5), filed by Dr. Falk Pharma GmbH on Mar. 1, 2019, Adare Development I, L.P.'s (now Ellodi Pharmaceuticals, L.P.) Response to Grounds of Opposition dated Sep. 20, 2019, 27 pages.

Opposition Proceedings in European Patent No. EP 2482822 (Appln. No. 10821232.5), filed by Dr. Falk Pharma GmbH on Mar. 1, 2019; EPO's Decision revoking European Patent No. 2482822, dated Aug. 25, 2021, 31 pages.

Opposition Proceedings in European Patent No. EP 3041476 (Appln. No. 14842811.3), filed by Dr. Falk Pharma GmbH on Jul. 22, 2020; Interlocutory Decision dated Jan. 26, 2022, 30 pages.

Pesek, R.D., et al., "Emerging drugs for eosinophilic esophagitis". Expert Opin Emerg Drugs. Jun. 2018; 23(2): 173-183. Epub Jun. 8, 2018.

Price, J.C., "Polyethylene Glycol", Date of Revision: Aug. 29, 2005, In: Handbook of Pharmaceutical Excipients, 5th Ed. (2006), Raymond C. Rowe, et al. (eds); pp. 545-550, 8 pages.

Prosecution history excerpts from U.S. Appl. No. 12/896,005, filed Oct. 1, 2010, for Orally Administered Corticosteroid Compositions; Inventors Perrett, Stephen et al., issued as U.S. Pat. No. 8,771,729, 119 pages.

Prosecution history excerpts from U.S. Appl. No. 14/917,125, filed Sep. 5, 2014, for Corticosteroid Containing Orally Disintegrating Tablet Compositions for Eosinophilic Esophagitis; Inventors Gosselin, Michael A., issued as U.S. Pat. No. 10,471,071, 123 pages.

Prosecution history excerpts from U.S. Appl. No. 15/816,154, filed Nov. 17, 2017, for Orally Administered Corticosteroid Compositions; Inventors Perrett, Stephen et al., issued as U.S. Pat. No. 10,632,069, 90 pages.

Prosecution history excerpts from U.S. Appl. No. 15/816,154, filed Nov. 17, 2017, for Orally Administered Corticosteroid Compositions; Inventors Perrett, Stephen et al., issued as U.S. Pat. No. 10,632,069, 93 pages.

Prosecution history excerpts from U.S. Appl. No. 17/211,119, filed Mar. 24, 2021, for Corticosteroid Containing Orally Disintegrating Tablet Compositions for Eosinophilic Esophagitis; Inventors Gosselin, Michael A., issued as U.S. Pat. No. 11,260,061, 248 pages.

Prosecution history excerpts from U.S. Appl. No. 17/236,295, filed Apr. 21, 2021, for Orally Administered Corticosteroid Compositions; Inventors Perrett, Stephen et al., issued as U.S. Pat. No. 11,266,598, 65 pages.

Prosecution history from U.S. Appl. No. 15/816,154 ('069 Patent) filed Nov. 17, 2017, for Orally Administered Corticosteroid Compositions; Inventors Perrett, Stephen et al., issued as U.S. Pat. No. 10,632,069, 408 pages.

Prosecution history from U.S. Appl. No. 16/821,464 ('828 Patent) filed Mar. 17, 2020, for Orally Administered Corticosteroid Compositions; Inventors Perrett, Stephen et al., issued as U.S. Pat. No. 11,246,828, 369 pages.

Roeder et al., "Safety and Efficacy of Fluticasone Propionate in the Topical Treatment of Skin Diseases", Skin Pharmacol Physiol (2005); 18 (1): 3-11.

Shukla et al., "Mouth Dissolving Tablets I: An overview of formulation technology," Scientia Pharmaceutica (Mar. 6, 2009); 77(2): 309-326.

Siersema, P.D., "How to Approach a Patient With Refractory or Recurrent Benign Esophageal Stricture". Gastroenterology. Jan. 2019; 156(1): 7-10. Epub Nov. 22, 2018.

Siewert et al., "Eosinophilic gastroenteritis with severe protein-losing enteropathy: Successful treatment with budesonide," Digestive and Liver Disease Jan. 2006; 38(1): 55-59. Epub Dec. 1, 2005.

Svoboda et al., "Oral formulations of budesonide: a novel treatment for inflammatory bowel disease," Drugs of Today (Barc). Nov. 2008; 44(11): 857-863.

Tan et al., "Eosinophilic gastroenteritis treated with non-enteric-coated budesonide tablets," European Journal of Gastroenterology & Hepatology Apr. 2001; 13(4): 425-427.

The United States Pharmacopeia, "701 Disintegration", USP 32 (2009); NF 27, vol. 1, pp. 262-263, 4 pages.

The United States Pharmacopeial Convention, "701 Disintegration", Revision Bulletin, Official Aug. 1, 2008, USP 32 (2009); 3 pages.

U.S. Appl. No. 18/755,113, inventor Meltzer; Brian A, filed Jun. 26, 2024.

U.S. Appl. No. 18/967,539, filed Dec. 3, 2024, by Meltzer et al.

Wood, A.W., "Sucralose", Date of Revision: Aug. 17, 2005, In: Handbook of Pharmaceutical Excipients, 5th Ed. (2006), Raymond C. Rowe, et al. (eds); pp. 742-749, 11 pages.

Sep. 18, 2015 Assignment of U.S. Appl. No. 10/827,106 (which published as Venkatesh, EX1020) to Adare Pharmaceuticals, Inc. recorded at Reel 036554, Frame 0829, 3 pages.

Sep. 18, 2015 Assignment of U.S. Pat. No. 6,139,865 to Adare Pharmaceuticals, Inc. recorded at Reel 036640, Frame 0591, 4 pages.

Apr. 19, 2021 Assignment of U.S. Appl. No. 16/821,464 (which issued as U.S. Pat. No. 11,246,828) from Adare Pharmaceuticals US, L.P. to Ellodi Pharmaceuticals, L.P. recorded at Reel 055966, Frame 0893, 4 pages.

Apr. 19, 2021 Assignment of U.S. Pat. No. 8,771,729 from Adare Pharmaceuticals US, L.P. to Ellodi Pharmaceuticals, L.P. recorded at Reel 055966, Frame 0658, 5 pages.

Apr. 19, 2021 Assignment of U.S. Pat. Nos. 10,632,069, 9,486,407, and 8,771,729 from Adare Pharmaceuticals US, L.P. to Ellodi Pharmaceuticals, L.P. recorded at Reel 055966, Frame 0656, 5 pages.

[Author Unknown] "2.9.5. Uniformity of mass of single-dose preparations", European Pharmacopeia 6.0, 2008; pp. 278-279, 2 pages.

[Author Unknown] "Mission and Preface USP 31-NF 26", The United States Pharmacopeia (USP NF 2008); NF 26, vol. 1, USP 31, pp. v-vii, ix, x, 266-267, 675, 16 pages.

Author Unknown, "Orange Book: Approved Drug Products with Therapeutic Equivalence Evaluations. Patent and Exclusivity for: N213976. Product 001. Budesonide (Eohilia) Suspension 2MG/10ML", Drug Databases (https://www.fda.gov/Drugs/InformationOnDrugs/), date of entry/publication: unknown, [Retrieved from Internet on Sep. 1, 2025 at https://www.accessdata.fda.gov/scripts/cder/ob/patent_info.cfm?Product_No=001&Appl_No=213976&Appl_type=N], 2 pages.

Clarinex® (desloratadine), FDA-approved package insert, Rev Oct. 2005, 21 pages.

Claritin® (loratadine), FDA-approved package insert, Rev. Sep. 2000, 6 pages.

Cordova-Fraga, Teodoro et al., "Effects of anatomical position on esophageal transit time: A biomagnetic diagnostic technique". World J Gastroenterol. Oct. 7, 2008; 14(37): 5707-5711.

Curriculum Vitae of Alan F. Parr, Pharm.D., Ph.D., filed Sep. 19, 2025 in Petition for Post Grant Review of U.S. Pat. No. 12,290,598, filed Sep. 19, 2025, 12 pages.

Declaration of Alan F. Parr, Pharm.D., Ph.D., in Support of Petition for Post Grant Review of U.S. Pat. No. 12,290,598 dated Sep. 19, 2025, filed Sep. 19, 2025, 194 pages.

(56) References Cited

OTHER PUBLICATIONS

Dellon, E.S., et al., "Fluticasone Propionate Orally Disintegrating Tablet (APT-1011) for Eosinophilic Esophagitis: Randomized Controlled Trial", Clin Gastroenterol Hepatol. Nov. 2022; 20(11): 2485-2494.e15. Epub Feb. 16, 2022.

Gennaro, Alfonso R., Remington: The Science and Practice of Pharmacy, 20th Edition (Dec. 2000); vol. 1, Ch. 45, pp. 882-884, 5 pages.

Ghosh and Pfister, "Drug Delivery to the Oral Cavity Molecules to Market". Drugs and the Pharmaceutical Sciences 2005; vol. 145, Ch. 14, pp. 337-355, 26 pages. Epub Feb. 25, 2005.

Eohilia™ (budesonide oral suspension), Highlights of Prescribing Information for Eohilia, Oral suspension: 2 mg/10 mL unit-dose packets, Initial U.S. Approval: 1997, Revised: May 2024, Distributed by: Takeda Pharmaceuticals America, Inc., Lexington, MA 02421, 22 pages.

Inter Partes Review Proceedings No. IPR2024-01197 filed Jul. 22, 2024, *Dr. Falk Pharma GMBH* (Petitioner) vs. *Ellodi Pharmaceuticals LP*, Patent Owner's Objections to Petitioner's Evidence Submitted with Petitioner Reply, U.S. Pat. No. 8,771,729 (U.S. Appl. No. 12/896,005), dated Jul. 21, 2025, 8 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), "Antrum" Definition, American Medical Dictionary: A Concise and Up-to-Date Guide to Medical Terms (1998), Exhibit 2012 filed Apr. 21, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Clinical Trials Study NCT03191864, "Efficacy, Safety, and Pharmacokinetics of APT-1011 in Subjects With Eosinophilic Esophagitis (EoE)(FLUTE)," last updated Apr. 26, 2023, https://clinicaltrials.gov/study/NCT03191864?tab=results&a=11#outcome-measures, Exhibit 2010 filed Apr. 21, 2025, 112 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Corrected Transcript, Oral Hearing Regarding Patent Owner Request for Authorization to File a Motion to Strike, Aug. 14, 2025, 37 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Curriculum Vitae of Martyn Christopher Davies, Exhibit 2008 filed Apr. 21, 2025, 57 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Declaration of Alan F. Parr, Pharm.D., Ph.D., in Support of Petitioner Reply for Inter Partes Review of U.S. Pat. No. 8,771,729, dated Jul. 10, 2025, filed Jul. 14, 2025, 50 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Declaration of Martyn Christopher Davies, Exhibit 2007, dated and filed Apr. 21, 2025, 71 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Deposition of Alan F. Parr, Pharm.D., Ph.D., dated Apr. 9, 2025, Exhibit 2011 filed Apr. 21, 2025, 125 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Deposition of Alan Parr, Pharm.D., Aug. 25, 2025, 103 pages.

Inter Partes Review Proceedings No. IPR2024-01197 filed Jul. 22, 2024, *Dr. Falk Pharma GMBH* (Petitioner) vs. *Ellodi Pharmaceu-*

*ticals LP* (Patent Owner), U.S. Pat. No. 8,771,729 (U.S. Appl. No. 12/896,005), Deposition transcript of Dr. Martyn Christopher Davies, dated Jul. 2, 2025, 246 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Terminal Disclaimer for U.S. Pat. No. 8,771,729, dated Oct. 21, 2025 and filed Oct. 24, 2025, 2 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Judgment: Granting Motion to Terminate and Request for Adverse Judgment after Institution of Trial, dated and filed Oct. 27, 2025, 4 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), M.E. Aulton (Ed.), Pharmaceutics: The Science of Dosage Form Design (2d. 2002), Exhibit 2013 filed Apr. 21, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Order: Granting Patent Owner's Motion Requesting Acceptance of Submission of Patent Owner's Request for Adverse Judgment and Motion to Terminate Filed under Board's Alternative Means, dated and filed Oct. 27, 2025, 4 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Order Related Matters Update, issued Sep. 20, 2025, 6 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Corrected Surreply, dated and filed Sep. 10, 2025, 27 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's email to Request for Authorization to File Motion to Terminate and Request for Adverse Judgement, dated Oct. 23, 2025 and filed Oct. 27, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Motion Requesting Acceptance of Submission of Patent Owner's Request for Adverse Judgment and Motion to Terminate Filed Under Board's Alternative Means, dated and filed Oct. 24, 2025, 5 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Motion to Strike Exhibits 1075-1082, Portions of Petitioner's Reply Brief and Dr. Parr's Reply Declaration, dated and filed Aug. 29, 2025, 10 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Motion To Terminate and Request for Adverse Judgment, dated Oct. 23, 2025 and filed Oct. 24, 2025, 4 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Notice of Deposition of Alan F. Parr, Ph.D. dated Aug. 5, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Request for Oral Hearing dated and filed Sep. 15, 2025, 4 pages.

(56) References Cited

OTHER PUBLICATIONS

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Response dated and filed Apr. 21, 2025, 62 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Updated Exhibit List, dated Oct. 23, 2025 and filed Oct. 24, 2025, 4 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner Dr. Falk Pharma's Demonstrative Exhibits for Oral Hearing, dated Oct. 27, 2025, and filed Oct. 22, 2025, 72 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's email response to Patent Owner's Motion Requesting Acceptance of Submission of Patent Owner's Request for Adverse Judgment and Motion to Terminate filed under Board's Alternative Means, dated and filed Oct. 27, 2025, 2 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Notice of Deposition of Dr. Martyn Christopher Davies, dated and filed Jun. 16, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Opposition to Patent Owner's Motion to Strike dated and filed Sep. 12, 2025, 10 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Reply Brief, dated and filed Jul. 14, 2025, 40 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Request for Oral Argument dated and filed Sep. 15, 2025, 4 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Supplemental Mandatory Notice: Related Matters Section, dated and filed Sep. 23, 2025, 3 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Updated Exhibit List, dated and filed Aug. 26, 2025, 7 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Updated Exhibit List, dated and filed Jul. 14, 2025, 7 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Updated Exhibit List, dated and filed Oct. 22, 2025, 7 pages.

Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), PTAB email response to Request for Authorization to File Motion to Terminate and Request for Adverse Judgement, dated Oct. 23, 2025, 2 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 10,632,069 (U.S. Appl. No. 15/816,154), Patent Owner's Notice of Deposition of Alan F. Parr, Ph.D. dated Aug. 5, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Oct. 23, 2024 Transcript of Oral Hearing Dismissing Complaint, *Ellodi Pharmaceuticals, L.P.* v. *Dr. Falk Pharma*, Case No. 24-cv01392-PTG (E.D. Va), dated Oct. 23, 2024 and filed Dec. 10, 2025, 23 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Comment of the United States Federal Trade Commission, Terminal Disclaimer Practice to Obvoiusate Nonstatutory Double Patenting, PTO-P-2024-0003, dated Jul. 9, 2024 and filed Dec. 10, 2025, 8 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Curriculum Vitae of Martyn Christopher Davies CBE DSc FRPharmS CChem FRSC, filed Sep. 9, 2025, 57 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Decision Granting Institution of Inter Partes Review U.S.C. § 314 dated Jun. 3, 2025, 18 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Declaration of Alan F. Parr, Pharm.D, Ph.D., in Support of Petitioner Replies for Inter Partes Review, dated Dec. 9, 2025 and filed Dec. 10, 2025, 80 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Declaration of Isha Agarwal Pursuant to 37 CFR § 42.10(c)(2), dated and filed Aug. 8, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Declaration of Martyn Christopher Davies, dated and filed Sep. 9, 2025, 72 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Deposition Trancript of Dr. Martyn Davies, dated Nov. 19, 2025, and filed Dec. 10, 2025, 170 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Exhibit 1114, Reporter's Remote Transcript of Proceedings, dated Nov. 3, 2025 and filed Nov. 19, 2025, 32 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Joint Stipulation to Modify Due Dates 2-3, dated and filed Nov. 12, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Judgment Against Ellodi in *Ellodi Pharmaceuticals, L.P.* v. *Dr. Falk Pharma GmbH*, Case No. 4b O 43/24, Regional Court of Dusseldorf, Germany (Feb. 27, 2025)—Certified English Language Translation, dated Feb. 27, 2025 and filed Dec. 10, 2025, 23 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Judgment Against Ellodi in *Ellodi Pharmaceuti-*

(56)　　　　　References Cited

OTHER PUBLICATIONS

*cals, L.P.* v. *Dr. Falk Pharma GmbH*, Case No. 4b O 43/24, Regional Court of Dusseldorf, Germany (Feb. 27, 2025)—Original German Language, dated Feb. 27, 2025 and filed Dec. 10, 2025, 22 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Order Related Matters Update, issued Sep. 20, 2025, 6 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Exhibit List, dated and filed Aug. 22, 2025, 4 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Notice of Intent to Designate a Provisionally Recognized PTAB Attorney as Back-Up Counsel Pursuant to 37 CFR § 42.10(c)(2), dated and filed Aug. 8, 2025, 4 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Objections Pursuant to 37 C.F.R. § 42.64(b)(1) dated and filed Jun. 17, 2025, 14 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Opposition to Petitioner's Motion for Additional Discovery, filed Nov. 3, 2025, 8 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Response, dated and filed Sep. 9, 2025, 64 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Patent Owner's Updated Mandatory Notices, dated and filed Aug. 22, 2025, 4 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Motion for Additional Discovery, filed Oct. 27, 2025, 8 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Notice of Deposition of Dr. Martyn Christopher Davies, dated and filed Oct. 24, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Objections to Admissibility of Patent Owner's Evidence, dated and filed Sep. 16, 2025, 6 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Reply Brief, dated and filed Dec. 10, 2025, 40 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Reply Brief, dated and filed Dec. 10, 2025, 45 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl.

No. 15/816,154), Petitioner's Revised Notice of Deposition of Dr. Martyn Christopher Davies, dated and filed Nov. 12, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Supplemental Mandatory Notice: Related Matters Section, dated and filed Sep. 23, 2025, 3 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Updated Exhibit List, dated and filed Dec. 10, 2025, 9 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Updated Exhibit List, dated and filed Nov. 19, 2025, 6 pages.

Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Updated Mandatory Notice, dated and filed Sep. 30, 2025, 3 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Curriculum Vitae of Martyn Christopher Davies CBE DSc FRPharmS CChem FRSC, filed Sep. 9, 2025, 57 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Decision Granting Institution of Inter Partes Review U.S.C. § 314 dated Jun. 3, 2025, 18 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Declaration of Isha Agarwal Pursuant to 37 CFR § 42.10(c)(2), dated and filed Aug. 8, 2025, 3 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Declaration of Martyn Christopher Davies, dated and filed Sep. 9, 2025, 70 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Exhibit 1114, Reporter's Remote Transcript of Proceedings, dated Nov. 3, 2025 and filed Nov. 19, 2025, 32 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Exhibit 3001, PTAB email response regarding Petitioner's motion for additional discovery re Lee Report (Exhibit 2029), dated Nov. 20, 2025, 3 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Joint Stipulation to Modify Due Dates 2-3, dated and filed Nov. 12, 2025, 3 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Order—Conduct of the Proceeding; Extending Word Limit for Reply and Sur-Reply 37 C.F.R. § 42.5(a), filed Nov. 4, 2025, 4 pages.

Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Order Related Matters Update, issued Sep. 20, 2025, 6 pages.

Inter Partes Review Proceedings No. IPR2025-00054 filed Oct. 24, 2024, *Dr. Falk Pharma GMBH* (Petitioner) vs. *Ellodi Pharmaceu-*

(56) References Cited

OTHER PUBLICATIONS ticals L.P. (Patent Owner), U.S. Pat. No. 11,246,828 (U.S. Appl. No. 16/821,464), Patent Owner's Exhibit List, dated and filed Aug. 8, 2025, 3 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Notice of Deposition of Alan F. Parr, Ph.D. dated Aug. 5, 2025, 3 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Notice of Intent to Designate a Provisionally Recognized PTAB Attorney as Back-Up Counsel Pursuant to 37 CFR § 42.10(c)(2), dated and filed Aug. 8, 2025, 4 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Objections Pursuant to 37 C.F.R. § 42.64(b)(1) dated and filed Jun. 17, 2025, 15 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Opposition to Petitioner's Motion for Additional Discovery, filed Nov. 3, 2025, 8 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Response, dated and filed Sep. 9, 2025, 67 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Patent Owner's Updated Mandatory Notices, dated and filed Aug. 22, 2025, 4 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Motion for Additional Discovery, filed Oct. 27, 2025, 8 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Notice of Deposition of Dr. Martyn Christopher Davies, dated and filed Oct. 24, 2025, 3 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Objections to Admissibility of Patent Owner's Evidence, dated and filed Sep. 16, 2025, 6 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Reply Brief, dated and filed Dec. 10, 2025, 45 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Revised Notice of Deposition of Dr. Martyn Christopher Davies, dated and filed Nov. 12, 2025, 3 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Supplemental Mandatory Notice: Related Matters Section, dated and filed Sep. 23, 2025, 3 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Updated Exhibit List, filed Dec. 10, 2025, 9 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Updated Exhibit List, filed Nov. 19, 2025, 7 pages.

Inter Partes Review Proceedings No. IPR2025-00054 filed Oct. 24, 2024, Dr. Falk Pharma GMBH (Petitioner) vs. Ellodi Pharmaceuticals L.P. (Patent Owner), U.S. Pat. No. 11,246,828 (U.S. Appl. No. 16/821,464), Petitioner's Updated Mandatory Notice, dated and filed Sep. 30, 2025, 3 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Curriculum Vitae of Martyn Christopher Davies CBE DSc FRPharmS CChem FRSC, filed Sep. 9, 2025, 57 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Decision Granting Institution of Inter Partes Review U.S.C. § 314 dated Jun. 3, 2025, 12 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Declaration of Isha Agarwal Pursuant to 37 CFR § 42.10(c)(2), dated and filed Aug. 8, 2025, 3 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Declaration of Martyn Christopher Davies, dated and filed Sep. 9, 2025, 83 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Order Related Matters Updates issued Sep. 20, 2025, 6 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Exhibit List, dated and filed Aug. 8, 2025, 3 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Notice of Deposition of Alan F. Parr, Ph.D. dated Aug. 5, 2025, 3 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Notice of Intent to Designate a Provisionally Recognized PTAB Attorney as Back-Up Counsel Pursuant to 37 CFR § 42.10(c)(2), dated and filed Aug. 8, 2025, 4 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Objections Pursuant to 37 C.F.R. § 42.64(b)(1) dated and filed Jun. 17, 2025, 15 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Response dated and filed Sep. 9, 2025, 65 pages.

Inter Partes Review Proceedings No. IPR2025-00055 filed Oct. 24, 2024, Dr. Falk Pharma GMBH (Petitioner) vs. Ellodi Pharmaceuticals L.P. (Patent Owner), Petition for Inter Partes Review of U.S. Pat. No. 9,486,407 (U.S. Appl. No. 14/294,660), Patent Owner's Updated Mandatory Notices, dated and filed Aug. 22, 2025, 4 pages.

(56)            References Cited

OTHER PUBLICATIONS

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Notice of Deposition of Dr. Martyn Christopher Davies, dated and filed Oct. 24, 2025, 3 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Objections to Admissibility of Patent Owner's Evidence, dated and filed Sep. 16, 2025, 5 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Reply Brief, dated and filed Dec. 10, 2025, 46 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Revised Notice of Deposition of Dr. Martyn Christopher Davies, dated and filed Nov. 12, 2025, 3 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Supplemental Mandatory Notice: Related Matters Section dated and filed Dec. 17, 2024, 3 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Updated Exhibit List, dated and filed Dec. 10, 2025, 10 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Updated Exhibit List, dated and filed Nov. 19, 2025, 7 pages.

Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Updated Mandatory Notice, dated and filed Sep. 30, 2025, 3 pages.

Inter Partes Review Proceedings No. IPR2025-00056 filed Oct. 24, 2024, *Dr. Falk Pharma GMBH* (Petitioner) vs. *Ellodi Pharmaceuticals L.P.* Patent Owner's, Surreply dated and filed May 7, 2025, 10 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Decision Granting Institution of Inter Partes Review U.S.C. § 314 dated Jun. 3, 2025, 46 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Declaration of Isha Agarwal Pursuant to 37 CFR § 42.10(c)(2), dated and filed Aug. 8, 2025, 3 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Order Related Matters Update, issued Sep. 20, 2025, 6 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Patent Owner's Notice of Deposition of Alan F. Parr, Ph.D. dated Aug. 5, 2025, 3 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Patent Owner's Notice of Intent to Designate a Provisionally Recognized PTAB Attorney as Back-Up Counsel Pursuant to 37 CFR § 42.10(c)(2), dated and filed Aug. 8, 2025, 4 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Patent Owner's Objections Pursuant to 37 C.F.R. § 42.64(b)(1) dated and filed Jun. 17, 2025, 15 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Patent Owner's Updated Exhibit List, dated and filed Aug. 8, 2025, 3 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Patent Owner's Updated Mandatory Notices, dated and filed Aug. 22, 2025, 4 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Petitioner's Supplemental Mandatory Notice: Related Matters Section, dated and filed Sep. 23, 2025, 3 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Petitioner's Updated Exhibit List dated and filed Nov. 19, 2025, 7 pages.

Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Reporter's Remote Transcript of Proceedings, dated Nov. 3, 2025 and filed Nov. 19, 2025, 32 pages.

Inter Partes Review Proceedings No. IPR2025-00056 filed Oct. 24, 2024, *Dr. Falk Pharma GMBH* (Petitioner) vs. *Ellodi Pharmaceuticals L.P.* Petitioner's Reply to Patent Owner's Preliminary Response dated and filed Apr. 23, 2025, 10 pages.

Inter Partes Review Proceedings Nos. IPR2025-00052 (U.S. Pat. No. 10,632,069), IPR2025-00054 (U.S. Pat. No. 11,246,828) and IPR2025-00055 (U.S. Pat. No. 9,486,407), filed by *Dr. Falk Pharma GMBH* (Petitioner) vs. *Ellodi Pharmaceuticals L.P.* (Patent Owner), Deposition of Alan F. Parr, Pharm.D., Ph.D., Aug. 29, 2025, 30 pages.

PCT Application No. PCT/US2024/059722, International Search Report and Written Opinion mailed Apr. 17, 2025, Applicant Ellodi Pharmaceuticals, L.P.; 13 pages.

Iorgulescu, "Saliva between normal and pathological. Important factors in determining systemic and oral health," Journal of Medicine and Life. Jul.-Sep. 2009; 2(3):303-307.

Jorveza (budesonide) 0.5 mg orodispersible tablets, 1 mg orodispersible tablets; Summary of Product Characteristics, Labelling and Package Leaflet, Marketing Authorisation Nos. 1 mg EU/1/17/1254/001, EU/1/17/1254/002, EU/1/17/1254/003, EU/1/17/1254/004, EU/1/17/1254/005, EU/1/17/1254/006; Marketing Authorisation Nos. 0.5 mg EU/1/17/1254/007, EU/1/17/1254/008, EU/1/17/1254/009, EU/1/17/1254/010, EU/1/17/1254/011; Date of first authorisation: Jan. 8, 2018; Date of latest renewal: Sep. 27, 2022; Dr. Falk Pharma GmbH, Germany; 31 pages.

Khan et al., "Taste masking of ondansetron hydrochloride by polymer carrier system and formulation of rapid-disintegrating tablets," AAPS PharmSciTech. Jun. 22, 2007; 8(2): Article 46, E1-E7.

Lee, Beom-Jin, "Pharmaceutical Preformulation: Physicochemical Properties of Excipients and Powders and Tablet Characterization", edited by Shayne Cox Gad, Pharmaceutical Manufacturing Handbook: Production and Processes, John Wiley & Sons (2008—Month Unknown); Ch. 6.1, pp. 881-931, 51 pages.

(56) References Cited

OTHER PUBLICATIONS

Narmada et al., "Formulation, evaluation and optimization of fast dissolving tablets containing amlodipine besylate by sublimation method," ARS Pharmaceutica. 2009 (Month Unknown); 50(3): 129-144.

Pepcid® (famotidine), FDA-approved package insert, Issued 2001 (Month Unknown); 12 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), Petition for Post Grant Review of U.S. Pat. No. 12,290,598 (U.S. Appl. No. 17/569,047), dated and filed Sep. 18, 2025, and Petitioner's Power of Attorney dated Sep. 18, 2025, 118 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Declaration of Isha Agarwal in Support of Motion for Pro Hac Vice Admission, filed Jan. 7, 2026, 2 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Declaration of Martyn Christopher Davies, dated and filed Dec. 26, 2025, 99 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Notice of Filing Date Accorded to Petition and Time for Filing Patent Owner Preliminary Response, mailed Sep. 26, 2025, 10 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Order: Conduct of Proceeding, dated and filed Dec. 18, 2025, 3 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Patent Owner's Brief in Support of Discretionary Denial, dated and filed Nov. 24, 2025, 26 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Patent Owner's Mandatory Notices dated and filed Oct. 10, 2025, 4 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Patent Owner's Power of Attorney dated and filed Oct. 10, 2025, 3 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Patent Owner's Preliminary Response, dated and filed Dec. 26, 2025, 91 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Patent Owner's Updated Exhibit List, dated and filed Jan. 7, 2026, 6 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Petitioner's email to the Director regarding Patent Owner's unauthorized request for Certificate of Correction, *Dr. Falk Pharma GmbH* v. *Ellodi Pharmaceuticals, L.P.*, dated Nov. 18, 2025, 3 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl.

No. 17/569,047), Petitioner's Opposition to Patent Owner's Request for Discretionary Denial, dated and filed Dec. 29, 2025, 34 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Petitioner's Updated Exhibit List, dated and filed Dec. 29, 2025, 9 pages.

Post Grant Review Proceedings No. PGR2025-00086 filed Sep. 19, 2025, *Dr. Falk Pharma GMBH* (Petitioner) vs. *Ellodi Pharmaceuticals, L.P.* (Patent Owner), U.S. Pat. No. 12,290,598 (U.S. Appl. No. 17/569,047), Request for Certificate of Correction, dated Oct. 14, 2025 and filed Nov. 24, 2025, 8 pages.

Prosecution history excerpts from U.S. Appl. No. 14/294,660, filed Jun. 3, 2014, for Orally Administered Corticosteroid Compositions; Inventors Perrett, Stephen et al., issued as U.S. Pat. No. 9,486,407, 139 pages.

Prosecution history excerpts from U.S. Appl. No. 17/569,047, filed Jan. 5, 2022, 439 pages.

Schoepfer et al., "Variation in Endoscopic Activity Assessment and Endoscopy Score Validation in Adults With Eosinophilic Esophagitis," Clinical Gastroenterology and Hepatology. Jul. 2019; 17(8): 1477-1488.e10. Epub Nov. 23, 2018.

Seitz and Flessland, "Evaluation of the Physical Properties of Compressed Tablets I: Tablet Hardness and Friability Author links open overlay panel", J Pharm Sci. Sep. 1965; 54(9): 1353-1357.

Sheskey, Paul J. Sheskey et al., (eds.), Handbook of Pharmaceutical Excipients (8d. 2017—Month Unknown); pp. 191-193, 476-480, 10 pages.

Sonnergaard et al., "Comparative Investigations of Tablet Crushing Force Testers," Pharm. Ind., 2005 (Month Unknown); 67, Nr. 1:109-115.

Stewart, Memorandum from Director Coke Morgan Stewart to Members of the PTAB, dated Jul. 31, 2025, 3 pages.

Than, "Individualized Drugs for Individual Needs", Review of Optometry. Jan. 16, 2009; 146: 38-43, 5 pages.

The American Heritage Dictionary of the English Language, 4th ed., Sep. 2000—Definitions of "disintegrate" and "dissolve".

U.S. Appl. No. 12/896,005, filed Oct. 1, 2010, 42 pages.

U.S. Appl. No. 14/311,732, filed Jun. 23, 2014, 43 pages.

U.S. Appl. No. 15/205,390, filed Jul. 8, 2016, inventor Perrett, Stephen, 50 pages.

U.S. Appl. No. 15/816,154, filed Nov. 17, 2017, inventor Perrett, Stephen, 53 pages.

U.S. Appl. No. 16/821,464, filed Mar. 17, 2020, inventor Perrett, Stephen, 48 pages.

U.S. Appl. No. 17/569,047, filed Jan. 5, 2022, inventor Perrett, Stephen, 45 pages.

U.S. Appl. No. 19/403,672, filed Nov. 28, 2025; Inventor Perrett, Stephen et al.

U.S. Appl. No. 19/403,674, filed Nov. 28, 2025; Inventor Gosselin, Michael A. et al.

U.S. Federal Trade Commission (FTC)—To Promote Innovation: The Proper Balance of Competition and Patent Law and Policy, Oct. 2003 Report, Chapter 4: Competition Perspectives on Substantive Standards of Patentability, 54 pages.

U.S. Appl. No. 19/170,231, filed Apr. 4, 2025, inventor Perrett, Stephen, et al.

U.S. Appl. No. 61/247,642 as filed on Oct. 1, 2009, 40 pages.

USP 1151 Pharmaceutical Dosage Forms, Pharmacopeial Forum, vol. 35(5) [Sep.-Oct. 2009], 1260-1310, 51 pages.

Van Rhijn et al., "Histological Response to Fluticasone Propionate in Patients with Eosinophilic Esophagitis Is Associated with Improved Functional Esophageal Mucosal Integrity". Am J Gastroenterol. Sep. 2015; 110(9): 1289-1297. Epub Aug. 25, 2015.

Worthen, Dennid B. (ed.) "Lozenge" Definition, Dictionary of Pharmacy (Jul. 2004); 9 pages.

Zofran® (ondansetron), FDA-approved package insert, May 2004, RL-2082, 17 pages.

Inter Partes Review Proceedings No. IPR2025-00052 filed Oct. 24, 2024, *Dr. Falk Pharma GMBH (Petitioner)* vs. *Ellodi Pharmaceuticals L.P. (Patent Owner)*, U.S. Pat. No. 10,632,069 (U.S. Appl. No. 15/816,154), Disclaimer for U.S. Pat. No. 10,632,069, dated Jan. 12, 2026 and filed Jan. 20, 2026, 2 pages.

(56) References Cited

OTHER PUBLICATIONS

Inter Partes Review Proceedings No. IPR2025-00052 filed Oct. 24, 2024, *Dr. Falk Pharma GMBH (Petitioner)* vs. *Ellodi Pharmaceuticals L.P. (Patent Owner)*, U.S. Pat. No. 10,632,069 (U.S. Application No. 15/816, 154), Judgement: Granting Patent Owner's Unopposed Motion to Terminate and Request for Adverse Judgment After Institution of Trial, dated and filed Jan. 23, 2026, 4 pages.

Inter Partes Review Proceedings No. IPR2025-00052 filed Oct. 24, 2024, *Dr. Falk Pharma GMBH (Petitioner)* vs. *Ellodi Pharmaceuticals L.P. (Patent Owner)*, U.S. Pat. No. 10,632,069 (U.S. Appl. No. 15/816,154), Patent Owner's Motion to Terminate and Request for Adverse Judgment, dated and filed Jan. 20, 2026, 4 pages.

Inter Partes Review Proceedings No. IPR2025-00052 filed Oct. 24, 2024, *Dr. Falk Pharma GMBH (Petitioner)* vs. *Ellodi Pharmaceuticals L.P. (Patent Owner)*, U.S. Pat. No. 10,632,069 (U.S. Appl. No. 15/816,154), Patent Owner's Updated Exhibit List, dated and filed Jan. 20, 2026, 5 pages.

Inter Partes Review Proceedings No. IPR2025-00052 filed Oct. 24, 2024, *Dr. Falk Pharma GMBH (Petitioner)* vs. *Ellodi Pharmaceuticals L.P. (Patent Owner)*, U.S. Pat. No. 10,632,069 (U.S. Appl. No. 15/816,154), Petitioner's Request for Oral Argument, dated and filed Jan. 20, 2026, 4 pages.

Inter Partes Review Proceedings No. IPR2025-00054 filed Oct. 24, 2024, *Dr. Falk Pharma GMBH (Petitioner)* vs. *Ellodi Pharmaceuticals L.P. (Patent Owner)*, U.S. Pat. No. 11,246,828 (U.S. Appl. No. 16/821,464), Disclaimer for U.S. Pat. No. 11,246,828, dated Jan. 12, 2026 and filed Jan. 20, 2026, 2 pages.

Inter Partes Review Proceedings No. IPR2025-00054 filed Oct. 24, 2024,*Dr. Falk Pharma GMBH (Petitioner)* vs. *Ellodi Pharmaceuticals L.P. (Patent Owner)*, U.S. Pat. No. 11,246,828 (U.S. Appl. No. 16/821,464), Judgement: Granting Patent Owner's Unopposed Motion to Terminate and Request for Adverse Judgment After Institution of Trial, dated and filed Jan. 23, 2026, 4 pages.

Inter Partes Review Proceedings No. IPR2025-00054 filed Oct. 24, 2024, *Dr. Falk Pharma GMBH (Petitioner)* vs. *Ellodi Pharmaceuticals L.P. (Patent Owner)*, U.S. Pat. No. 11,246,828 (U.S. Appl. No. 16/821,464), Patent Owner's Motion to Terminate and Request for Adverse Judgment, dated and filed Jan. 20, 2026, 4 pages.

Inter Partes Review Proceedings No. IPR2025-00054 filed Oct. 24, 2024, *Dr. Falk Pharma GMBH (Petitioner)* vs. *Ellodi Pharmaceuticals L.P. (Patent Owner)*, U.S. Pat. No. 11,246,828 (U.S. Appl. No. 16/821,464), Patent Owner's Updated Exhibit List, dated and filed Jan. 20, 2026, 5 pages.

Inter Partes Review Proceedings No. IPR2025-00054 filed Oct. 24, 2024, *Dr. Falk Pharma GMBH (Petitioner)* vs. *Ellodi Pharmaceuticals L.P. (Patent Owner)*, U.S. Pat. No. 11,246,828 (U.S. Appl. No. 16/821,464), Petitioner's Request for Oral Argument, dated and filed Jan. 20, 2026, 4 pages.

Inter Partes Review Proceedings No. IPR2025-00055 filed Oct. 24, 2024, *Dr. Falk Pharma GMBH (Petitioner)* vs. *Ellodi Pharmaceuticals L.P. (Patent Owner)*, Petition for Inter Partes Review of U.S. Pat. No. 9,486,407 (U.S. Appl. No. 14/294,660), Decision Granting Patent Owner's Motion to Terminate and Request for Adverse Judgment After Institution of Trial, dated and filed Jan. 26, 2026, 4 pages.

Inter Partes Review Proceedings No. IPR2025-00055 filed Oct. 24, 2024, *Dr. Falk Pharma GMBH (Petitioner)* vs. *Ellodi Pharmaceuticals L.P. (Patent Owner)*, Petition for Inter Partes Review of U.S. Pat. No. 9,486,407 (U.S. Appl. No. 14/294,660), Disclaimer for U.S. Pat. No. 9,486,407, dated Jan. 12, 2026 and filed Jan. 20, 2026, 2 pages.

Inter Partes Review Proceedings No. IPR2025-00055 filed Oct. 24, 2024, *Dr. Falk Pharma GMBH (Petitioner)* vs. *Ellodi Pharmaceuticals L.P. (Patent Owner)*, Petition for Inter Partes Review of U.S. Pat. No. 9,486,407 (U.S. Appl. No. 14/294,660), Patent Owner's Motion to Terminate and Request for Adverse Judgment, dated and filed Jan. 20, 2026, 4 pages.

Inter Partes Review Proceedings No. IPR2025-00055 filed Oct. 24, 2024, *Dr. Falk Pharma GMBH (Petitioner)* vs. *Ellodi Pharmaceuticals L.P. (Patent Owner)*, Petition for Inter Partes Review of U.S.

Pat. No. 9,486,407 (U.S. Appl. No. 14/294,660), Patent Owner's Updated Exhibit List, dated and filed Jan. 20, 2026, 5 pages.

Inter Partes Review Proceedings No. IPR2025-00055 filed Oct. 24, 2024, *Dr. Falk Pharma GMBH (Petitioner)* vs. *Ellodi Pharmaceuticals L.P. (Patent Owner)*, Petition for Inter Partes Review of U.S. Pat. No. 9,486,407 (U.S. Appl. No. 14/294,660), Petitioner's Request for Oral Argument, dated and filed Jan. 20, 2026, 4 pages.

Inter Partes Review Proceedings No. IPR2025-00056 filed Oct. 24, 2024, *Dr. Falk Pharma GMBH (Petitioner)* vs. *Ellodi Pharmaceuticals L.P. (Patent Owner)*, U.S. Pat. No. 11,260,061 (U.S. Appl. No. 17/211,119), Disclaimer for U.S. Pat. No. 11,260,061, dated Jan. 12, 2026 and filed Jan. 20, 2026, 2 pages.

Inter Partes Review Proceedings No. IPR2025-00056 filed Oct. 24, 2024, *Dr. Falk Pharma GMBH (Petitioner)* vs. *Ellodi Pharmaceuticals L.P. (Patent Owner)*, U.S. Pat. No. 11,260,061 (U.S. Appl. No. 17/211,119), Judgement: Granting Patent Owner's Unopposed Motion to Terminate and Request for Adverse Judgment After Institution of Trial, dated and filed Jan. 23, 2026, 4 pages.

Inter Partes Review Proceedings No. IPR2025-00056 filed Oct. 24, 2024, *Dr. Falk Pharma GMBH (Petitioner)* vs. *Ellodi Pharmaceuticals L.P. (Patent Owner)*, U.S. Pat. No. 11,260,061 (U.S. Appl. No. 17/211,119), Patent Owner's Motion to Terminate and Request for Adverse Judgment, dated and filed Jan. 20, 2026, 4 pages.

Inter Partes Review Proceedings No. IPR2025-00056 filed Oct. 24, 2024, *Dr. Falk Pharma GMBH (Petitioner)* vs. *Ellodi Pharmaceuticals L.P. (Patent Owner)*, U.S. Pat. No. 11,260,061 (U.S. Appl. No. 17/211,119), Patent Owner's Updated Exhibit List, dated and filed Jan. 20, 2026, 3 pages.

Inter Partes Review Proceedings No. IPR2025-00056 filed Oct. 24, 2024, *Dr. Falk Pharma GMBH (Petitioner)* vs. *Ellodi Pharmaceuticals L.P. (Patent Owner)*, U.S. Pat. No. 11,260,061 (U.S. Appl. No. 17/211,119), Petitioner's Request for Oral Argument, dated and filed Jan. 20, 2026, 4 pages.

IPR2025-00052, Patent 10,632,069 B2, IPR2025-00054, Patent 11,246,828 B2, IPR2025-00055, U.S. Pat. No. 9,486,407 B2 IPR2025-00056, U.S. Pat. No. 11,260,061 B2, Order Conduct of the Proceeding Authorizing Patent Owner's Motion to Terminate 37 C.F.R. § 42.5(a), dated Jan. 13, 2026, 3 pages.

IPR2025-00052, U.S. Pat. No. 10,632,069 B2, IPR2025-00054, U.S. Pat. No. 11,246,828 B2, IPR2025-00055, U.S. Pat. No. 9,486,407 B2 IPR2025-00056, U.S. Pat. No. 11,260,061 B2, PGR2025-00086, U.S. Pat. No. 12,290,598, PTAB email response to Counsel "Petitioner is authorized to file the adverse judgments as exhibits in PGR2025-00086.", dated Jan. 29, 2026, 2 pages.

Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Notice of Decisions on Institution, dated and filed Jan. 27, 2026, 2 pages.

Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Patent Owner's Notice of Intent To Designate a Provisionally Recognized Ptab Attorney as Back-Up Counsel Pursuant To 37 C.F.R. § 42.10(c)(2), dated and filed Jan. 7, 2026, 4 pages.

Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Patent Owner's Updated Exhibit List, dated and filed Jan. 19, 2026, 6 pages.

Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Patent Owners Surreply, dated and filed Jan. 19, 2026, 8 pages.

Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Petitioner's Reply To Patent Owner's Preliminary Response, dated and filed Jan. 13, 2026, 10 pages.

Post Grant Review Proceedings No. PGR2025-00086 filed Sep. 19, 2025, *Dr. Falk Pharma GMBH (Petitioner)* vs. *Ellodi Pharmaceu-*

(56) References Cited

OTHER PUBLICATIONS

*ticals, L.P. (Patent Owner)*, U.S. Pat. No. 12,290,598 (U.S. Appl. No. 17/569,047), Petitioner's Sur-Reply To Patent Owner's Discretionary Denial Brief, dated and filed Jan. 13, 2026, 9 pages.
Post Grant Review Proceedings No. PGR2025-00086 filed Sep. 19, 2025, *Dr. Falk Pharma GMBH (Petitioner)* vs. *Ellodi Pharmaceuticals, L.P. (Patent Owner)*, U.S. Pat. No. 12,290,598 (U.S. Appl. No. 17/569,047), Petitioner's Updated Exhibit List, dated and filed Jan. 29, 2026, 9 pages.
U.S. Pat. No. 10,632,069 (U.S. Appl. No. 15/816,154), Statutory Disclaimer for U.S. Pat. No. 10,632,069, dated Jan. 12, 2026, and filed Jan. 12, 2026, 2 pages.
U.S. Pat. No. 11,246,828 (U.S. Appl. No. 16/821,464), Statutory Disclaimer for U.S. Pat. No. 11,246,828, dated Jan. 12, 2026, and filed Jan. 12, 2026, 2 pages.
U.S. Pat. No. 11,260,061 (U.S. Appl. No. 17/211,119), Statutory Disclaimer for U.S. Pat. No. 11,260,061, dated Jan. 12, 2026, and filed Jan. 12, 2026, 2 pages.
U.S. Pat. No. 8,771,729 (U.S. Appl. No. 12/896,005), Statutory Disclaimer for U.S. Pat. No. 8,771,729, dated Oct. 21, 2025, and filed Oct. 21, 2025, 2 pages.
U.S. Pat. No. 9,486,407 (U.S. Appl. No. 14/294,660), Statutory Disclaimer for U.S. Pat. No. 9,486,407, dated Jan. 12, 2026, and filed Jan. 12, 2026, 2 pages.

Abbreviations: BID = twice daily; EGD = esophagogastroduodenoscopy; EREFs = Eosinophilic Esophagitis Endoscopic Reference Score; HPF = high-power field; HS = hora somni (before sleep); N = number; PGI-C = Patient Global Impression of Change; PGI-S = Patient Global Impression of Severity; PRO = patient reported outcome; Wk = Week.

Fig. 2

Week 52 Responder Rate (%)

Week 26 Responder Rate (%)

Mean Number of Dysphagia Episodes by Study Week

Fig. 8

Mean Global EoE Scores by Study Week

Treatment
APT-1011 1.5 mg BID
APT-1011 1.5 mg HS
APT-1011 3 mg BID
APT-1011 3 mg HS
Placebo

METHODS OF TREATING EOSINOPHILIC ESOPHAGITIS AND REDUCING CANDIDIASIS

CROSS-REFERENCE TO RELATED APPLICATIONS

This application is the U.S. National Stage Application of International Patent Application No. PCT/US2020/053778, filed on Oct. 1, 2020, which claims the benefit of priority to U.S. Provisional Application No. 62/908,697, filed on Oct. 1, 2019, and U.S. Provisional Application No. 63/072,380, filed on Aug. 31, 2020, the entire contents of each of which are hereby incorporated by reference in their entirety.

BACKGROUND

Eosinophilic oesophagitis (EoE) is a chronic destructive immune-mediated inflammatory disease of the oesophagus, characterized clinically by oesophageal dysfunction and histologically by eosinophilic infiltration. Patients with EoE present with symptoms of difficulty swallowing (dysphagia), chest pain, persistent heartburn, upper abdominal pain, and food getting stuck in the esophagus after swallowing (impaction). The current treatments for EoE include dietary modifications, proton pump inhibitors, and corticosteroids.

Corticosteroids are the most helpful therapy for the control of EoE, because of their efficacy at controlling inflammation. However, the immunosuppressive properties of corticosteroids, which contribute to their efficacy, result in an increased risk of infections. The most common infections associated with long term corticosteroid use in EoE patients are fungal infections, including oral, oropharyngeal, and oesophageal candidiasis.

There exists a need in the art for methods of effectively treating EoE with corticosteroids while also controlling the side effects associated with corticosteroids, such as fungal infections, including oral, oropharyngeal, and oesophageal candidiasis. The present disclosure addresses these needs.

SUMMARY OF THE INVENTION

The present disclosure provides methods for reducing the side effects associated with oral corticosteroid administration.

In some embodiments, the disclosure provides a method of treating eosinophilic esophagitis (EoE) in a patient in need thereof comprising orally administering to the patient about 0.5 mg to about 5 mg of fluticasone propionate, or an equipotent dose of a corticosteroid, once daily for at least 12 weeks, wherein during said 12 weeks: the patient's risk of candidiasis is less than about 10%, and the patient shows an improvement in at least one of the following outcomes compared to a patient that is administered the corticosteroid twice daily: (i) at least one symptom score measured using a patient reported outcome symptom evaluation (PROSE) instrument after an episode of dysphagia; (ii) EoE Endoscopic Reference (EREF) score; (iii) EoE Activity Index (EEsAI) avoidance, modification, and slow swallowing (AMS) score: (vi) Global EoE score; (v) Patient global impression of severity (PGIS); and (vi) patient global impression of change (PGIC).

In some embodiments, the symptom score is one or more of: (i) number of dysphagia free days over a 14 day period; (ii) the average daily episode severity score over a 14 day period; or (iii) the symptom burden over a 14 day period. In some embodiments, the symptom score is the number of dysphagia episodes over 14 days.

In some embodiments, the total daily dose for the twice daily administration and the once daily administration are the same. In some embodiments, the total daily dose for twice daily administering is more than the total daily dose for the once daily administration.

In some embodiments, after treating according to the methods of the disclosure, the patient shows an improvement in at least one of the following outcomes compared to a patient that is administered the corticosteroid twice daily: i. at least one symptom score measured using a patient reported outcome symptom evaluation (PROSE) instrument after an episode of dysphagia; ii. EoE Endoscopic Reference (EREFS) score; or iii. Global EoE score.

In some embodiments, the methods of the disclosure comprise administering 1.5 mg or 3.0 mg of fluticasone propionate, or an equipotent dose of a corticosteroid. In some embodiments, 3.0 mg of fluticasone propionate, or an equipotent dose of a corticosteroid is administered.

In some embodiments, fluticasone propionate or the corticosteroid is administered at bedtime or at nighttime.

In some embodiments, fluticasone propionate or the equipotent dose of the corticosteroid is administered while the patient is lying down or immediately prior to the patient lying down.

In some embodiments, the method of the disclosure reduces the patient's risk of candidiasis to 5% or less. In some embodiments, the candidiasis is oral candidiasis or esophageal candidiasis. In some embodiments, the patient's risk of oral candidiasis is less than about 10%. In some embodiments, the patient's risk of oral candidiasis is less than about 4%, less than about 3%, less than about 2%, or less than about 1%. In some embodiments, according to the methods of the disclosure, a patient's risk of oral candidiasis is about 4.8%.

In some embodiments, the patient's risk of esophageal candidiasis is less than about 10%. In some embodiments, the patient's risk of esophageal candidiasis is about 9% or less, about 8% or less, about 7% or less, about 6% or less, or about 5% or less.

In some embodiments, the methods of the disclosure comprise utilizing a symptom score, wherein the symptom score comprises: (i) on a scale ranging from 0 to 10, a difficulty getting food down; (ii) on a scale ranging from 0 to 10, a worst discomfort with food; (iii) on a scale ranging from 0 to 10, a worst pain with food; (iv) a mean score of any combination of (i), (ii), and (iii); (v) a number of dysphagia episodes; (vi) a daily rate of dysphagia episodes; or (vii) a number of dysphagia-free days.

In some embodiments, the symptom score is the mean of two or more symptom score measurements. In some embodiments, the mean score is the mean of (i) on a scale ranging from 0 to 10, a difficulty getting food down, (ii) on a scale ranging from 0 to 10, a worst discomfort with food, and (iii) on a scale ranging from 0 to 10, a worst pain with food. In some embodiments, the mean score is calculated for one or more episodes of dysphagia over a period of time. For example, the mean score may be calculated from the score for each episode of dysphagia over 1 day, 2 days, 3 days, 4 days, 5 days, 6 days, 7 days, 8 days, 9 days, 10 days, 11 days, 12 days, 13 days, 14 days, or 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34, 35, 36, 37, 38, 39, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks. In some embodiments, the mean score may be calculated from the score for each episode of dysphagia over 1, 2, 3, 4, 5, 6, 7, 8, 9, 10, 11, 12, 13, 14, 15, 16, 17, 18, 19, 20, 21, 22, 23, or 24 months. The mean score of (i) difficulty, (ii) discomfort and (iii) pain may be referred to as the "episode severity score." An episode severity score may be assigned to a single episode of dysphagia. Alternatively or in addition, an episode severity score may be assigned each day as the "daily episode severity score". The daily episode severity score is the average episode severity score of all episodes of dysphagia that occur on a single day. In some embodiments, the daily episode severity score is averaged over a fourteen day period.

In some embodiments, the methods of the disclosure utilize the mean score of the symptom score, wherein if the patient experiences more than one episode of dysphagia, the mean score is calculated for the worst episode or worst symptoms of dysphagia.

In some embodiments, the methods of the disclosure utilize the mean score of the symptom score, wherein the mean score is: (a) a daily mean of (i), (ii), and (iii) over a 14 day period; (b) a mean score of (i), (ii), and (iii) for the worst episode of dysphagia over a 14 day period; (c) a score for the worst symptom of dysphagia over a 14 day period; (d) a number of dysphagia episodes; (e) a daily rate of dysphagia episodes; or (f) a number of dysphagia-free days.

In some embodiments, the methods of the disclosure lead to an improvement in the symptom score by 0.5 to 4 points.

In some embodiments, the symptom score, the mean score, the worst episode score, or the worst symptom score is determined using data from 2 weeks of entries immediately prior to Week 12 and Week 26 of treatment.

In some embodiments, the methods of the disclosure leads to an improvement in the EREFS score by about 0.3 to 1.5 points.

In some embodiments, the methods of the disclosure lead to an improvement in the Global EoE score by about 1 to 4 points.

In some embodiments, the methods of the disclosure cause the PGIS score to shift to improvement by about 1 to 5 severity categories.

In some embodiments, the methods of the disclosure cause the EEsAI score to improve by about 2 to 15 points.

In some embodiments, the methods of the disclosure cause the patient to show improvement in the Eosinophilic Esophagitis Quality of Life Questionnaire (EoO-QoL-A).

In some embodiments, the methods of the disclosure cause the patient to show improvement by about 1 to 3 points in the Eosinophilic Esophagitis Quality of Life Questionnaire (EoO-QoL-A).

In some embodiments, the methods of the disclosure lead to a reduction in a patient's eosinophil count in the patient's esophagus compared to the patient's baseline eosinophil levels.

In some embodiments, the methods of the disclosure lead to an eosinophil count that is reduced to no more than 6 eosinophils per high power field (hpf).

In some embodiments, the methods of the disclosure involve measurement of the eosinophil count in the distal portion of the esophagus, the proximal portion of the esophagus, or both.

In some embodiments, the methods of the disclosure lead to an eosinophil count in the distal portion of the esophagus of no more than 6 eosinophils per hpf.

In some embodiments, the methods of the disclosure lead to an eosinophil count in the proximal portion of the esophagus of no more than 6 eosinophils per hpf.

In some embodiments, the methods of the disclosure lead to a decreased number of dysphagia episodes compared to a patient that is administered the corticosteroid twice daily.

In some embodiments, the methods of the disclosure lead to an increased number of dysphagia-free days compared to a patient that is administered the corticosteroid twice daily.

In some embodiments, the methods of the disclosure provide measurement of the risk of candidiasis and an improvement in at least one of the outcomes at week 1, 2, 3, 4, 5, 6, 7, 8, 9, 10, 11, and/or 12.

In some embodiments, the methods of the disclosure measure the risk of candidiasis and an improvement in at least one of the outcomes again at week 26 and/or week 52.

In some embodiments, the methods of the disclosure provide administration of a corticosteroid in an amount ranging from about 1 mg to about 5 mg, including 1 mg, 1.5 mg, 2 mg, 2.5 mg, 3, mg, 3.5 mg 4, mg, 4.5 mg, and 5 mg.

In some embodiments, fluticasone propionate or the corticosteroid is administered for about 12 weeks to at least one year.

In some embodiments, 1.5 mg of fluticasone propionate is administered. In some embodiments, 3.0 mg of fluticasone propionate is administered.

In some embodiments, the corticosteroid is budesonide. In some embodiments, budesonide is administered for about 12 weeks to at least one year. In some embodiments, 0.5-2 mg of budesonide is administered.

In some embodiments, the corticosteroid that is formulated as a solid composition. In some embodiments, the solid composition is in the form of a gel, lozenge, lollipop, effervescent tablet, powder, granules, an orally disintegrating composition or an orally dispersing composition.

In some embodiments, the orally disintegrating composition is a tablet, wafer, film, effervescent, or lyophilized matrix. In some embodiments, the orally dispersing composition is a tablet, wafer, film, effervescent, or lyophilized matrix.

In some embodiments, the methods of the disclosure provide an improvement in the visual dysphagia question (VDQ) composite score compared to a patient that is administered the corticosteroid twice daily.

In some embodiments, the methods of the disclosure provide an improvement in the EEsAI total score compared to a patient that is administered the corticosteroid twice daily.

BRIEF DESCRIPTION OF THE FIGURES

FIG. 2 depicts the EoE histologic response rate at week 12 in the full analysis set (FAS) population.

5

Responder=histological responder defined as a subject with ≤6 peak eosinophils/high-power field (HPF).

Figure 6:
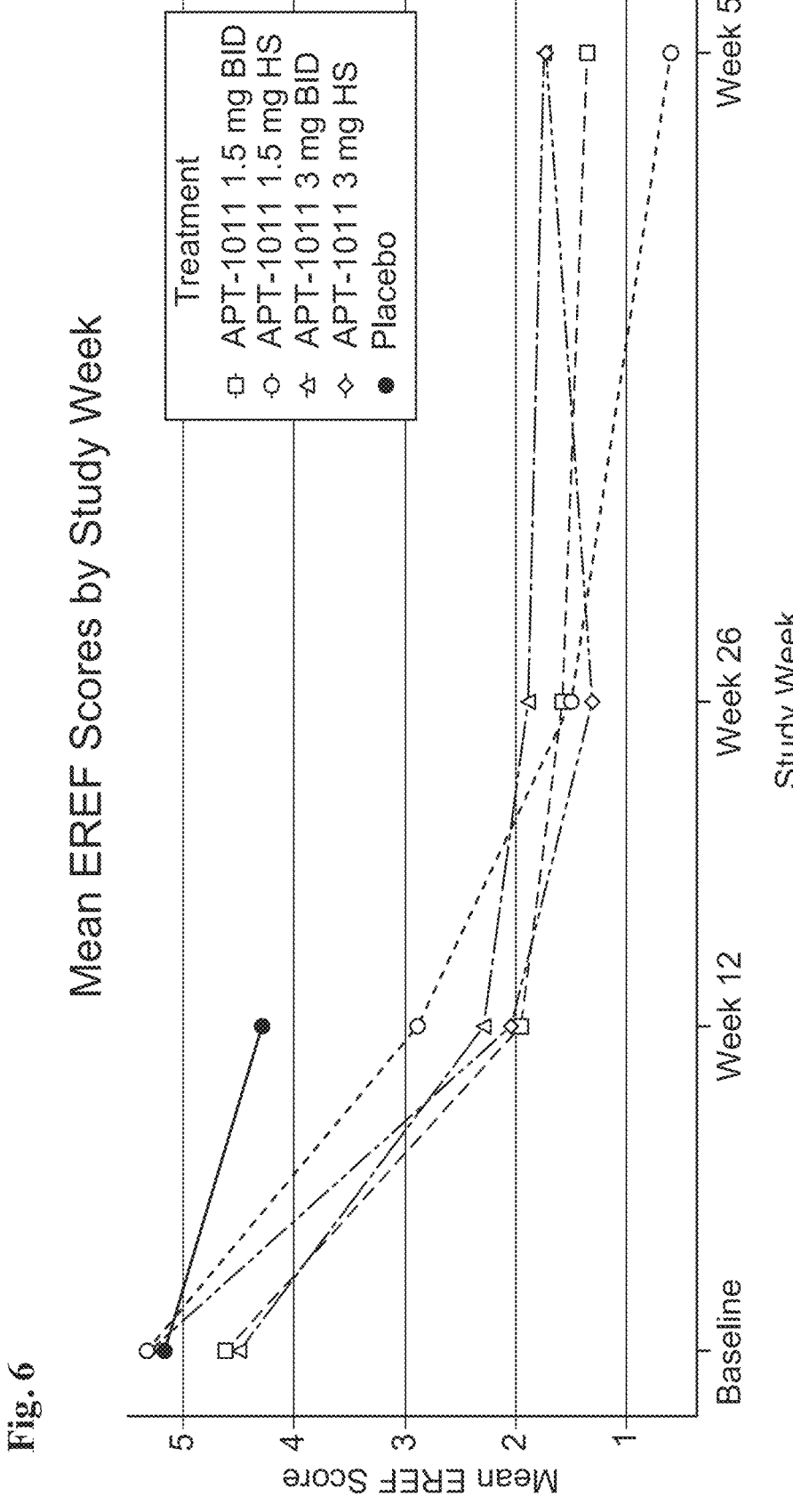

FIG. 6 depicts the Endoscopic Severity measured by EREFS over 52 weeks.

Figure 7:
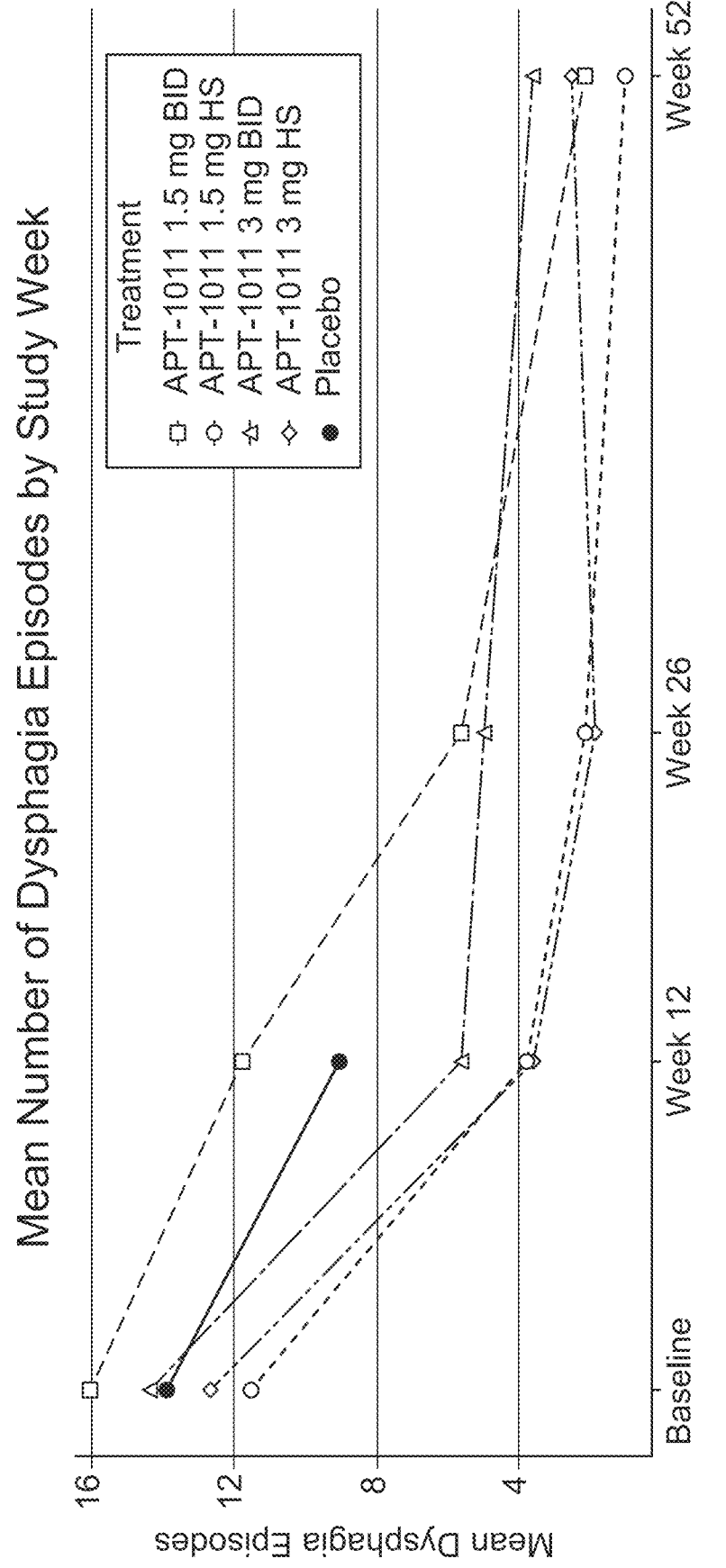

FIG. 7 depicts the reduction in episodes of dysphagia over 52 weeks.

Figure 8:
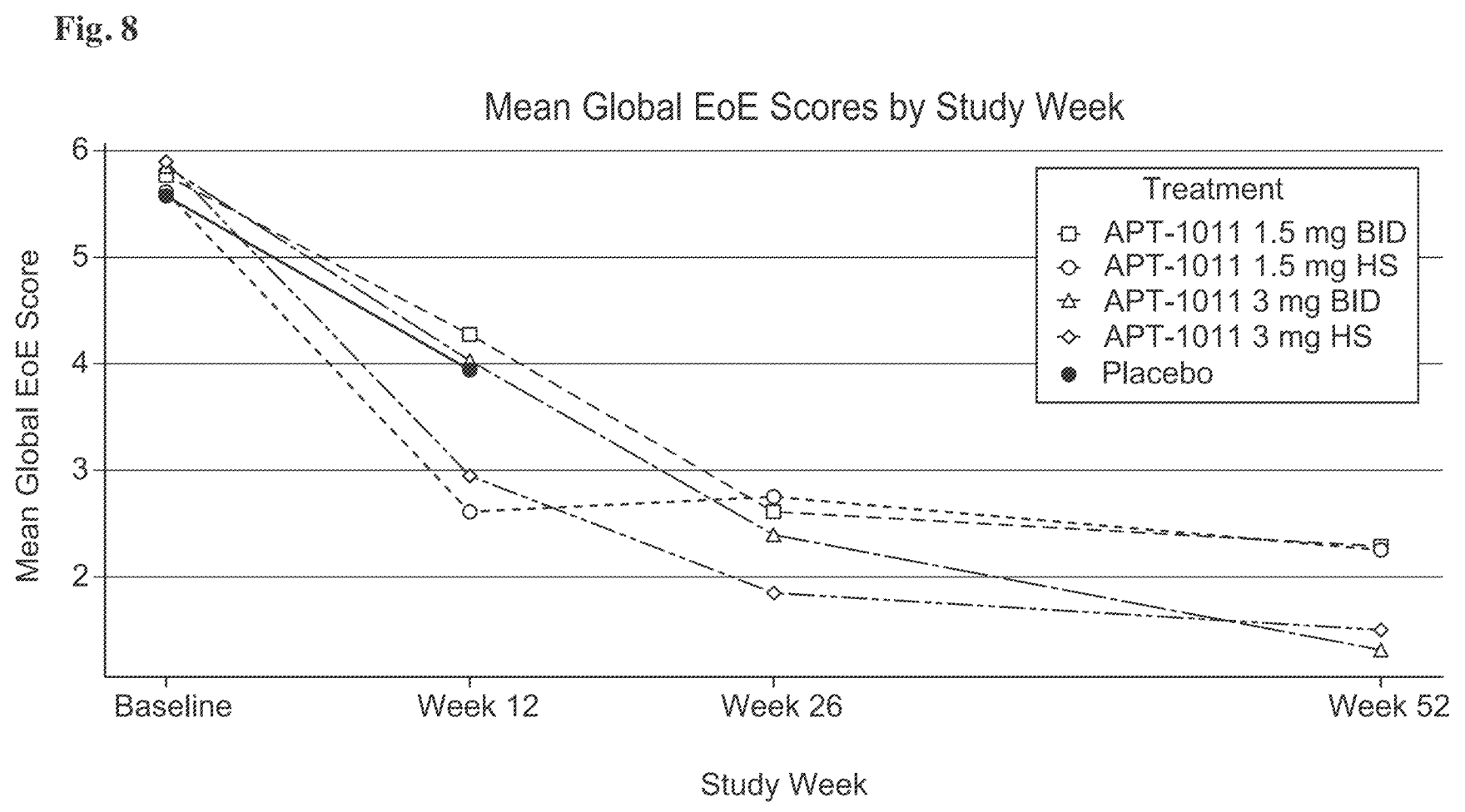

FIG. 8 depicts the reduction in Global EoE scores over 52 weeks.

Figure 9:
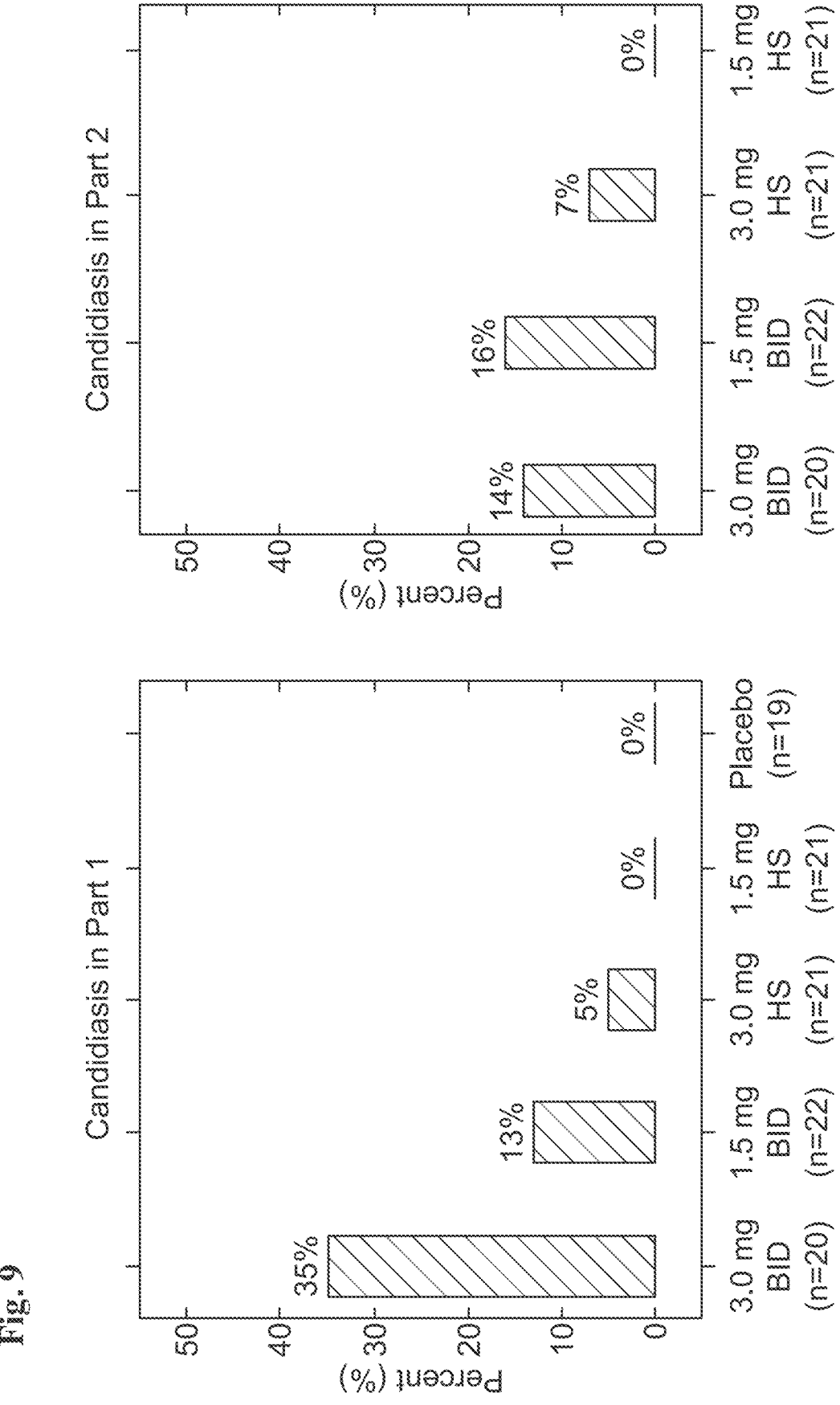

FIG. 9 graphically depicts a comparison of the incidence rates of candidiasis (esophageal, oral, and oropharyngeal) in part 1 and part 2 of the study.

DETAILED DESCRIPTION

Disclosed herein are methods of treating EoE that result in a reduced risk of candidiasis and improved symptom scores. Applicant's surprisingly and unexpectedly discovered that once-daily administration of a corticosteroid not only reduces the patient's risk of candidiasis, but also improves the patient's symptom scores, compared to a patient that was treated with the corticosteroid twice daily. Thus, once-daily treatment results in a better clinical outcome compared to twice-daily treatment. In some embodiments, the total daily dose for the once-daily administration and for the twice-daily administration is the same. For example, a patient who received 3 mg fluticasone propionate once-daily according to the methods describes herein has improved symptom scores and reduced risk of candidiasis compared to a patient that received 1.5 mg twice daily (BID), for a total daily dose of 3 mg. In some embodiments, the total daily dose for twice daily administration is more than the total daily dose for the once daily administration. For example, a patient that is administered 3 mg of a corticosteroid once daily at bedtime according to the methods describes herein has improved symptom scores and reduced candidiasis compared a patient receiving 3 mg of corticosteroid twice-daily (i.e., a total daily dose of 6 mg).

Definitions

As used herein, and in the appended claims, the singular forms "a", "an", and "the" include plural referents unless the context clearly dictates otherwise. Thus, for example, reference to "a protein" can refer to one corticosteroid or to mixtures of corticosteroid, and reference to "the method" includes reference to equivalent steps and/or methods known to those skilled in the art, and so forth.

As used herein, the term "about" or "approximately" when preceding a numerical value indicates the value plus or minus an acceptable degree of variation in the art. In some embodiments, "about" indicates the value plus or minus a range of 10%. For example, "about 100" encompasses 90 and 110.

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of EoE; ameliorating, or reducing the development of or symptoms of EoE; or a combination thereof.

As used herein, the term "about" means plus or minus 10% of the indicated numerical value.

Eosinophilic Oesophagitis (EoE)

In some embodiments, the methods of the present disclosure are utilized to treat EoE. EoE has been described in children and adults with dysphagia and other oesophageal symptoms either alone (typical presentation) or as a manifestation of eosinophilic gastroenteritis (unusual presentation). In its isolated form, the disease exhibits symptoms and histologies similar to gastroesophageal reflux disease (GERD) (e.g., dysphagia, food impaction, nausea, vomiting, and weight loss) and due to this in its first appearance in the 1960's EoE was originally diagnosed as GERD (Furuta et al. 2007). Over time, the similarities were questioned as EoE patients did not experience reflux and did not typically respond to anti-reflux therapy, and it was thereafter considered as a separate clinical entity.

In some embodiments, EoE is defined as a primary clinicopathologic disorder of the oesophagus, which is characterised by oesophageal and/or upper gastrointestinal (GI) tract symptoms in association with oesophageal mucosal biopsy specimens containing ≥15 intraepithelial eosinophils (EOS)/high power field (HPF) in one or more biopsy specimens and absence of pathologic GERD as evidenced by a normal pH monitoring study of the distal oesophagus or lack of response to high-dose proton pump inhibitor (PPI) medication.

EoE affects all ages and ethnic backgrounds. EoE is predominant in non-Hispanic whites. The majority of affected patients with EoE are male, who usually present with EoE symptoms during childhood or in their 30's or 40's. EoE in children usually presents between the ages of 5 and 10 years old and 70% of childhood EoE persists into adulthood. Clinical manifestations of EoE may vary with age with a difference in symptoms between infants and young children compared to adolescents and adults. In contrast to younger children, older children typically present with either heartburn or symptoms of dysphagia. Adolescents present with an oesophageal food impaction. Patients with an atopic background or food-allergies have been shown to present with more severe oesophageal symptoms and food impaction. In some embodiments, common symptoms of EoE during adolescence are GERD-like symptoms. In some embodiments, children aged 11 years and older mostly report dysphagia and food impactions, which are also the most common indications for endoscopy in adult patients.

In some embodiments, EoE patients may be diagnosed using any appropriate measures in the art. In some embodiments, the patient is diagnosed with EoE based on symptoms, score in the assessment using a patient reported outcome (PRO) questionnaire, histology, and/or failed documentation on proton pump inhibitors. In some embodiments, the patient received proton-pump inhibitor (PPI) therapy prior to administration of a corticosteroid. In some embodiments, the patient failed to improve after 8 weeks of high-dose (e.g. 40 mg) PPI. A lack of response to PPI therapy may be defined as Peak eosinophil count >15/HPF in at least one biopsied location after 8 weeks of treatment with a high dose PPI. In some embodiments, the failure of PPI therapy is documented before administration of a pharmaceutical composition of the present disclosure. In some embodiments, the patient did not receive PPI therapy prior to administration of a corticosteroid.

The cause of EoE is unknown but it is believed to be caused by an abnormal immune response to environmental allergens, including food. There also appears to be a genetic component that predisposes certain patients to the condition.

In some embodiments, the methods of the disclosure utilize corticosteroids (e.g. fluticasone propionate or budesonide) for the treatment of EoE. Conventionally, steroid treatment required repurposing formulations intended for inhalers in order to orally administer corticosteroids (e.g. spraying the medication into the mouth and swallowing, or emptying the contents intended for nebulization into a liquid preparation or suspension). However, these inhaled formulations and liquid preparations had many drawbacks, including poor patient compliance and high rates of fungal infections, including oral, oropharyngeal, and oesophageal candidiasis.

In some embodiments, the methods of the disclosure provide administration of a corticosteroid that is formulated as a solid composition. In some embodiments, the solid composition is in the form of a gel, lozenge, lollipop, effervescent tablet, powder, granules, an orally disintegrating composition or an orally dispersing composition. In some embodiments, the orally disintegrating composition is a tablet, wafer, film, effervescent, or lyophilized matrix. In some embodiments, an orodispersible tablet of budesonide is used for the treatment of EoE. In some embodiments, an orodispersible (or orally disintegrating) tablet of fluticasone (or any other corticosteroid) is used for the treatment of EoE.

While solid compositions improve patient compliance, current dosing methods still present a risk of infections. The most common infections associated with long term corticosteroid use in EoE patients are fungal infections, including oral, oropharyngeal, and oesophageal candidiasis. For example, JORVEZA® is an orodispersible tablet containing 1 mg of budesonide, and is approved in Europe for twice daily dosing to treat EoE (i.e., the total daily dose is 2 mg). However, the candidiasis infection rate associated with JORVEZA® is high. 16.9% of patients experience esophageal candidiasis, 3.4% of patients experience oral candidiasis, and 5.1% of patients experience oropharyngeal candidiasis. Fungal infections present symptoms that are similar to EoE, such as difficulty and discomfort in swallowing. Thus, even though the corticosteroid therapy is effective in reducing esophageal inflammation, patients treated with JORVEZA® (or other corticosteroids) may still believe they are experiencing EoE.

The present inventors surprisingly and unexpectedly found that once daily administration of a corticosteroid is more effective to treat EoE and improve EoE symptoms than twice daily administration, even when the total daily dose for the once daily administration is the same as the total daily dose for twice daily administration. Not only is once daily administration of a corticosteroid effective to treat EoE (e.g., by reducing eosinophils), but once daily administration significantly reduces the risk of candidiasis compared to twice daily administration. As such, patients administered the corticosteroid once daily have surprisingly improved symptom outcomes compared to patients receiving twice daily administration.

Corticosteroids and Additional Therapeutic Agents

In some embodiments, any therapeutic agent, which can treat or ameliorate eosinophilic esophagitis, can be used in the methods described herein. Suitable therapeutic agents include those that reduce esophageal inflammation, reduce the number of esophageal eosinophils, or a combination thereof.

In some embodiments, methods of the present disclosure involve the administration of one or more corticosteroids to a patient with eosinophilic esophagitis. Suitable corticosteroids include, but are not limited to hydrocortisone, prednisone, prednisolone, methylprednisolone, dexamethasone, betamethasone, etc. or mineralocorticoid potencies (e.g., alsosterone), budesonide, fluticasone, flunisolide, ciclesonide, mometasone, beclomethasone, tixocortol and salts, or esters and mixtures thereof. In some embodiments, budesonide is administered to a patient in need. In some embodiments, the therapeutic agent is fluticasone, or an ester thereof. In some embodiments, the therapeutic agent is fluticasone propionate.

In some embodiments, the methods of the disclosure involve administration of an oral dosage form of fluticasone propionate. Fluticasone propionate (FP) is a medium-potency synthetic corticosteroid having the chemical name S-(fluoromethyl)-6α,9-difluoro-11β, 17-dihydroxy-16α-methyl-3-oxoandrosta-1, 4-diene-17β-carbothioate, 17-propanoate. The molecular formula of fluticasone propionate is $C_{25}H_{31}F_3O_5S$. The chemical structure of fluticasone propionate is:

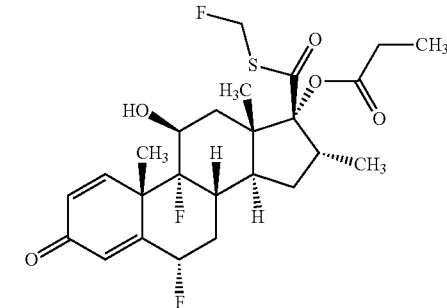

Fluticasone propionate (also referred to herein as "FP") is a white to off-white powder. It is freely soluble in dimethyl sulfoxide and dimethylformamide, sparingly soluble in acetone, dichloromethane, ethyl acetate and chloroform, slightly soluble in methanol and 95% ethanol, and practically insoluble in water. FP decomposes without melting. The onset of decomposition occurs at about 225° C.

In some embodiments, fluticasone propionate is formulated as an orally disintegrating (also referred to as orally dispersing or orodispersible) tablets with an excipient mixture consisting of crospovidone, mannitol colloidal silicon dioxide, silicified microcrystalline cellulose, sucralose, and sodium stearyl fumarate. In some embodiments, the orally disintegrating table comprises about 1.5 or 3.0 mg of fluticasone propionate. In some embodiments, the ODT is described in U.S. Pat. No. 8,771,729 or U.S. Pat. No. 10,471,071, each of which are herein incorporated by reference.

Fluticasone propionate is a medium-potency glucocorticoid with anti-inflammatory including anti-eosinophilic activity in vitro and in vivo. It has proven efficacy to treat conditions believed to have a similar pathophysiology as EoE, including asthma, allergic rhinitis, and atopic dermatitis, and has been marketed worldwide since the early 1990s in topical and inhalation products. Topical (delivered to the throat and swallowed) fluticasone propionate has demonstrated efficacy in resolving acute clinical and pathological features of EoE. In some embodiments, an orodispersible (or orally disintegrating) tablet (ODT) form of fluticasone propionate is used for the treatment of EoE. In some embodiments, ODTs are designed to release the drug in the oral cavity before swallowing without the ingestion of liquids. Thereby, the active substance is delivered directly to the site of action: the oesophagus.

In some embodiments, one or more additional therapeutic agents may be co-administered with the corticosteroid. Such therapeutic agents include proton pump inhibitors (PPI), including, but not limited to, omeprazole, lansoprazole, dexlansoprazole, rabeprazole, pantoprazole, and esomeprazole.

In some embodiments, the additional therapeutic agent comprises one or more immunosuppressant. Suitable immunosuppressants include, but are not limited to, cyclosporine, tacrolimus, prednisolone, hydrocortisone, sirolimus, everolimus, azathioprine, mycophenolic acid, methotrexate, basiliximab, daclizumab, rituximab, mepolizumab (anti-IL-5), reslizumab (anti-IL-5), QAX576 (anti-IL-13), omalizumab (anti-immunoglobulin-E), infliximab (anti-TNF-α), anti-thymocyte globulin, and anti-lymphocyte globulin.

In some embodiments, the pharmaceutical compositions disclosed herein are co-administered with one or more antibodies. Suitable anti-bodies include, include IL-4, IL-5, and IL-13 antibodies. Non-limiting examples include basiliximab, daclizumab, rituximab, mepolizumab (anti-IL-5), reslizumab (anti-IL-5), QAX576 (anti-IL-13), and omalizumab (anti-immunoglobulin-E).

In some embodiments, the one or more therapeutic agents may be "co-administered", i.e., administered together in a coordinated fashion to a subject, either as separate pharmaceutical compositions or admixed in a single pharmaceutical composition. By "co-administered", the one or more therapeutic agents may also be administered simultaneously with the present pharmaceutical compositions, or be administered separately, including at different times and with different frequencies. The one or more therapeutic agents may be administered by any known route, such as orally, intravenously, intramuscularly, nasally, subcutaneously, and the like; and the therapeutic agent may also be administered by any conventional route.

In some embodiments, the therapeutic agents in the above paragraphs can be combined. When two or more medicines are used in combination, dosage of each medicine is commonly identical to the dosage of the medicine when used independently. If a medicine interferes with metabolism of other medicines, the dosage of each medicine is properly adjusted. Each medicine may be administered simultaneously or separately in an appropriate time interval.

In some embodiments, the therapeutic agent for use in the present methods can be formulated into any appropriate dosage form, such as oral orally, parenterally, by inhalation spray, or topically, in formulations containing pharmaceutically acceptable carriers, adjuvants and vehicles. The term parenteral as used here includes subcutaneous, intravenous, intramuscular, and intraarterial injections with a variety of infusion techniques.

In some embodiments, the pharmaceutical compositions used in (or for use in) the methods described herein can be any dosage form which can topically administer a corticosteroid to the esophagus. Non-limiting examples of suitable dosage forms include liquid compositions (e.g., solutions, suspensions, and slurries), gels, and solid compositions which form a liquid or gel after oral administration. For example, orally disintegrating compositions (e.g., ODT, effervescent, film, lyophilize matrix, or wafer), lozenges, and lollipops can from a solution, suspension, or gel comprising the therapeutic agent in the oral cavity of the patient, and after the solution or suspension is swallowed, the corticosteroid dissolved or suspended therein contacts the esophagus as the liquid traverses the esophageal tract. In a preferred embodiment, the pharmaceutical composition is in the form of an ODT.

Wafers can include dried or lyophilized compositions such as orally disintegrating or dissolving dosage forms prepared using Zydis® lyophilization technology (e.g., as described in U.S. Pat. No. 6,316,027), containing a corticosteroid as the active pharmaceutical ingredient. Film dosage forms can include edible films such as those described in U.S. Pat. No. 6,596,298 or 6,740,332, containing a corticosteroid as the active pharmaceutical ingredient. In some embodiments, the solid composition comprises a lyophilized matrix, wherein the lyophilized matrix comprises a corticosteroid, the carrier and excipient. Suitable excipients include, but are not limited to, mannitol, xylitol, sorbitol, maltol, maltitol, lactose, sucrose, maltose, and combinations thereof.

Effervescent tablets and effervescent orally dispersing tablets can include those disclosed in U.S. Pat. Nos. 9,867, 780 and 8,580,300. Such formulations contain weak acids or salts of weak acids, such as tartaric acid, acetic acid, lactic acid, or citric acid, or pharmaceutically acceptable salts thereof, such as magnesium, calcium, or sodium salts. These formulations may also include pharmaceutically acceptable excipients that release $CO_2$ upon contact with water (e.g., saliva), such as carbonic acid, and salts of carbonates and bicarbonates, such as sodium and potassium salts. In some embodiments, such effervescent tablets are formulated to dissolve in a solution prior to oral administration. Such formulations may further comprise polyvinylpyrrolidone.

Dosing

In some embodiments, the methods of the disclosure involve administration of a therapeutically effective dose of fluticasone propionate. In some embodiments, the therapeutically effective dose is from about 0.5 mg to about 5 mg of fluticasone propionate. In some embodiments, fluticasone propionate is administered in a dose of about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, or about 5.0 mg. In some embodiments, 1.5 mg of fluticasone propionate or an equipotent dose of a corticosteroid is administered. In some embodiments, 3.0 mg of fluticasone propionate or an equipotent dose of a corticosteroid is administered.

While the compositions and methods described herein use or refer to a dose of fluticasone propionate, the disclosure envisions using other corticosteroids and obtaining substantially similar efficacy, improvements in symptoms scores, and reduction in candidiasis. The disclose envisions that such corticosteroid are used in an equipotent to fluticasone propionate to achieve the efficacy and symptom scores described herein. In embodiments, the corticosteroid has an equipotent dose to 1.5 mg or 3.0 mg of fluticasone propionate. A person of skill in the art could determine the equipotent dose based on the corticosteroid's relative glucocorticoid receptor binding affinity or the relative potency of the corticosteroid's anti-inflammatory activity. In some embodiments, the equipotent dose is calculated based on the relative glucocorticoid activity corticosteroid's relative glucocorticoid receptor binding affinity. The glucocorticoid receptor binding affinity gives a measure of the dose necessary to occupy 50% of the glucocorticoid receptors. Table 1 gives the relative glucocorticoid receptor binding affinities for a number of corticosteroids. In some embodiments, pharmacokinetic/pharmacodynamic modelling is utilized to estimate the equipotent dose of corticosteroid. The following article which describes methods of calculating equipotent doses is incorporated by reference in its entirety herein: Daley-Yates, Br J Clin Pharmacol. 2015 September; 80(3): 372-380.

TABLE 1

| Relative Glucocorticoid Receptor Binding Affinities | |
| --- | --- |
| Drug | Relative Glucocorticoid Receptor Binding Affinity |
| Fluticasone furoate DPI | 2989 |
| Mometasone furoate DPI | 2100 |
| Fluticasone propionate DPI | 1775 |
| Beclomethasone dipropionate (BMP) MDI | 53 (1345) |
| Ciclesonide (des-CIC) MDI | 12 (1200) |
| Budesonide DPI | 935 |
| Triamicinolone acetonide MDI | 233 |
| Flunisolide MDI | 190 |
| Prednisolone oral | 12 |

MDI: metered-dose inhaler;
DPI: dry-powder inhaler

In some embodiments, the methods of the disclosure provide administration of a corticosteroid in an amount ranging from about 1 mg to about 5 mg, including 1 mg, 1.5 mg, 2 mg, 2.5 mg, 3, mg, 3.5 mg 4, mg, 4.5 mg, and 5 mg. In some embodiments, the equipotent dose of a corticosteroid is from 0.05 mg to 20 mg. In some embodiments, the equipotent dose of a corticosteroid ranged from about 0.05 mg to about 20 mg, e.g., about 0.05 mg, or about 0.1 mg, or about 0.15 mg, or about 0.2 mg, or about 0.25 mg, or about 0.30 mg, or about 0.35 mg, or about 0.40 mg, or about 0.45 mg, or about 0.50 mg, or about 0.55 mg, or about 0.60 mg, or about 0.65 mg, or about 0.70 mg, or about 0.75 mg, or about 0.80 mg, or about 0.85 mg, or about 0.9 mg, or about 0.95 mg, or about 1.0 mg, or about 1.5 mg, or about 2.0 mg, or about 2.5 mg, or about 3.0 mg, or about 3.5 mg, or about 4.0 mg, or about 4.5 mg, or about 5.0 mg, or about 5.5 mg, or about 6.0 mg, or about 6.5 mg, or about 7.0 mg, or about 7.5 mg, or about 8.0 mg, or about 8.5 mg, or about 9.0 mg, or about 9.5 mg, or about 10.0 mg, or about 10.5 mg, or about 11.0 mg, or about 11.5 mg, or about 12.0 mg, or about 12.5 mg, or about 13.0 mg, or about 13.5 mg, or about 14.0 mg, or about 14.5 mg, or about 15.0 mg, or about 15.5 mg, or about 16.0 mg, or about 16.5 mg, or about 17.0 mg, or about 17.5 mg, or about 18.0 mg, or about 19.0 mg, or about 19.5 mg, or about 20.0 mg, including all ranges between these values. Non-limiting examples of corticosteroids include hydrocortisone, prednisone, prednisolone, methyl-prednisolone, dexamethasone, betamethasone, etc. or mineralocorticoid potencies (e.g., alsosterone), budesonide, fluticasone, flunisolide, ciclesonide, mometasone, beclomethasone, tixocortol and salts, or esters and mixtures thereof.

In some embodiments, the methods of the disclosure involve administration of a total daily dose. As defined herein, the "total daily dose" is the total amount of fluticasone propionate or an equipotent dose of a corticosteroid administered in one day. As discussed herein, once-daily administration of a corticosteroids, according to the methods disclosed herein, improves a patient's symptom scores (as described herein) while also reducing the patient's risk of candidiasis. The total daily dose for once-daily administration may be the same or different as the total daily dose for the twice-daily administration. In some embodiments, the total daily dose for twice daily administration is the same as the total daily dose of once daily administration. For example, the total daily dose for once-daily and twice-daily administration may be 1.5 mg or 3.0 mg fluticasone propionate. In some embodiments, the total daily dose for twice daily administration is more than the total daily dose for the once daily administration. For example, a patient may be administered 1.5 mg fluticasone propionate once-daily, and the patient's symptoms scores and risk of candidiasis may be compared to a patient that receives a total daily dose of 3.0 mg, 4.5 mg, or 6 mg fluticasone propionate, twice-daily. As another example, the patient may be administered 3 mg of a corticosteroid once-daily, and the patient's symptoms scores and risk of candidiasis may be compared to a patient that receives a total daily dose of 4.5 mg or 6 mg fluticasone propionate, twice-daily.

Dosing Regimens

In some embodiments, the methods of the present disclosure offer dosing regimens. In some embodiments, according to the methods of the disclosure, fluticasone propionate is administered once daily. In some embodiments, according to the methods of the present disclosure, fluticasone propionateis administered once a day at bedtime or night time (HS). As defined herein, bedtime is the time at which a patient desires to go to sleep. In some embodiments, fluticasone propionate is administered within 30 minutes, or 1 hour, or 1.5 hour, or 2 hours, or 2.5 hours, or 3.0 hours of a patient's bedtime. In some embodiments, fluticasone propionate is administered within 30 minutes of a patient's bedtime. In some embodiments, fluticasone propionate is administered while the patient is lying down or immediately prior to the patient lying down. As used herein, "immediately prior to the patient lying down" means within 30 minutes of the patient lying down, e.g., within 25, 20, 15, 10 or 5 minutes of the patient lying down. In some embodiments, fluticasone propionate is administered once daily at about 6 p.m., about 6:30 p.m., about 7:00 p.m., about 7:30 p.m., about 8:00 p.m., about 8:30 p.m., about 9:00 p.m., about 9:30 p.m., about 10:00 p.m., about 10:30 p.m., about 11:00 p.m., or about 12:00 a.m. In some embodiments, fluticasone propionate is administered to a patient on an empty stomach (e.g. at least two hours after eating or at least one hour before eating; or at least 30 minutes before or after eating).

In some embodiments, the methods of the disclosure involve administration of an equipotent dose of corticosteroid. In some embodiments, according to the methods of the disclosure, the equipotent dose of corticosteroid is administered once daily. In some embodiments, according to the methods of the present disclosure, the equipotent dose of corticosteroid is administered once a day at bedtime or night time (HS). In some embodiments, the equipotent dose of corticosteroid is administered within 30 minutes, or 1 hour, or 1.5 hours, or 2 hours, or 2.5 hours, or 3.0 hours of a patient's bedtime. In some embodiments, the equipotent dose of corticosteroid is administered while the patient is lying down or immediately prior to the patient lying down. In some embodiments, the equipotent dose of a corticosteroid is administered once daily at about 6 p.m., about 6:30 p.m., about 7:00 p.m., about 7:30 p.m., about 8:00 p.m., about 8:30 p.m., about 9:00 p.m., about 9:30 p.m., about 10:00 p.m., about 10:30 p.m., about 11:00 p.m., or about 12:00 a.m. In some embodiments, the equipotent dose of a corticosteroid is administered to a patient on an empty stomach (e.g. at least two hours after eating or at least one hour before eating; or at least 30 minutes before or after eating).

In some embodiments, fluticasone propionate or an equipotent dose of a corticosteroid are administered for a defined length of time. In some embodiments, the methods of the disclosure provide administration of fluticasone propionate or the corticosteroid is administered for about 12 weeks to at least one year. In some embodiments, the length of time is at least 12 weeks, or at least 13 weeks, or at least 14 weeks, or at least 15 weeks, or at least 16 weeks, or at least 17 weeks, or at least 18 weeks, or at least 19 weeks, or at least 20 weeks, or at least 21 weeks, or at least 22 weeks, or at least 23 weeks, or at least 24 weeks, or at least 25 weeks, or at least 26 weeks, or at least 27 weeks, or at least 28 weeks, or at least 29 weeks, or at least 30 weeks, or at least 31 weeks, or at least 32 weeks, or at least 33 weeks, or at least 34 weeks, or at least 35 weeks, or at least 36 weeks, or at least 37 weeks, or at least 38 weeks, or at least 39 weeks, or at least 40 weeks, or at least 41 weeks, or at least 42 weeks, or at least 43 weeks, or at least 44 weeks, or at least 45 weeks, or at least 46 weeks, or at least 47 weeks, or at least 48 weeks, or at least 49 weeks, or at least 50 weeks, or at least 51 weeks, or at least 52 weeks, or more (e.g., 1 year, 1.5 years, 2, years, 2.5 years, 3 years, 3.5 years, 4 years, 4.5 years, 5 years, and so on).

In some embodiments, the treatment of EoE with a corticosteroid is stopped for a defined length of time to allow the patient to recover from treatment. In some embodiments, the length of time is at least 1 week, or at least 2 weeks, or at least 3 weeks, or at least 4 weeks, or at least 5 weeks, or at least 6 weeks, or at least 7 weeks, or at least 8 weeks, or at least 9 weeks, or at least 10 weeks, or at least 11 weeks, or at least 12 weeks, or at least 13 weeks, or at least 14 weeks, or at least 15 weeks, or at least 16 weeks, or at least 17 weeks, or at least 18 weeks, or at least 19 weeks, or at least 20 weeks, or at least 21 weeks, or at least 22 weeks, or at least 23 weeks, or at least 24 weeks, or at least 25 weeks, or at least 26 weeks, or at least 27 weeks, or at least 28 weeks, or at least 29 weeks, or at least 30 weeks, or at least 31 weeks, or at least 32 weeks, or at least 33 weeks, or at least 34 weeks, or at least 35 weeks, or at least 36 weeks, or at least 37 weeks, or at least 38 weeks, or at least 39 weeks, or at least 40 weeks, or at least 41 weeks, or at least 42 weeks, or at least 43 weeks, or at least 44 weeks, or at least 45 weeks, or at least 46 weeks, or at least 47 weeks, or at least 48 weeks, or at least 49 weeks, or at least 50 weeks, or at least 51 weeks, or at least 52 weeks, or more.

In some embodiments, treatment is stopped for a defined length of time and then restarted. In some embodiments, treatment is restarted after 1 week, or at least 2 weeks, or at least 3 weeks, or at least 4 weeks, or at least 5 weeks, or at least 6 weeks, or at least 7 weeks, or at least 8 weeks, or at least 9 weeks, or at least 10 weeks, or at least 11 weeks, or at least 12 weeks, or at least 13 weeks, or at least 14 weeks, or at least 15 weeks, or at least 16 weeks, or at least 17 weeks, or at least 18 weeks, or at least 19 weeks, or at least 20 weeks, or at least 21 weeks, or at least 22 weeks, or at least 23 weeks, or at least 24 weeks, or at least 25 weeks, or at least 26 weeks, or at least 27 weeks, or at least 28 weeks, or at least 29 weeks, or at least 30 weeks, or at least 31 weeks, or at least 32 weeks, or at least 33 weeks, or at least 34 weeks, or at least 35 weeks, or at least 36 weeks, or at least 37 weeks, or at least 38 weeks, or at least 39 weeks, or at least 40 weeks, or at least 41 weeks, or at least 42 weeks, or at least 43 weeks, or at least 44 weeks, or at least 45 weeks, or at least 46 weeks, or at least 47 weeks, or at least 48 weeks, or at least 49 weeks, or at least 50 weeks, or at least 51 weeks, or at least 52 weeks, or more. Temporarily stopping the corticosteroid is a known as a drug "holiday", and, in some embodiments, it may help to reduce cortisol suppression and other side effects associated with long-term corticosteroid use.

Outcomes

In some embodiments, administration of fluticasone propionate or an equipotent dose of a corticosteroid once daily results in an improvement in one or more outcomes when compared to a patient administered fluticasone propionate or an equipotent dose of a corticosteroid twice daily. Non-limiting examples of patient outcomes include: a reduced risk or incidence of candidiasis; at least one symptom score measured using a patient reported outcome symptom evaluation (PROSE) instrument after an each episode of dysphagia (see e.g., WO 2019/165138) or the 24-hour diary (see e.g., US Publication No. 2016/0078186); the EoE Endoscopic Reference (EREF) score; the EoE Activity Index (EEsAI) avoidance, modification, and slow swallowing (AMS) score; the global EoE score; the eosinophilic oesophagitis quality of life questionnaire; the patient global impression of severity (PGIS); and the patient global impression of change (PGIC).

A patient's risk of candidiasis is determined from the incidence rate in the clinical trial population. The incidence rate of candidiasis is the number of patients that reported a candidiasis infection divided by the total number of patients treated with the corticosteroid during treatment.

In some embodiments, outcomes are measured 1 week, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks, or 16 weeks, or 17 weeks, or 18 weeks, or 19 weeks, or 20 weeks, or 21 weeks, or 22 weeks, or 23 weeks, or 24 weeks, or 25 weeks, or 26 weeks, or 27 weeks, or 28 weeks, or 29 weeks, or 30 weeks, or 31 weeks, or 32 weeks, or 33 weeks, or 34 weeks, or 35 weeks, or 36 weeks, or 37 weeks, or 38 weeks, or 39 weeks, or 40 weeks, or 41 weeks, or 42 weeks, or 43 weeks, or 44 weeks, or 45 weeks, or 46 weeks, or 47 weeks, or 48 weeks, or 49 weeks, or 50 weeks, or 51 weeks, or 52 weeks, or 53 weeks, or 54 weeks, or 55 weeks, or 56 weeks, or 57 weeks, or 58 weeks, or 59 weeks, or 60 weeks, or 61 weeks, or 62 weeks, or 63 weeks, or 64 weeks, or 65 weeks, or 66 weeks, or 67 weeks, or 68 weeks, or 69 weeks, or 70 weeks, or 71 weeks, or 72 weeks, or 73 weeks, or 74 weeks, or 75 weeks, or 76 weeks, or 77 weeks, or 78 weeks, or 79 weeks, or 80 weeks, or 81 weeks, or 82 weeks, or 83 weeks, or 84 weeks, or 85 weeks, or 86 weeks, or 87 weeks, or 88 weeks, or 89 weeks, or 90 weeks, or 91 weeks, or 92 weeks, or 93 weeks, or 94 weeks, or 95 weeks, or 96 weeks, or 97 weeks, or 98 weeks, or 99 weeks, or 100 weeks, or 101 weeks, or 102 weeks, or 103 weeks, or 104 weeks, or more weeks after initiation of treatment according to the methods of the disclosure. In some embodiments, the methods of the disclosure result in an improvement in outcomes at after initiation of treatment according to the methods of the disclosure at 1 week, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks, or 16 weeks, or 17 weeks, or 18 weeks, or 19 weeks, or 20 weeks, or 21 weeks, or 22 weeks, or 23 weeks, or 24 weeks, or 25 weeks, or 26 weeks, or 27 weeks, or 28 weeks, or 29 weeks, or 30 weeks, or 31 weeks, or 32 weeks, or 33 weeks, or 34 weeks, or 35 weeks, or 36 weeks, or 37 weeks, or 38 weeks, or 39 weeks, or 40 weeks, or 41 weeks, or 42 weeks, or 43 weeks, or 44 weeks, or 45 weeks, or 46 weeks, or 47 weeks, or 48 weeks, or 49 weeks, or 50 weeks, or 51 weeks, or 52 weeks, or 53 weeks, or 54 weeks, or 55 weeks, or 56 weeks, or 57 weeks, or 58 weeks, or 59 weeks, or 60 weeks, or 61 weeks, or 62 weeks, or 63 weeks, or 64 weeks, or 65 weeks, or 66 weeks, or 67 weeks, or 68 weeks, or 69 weeks, or 70 weeks, or 71 weeks, or 72 weeks, or 73 weeks, or 74 weeks, or 75 weeks, or 76 weeks, or 77 weeks, or 78 weeks, or 79 weeks, or 80 weeks, or 81 weeks, or 82 weeks, or 83 weeks, or 84 weeks, or 85 weeks, or 86 weeks, or 87 weeks, or 88 weeks, or 89 weeks, or 90 weeks, or 91 weeks, or 92 weeks, or 93 weeks, or 94 weeks, or 95 weeks, or 96 weeks, or 97 weeks, or 98 weeks, or 99 weeks, or 100 weeks, or 101 weeks, or 102 weeks, or 103 weeks, or 104 weeks, or more weeks. In some embodiments, the methods of the disclosure result in an improvement in any of the outcomes described herein for at least 52 weeks.

In some embodiments, the risk of candidiasis and an improvement in at least one of the outcomes are measured at week 1, 2, 3, 4, 5, 6, 7, 8, 9, 10, 11, and/or 12.

In some embodiments, the risk of candidiasis and an improvement in at least one of the outcomes again at week 26 and/or week 52 (or any week therebetween).

In some embodiments, the methods of the disclosure lead to a reduction in a patient's risk of candidiasis, a potentially adverse effect of oral steroid usage. In some embodiments, the methods of the disclosure provide an improvement in oral candidiasis, esophageal candidiasis, and/or oropharyngeal candidiasis. Oral, oropharyngeal, and oesophageal candidiasis infections are known side effects of swallowed corticosteroids, such as budesonide and fluticasone propionate, used for the treatment of EoE. Oral candidiasis is one of the most common fungal infections affecting the fungal mucosa. Oral candidiasis is described by Agrawal et al. in the following citation Agrawal, A., Singh, A., Verma, R., & Murari, A. (2014). Oral candidiasis: An overview. *Journal of Oral and Maxillofacial Pathology*, 18(4), 81. doi: 10.4103/0973-029x. 141325; this reference is incorporated herein in its entirety. Oral candidiasis is caused by *Candida albicans, Candida glabrata, Gandida guillermondii, Candida krusei, Candida guillermondii, Candida krusei, Candida parapsilosis, Candida pseudotropicalis, Candida stellatoidea*, and *Candida tropicalis. Candida* can also infect the esophagus. Esophageal candidiasis is most commonly caused by *Candida albicans*. Esophageal candidiasis is detailed by Nishimura et al. in the following citation Nishimura, S., Nagata, N., Shimbo, T., Asayama, N., Akiyama, J., Ohmagari, N., Uemura, N. (2013). Factors Associated with Esophageal Candidiasis and Its Endoscopic Severity in the Era of Antiretroviral Therapy. *PLoS ONE*, 8(3). doi:10.1371/journal.pone.0058217 this reference is incorporated herein in its entirety. Without being bound by theory, it is postulated that patients who receive steroids experience candidiasis by possibly suppressing local cellular immunity and phagocytosis. The methods described herein reduce immune suppression. In some embodiments, according to the methods of the disclosure, a patient's risk of oral candidiasis is less than about 10% (e.g., about 10%, about 9%, about 8%, about 7%, about 6%, about 5%, about 4%, about 3%, about 2%, about 1% or less).

Candidiasis is diagnosed according to methods known to persons skilled in the art. In some embodiments, oral specimens are grown on agar. Briefly, specimens are collected under aseptic conditions from active lesions. Specimens are kept moist and stored in a refrigerator at 4° C. Smears are taken from the infected oral mucosa, rhagades, and fitting side of denture preferably with wooden spatulas. Smears were fixed immediately in ether/alcohol 1:1 or with spray fix. Dry preparations may be examined by Gram stain method and periodic acid Schiff (PAS) method. Swabs are seeded on various agar substrates to grow the yeast species. Pagano-Levin agar or Littman's substrate are useful supplements, because they enable distinction of yeasts on the basis of difference in colony color.

In some embodiments, an imprint culture technique is utilized for quantitative assessment of yeast growth in different areas of the oral mucosa. Sterile, square plastic foam pads are dipped in peptone water and placed on the restricted area under study for 30-60 seconds and placed thereafter directly on Pagano-Levin or Sabouraud's agar. Subsequently, candidal density at each site is determined by a Gallenkamp colony counter and expressed as colony forming units per $mm^2$ (CFU $mm^{-2}$). This technique is useful for localizing the site of infection.

In some embodiments, impression culture technique is used to estimate the number of colony forming units of yeast. Maxillary and mandibular alginate impressions are taken and cast in 6% fortified agar, incorporated into Sabouraud's dextrose broth, and grown for 48-72 hours at 37° C., and the CFUs of yeast are estimated.

In some embodiments, the number of *Candida* in a patient's saliva is estimated by counting the resultant growth on Sabouraud's agar using either the spiral plating or Miles and Misra surface viable counting technique. Patients who display clinical signs of oral candidiasis usually have more than 400 CFU/mL.

In some embodiments, commercial identification kits are utilized to identify candidiasis, including the Microstix-candida system, the O Yeast-I dent system, and the Ricult-N dip slide technique.

In some embodiments, fungi in biopsy specimens are identified histologically. Hematoxylin and eosin poorly stain *Candida* species. The specific fungal stains such as PAS stain, Grocott-Gomori's metheneamine silver (GMS) and Gridley stains are widely used for demonstrating fungi in the tissues, which are colored intensely with these stains.

In some embodiments, physiological tests are used for definitive identification of *Candida* species. These tests involve the ability of the *Candida* species to assimilate and ferment individual carbon and nitrogen sources (see Table 2 and Table 3).

TABLE 2

| Assimilation Reactions of *Candida* Species | | | | | | | | | | | |
| --- | --- | --- | --- | --- | --- | --- | --- | --- | --- | --- | --- |
| *Candida* species | Glu | Mal | Suc | Lac | Cel | Gal | Tre | Raff | Mel | Xyl | Ino | Dul |
| *C. albicans* | + | + | + | + | + | + | + | − | − | + | − | − |
| *C. tropicalis* | + | + | + | − | + | + | + | − | − | + | − | − |
| *C. keyfer* | + | − | + | + | + | + | − | + | − | + | − | − |
| *C. parapsilosis* | + | + | + | − | − | + | + | − | − | + | − | − |

TABLE 2-continued

| Assimilation Reactions of *Candida* Species | | | | | | | | | | | | |
|---|---|---|---|---|---|---|---|---|---|---|---|---|
| *Candida* species | Glu | Mal | Suc | Lac | Cel | Gal | Tre | Raff | Mel | Xyl | Ino | Dul |
| *C. guilliermondii* | + | + | + | – | + | + | + | + | – | + | – | + |
| *C. krusei* | + | – | – | – | – | – | – | – | – | + | – | – | glucose (Glu), maltose (Mal), sucrose (Suc), lactose (Lac), cellobiose (Cel), galactose (Gal), trehalose (Tre), raffinose (Raff), melibiose (Mel), xylose (Xyl), inositol (Ino), and dulcitol (Dul)
+: Positive reaction,
–: Negative reaction

TABLE 3

| Fermentation Reactions of *Candida* Species | | | | |
|---|---|---|---|---|
| *Candida* Species | Glucose | Maltose | Sucrose | Lactose |
| *C. albicans* | AG | AG | – | – |
| *C. tropicalis* | AG | AG | AG | – |
| *C. keyfer* | AG | AG | AG | – |
| *C. parapsilosis* | AG | – | AG | – |
| *C. guilliermondii* | AG | – | – | – |
| *C. krusei* | AG | – | – | – |
| *C. glabrata* | AG | – | – | – |

+: Positive reaction,
–: Negative reaction,
A: Acid Production,
G: Gas production In some embodiments, serological tests are utilized to detect invasive candidiasis including the detection of antibodies, immunodiffusion, slide agglutination, phytohemagglutination, coelectosynersis, immunoprecipitation, A and B immunofluorescence, nonspecific *Candida* antigens, latex agglutination, immunoblotting, β-(1,3)-D-glucan, cell wall mannoprotein, cell wall components, and *candida* enolase antigen testing.

In some embodiments, an upper endoscopy is necessary for diagnosis, particularly if the candidiasis is an esophageal candidiasis. White-yellow plaques can be seen on upper endoscopy. Plaques and exudates are adherent to the mucosa and do not wash off with water irrigation. There may also be mucosal breaks or ulcerations. Hematoxylin and eosin stain of biopsies or brushing of esophageal candidiasis show pseudohyphae which is diagnostic for esophageal candidiasis. Pathology may demonstrate acute inflammation and/or intraepithelial lymphocytosis.

In some embodiments, patients treated according to the methods of the disclosure exhibit a risk of candidiasis of less than about 10%. In some embodiments, patients treated according to the methods of the disclosure exhibit a risk of candidiasis of less than about 9%, or less than about 8%, or less than about 7%, or less than about 6%, or less than about 5%, or less than about 4%, or less than about 3%, or less than about 2%, or less than about 1%. In some embodiments, the methods of the present disclosure lead to a reduced incidence of candidiasis. In some embodiments, incidences of candidiasis are reduced by about 1%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100%, inclusive of all values and ranges therein, compared to an otherwise identical patient that is treated with the corticosteroid twice daily.

In some embodiments, according to the methods of the disclosure, a patient's risk of oral candidiasis is less than about 4%, less than about 3%, less than about 2%, or less than about 1%. In some embodiments, according to the methods of the disclosure, a patient's risk of oral candidiasis is about 4.8%. In some embodiments, instances of oral candidiasis are reduced by about 1%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100%, inclusive of all values and ranges therein, compared to an otherwise identical patient that is treated with the corticosteroid twice daily.

In some embodiments, according to the methods of the disclosure, a patient's risk of esophageal candidiasis is less than about 10%. In some embodiments, according to the methods of the disclosure, a patient's risk of esophageal candidiasis is less than about 10%, or 9%, or 8%, or 7%, or 6%, or 5%, or 4%, or 3%, or 2%, or 1%. In some embodiments, instances of esophageal candidiasis are reduced by about 1%, about 5%, about 10%, about 15%, about 20%, about 25%, about 30%, about 35%, about 40%, about 45%, about 50%, about 55%, about 60%, about 65%, about 75%, about 80%, about 85%, about 90%, about 95%, or about 100%, inclusive of all values and ranges therein, compared to an otherwise identical patient that is treated with the corticosteroid twice daily.

In some embodiments, the methods of the present disclosure cause patients to show an improvement in at least one symptom score measured using a patient reported outcome evaluation (PROSE) instrument after an episode of dysphagia. The PROSE instrument computes several items, including the number of real-time episode entry (RTE) dysphagia episodes, the number of end of day recorded dysphagia episodes, the total number of dysphagia episodes, the proportion of RTE dysphagia episodes, the total duration of dysphagia, the total imputed duration of dysphagia, the number of dysphagia free days, the worst difficulty recorded in an RT episode, the worst pain recorded in an RT episode, the worst discomfort recorded in an RT episode, the worst composite symptom summary score, the worst difficulty recorded in an EOD episode, the worst pain recorded in an EOD episode, the worst discomfort recorded in an EOD episode, the worst composite symptom summary score, maximum reported difficulty response, maximum reported pain response, maximum reported discomfort response, and the worst composite symptom summary score. In some embodiments, PROSE computes the average of all ratings over a 14-day period. In some embodiments, the symptom score is the total number of dysphagia episodes experienced over 14 days. This may also be referred to as the frequency of dysphagia.

In some embodiments, PROSE provides symptom summary ratings, based on the following questions: (i) how difficult, on a scale from 1-10, was it for you to get the food and/or pills down? (ii) what was the worst pain you felt, on a scale from 1-10, when trying to get the food and/or pills down? (iii) What was the worst discomfort you felt, on a scale from 1-10, when trying to get the food/pills down? In some embodiments, the PROSE symptom score is the a mean score of any combination of (i), (ii), and (iii). In some embodiments, the mean score of (i), (ii), and (iii) is referred to as "episode severity."

An episode severity score may be assigned to a single episode of dysphagia. Alternatively or in addition, an episode severity score may be assigned each day as the "daily episode severity score". The daily episode severity score is the average episode severity score of all episodes of dysphagia that occur on a single day. In some embodiments, the daily episode severity score over a fourteen day period is averaged.

In some embodiments, the methods of the disclosure lead to an improvement in the average daily episode severity score over a specific time period. The average daily episode severity score over a specific time period is the sum of the daily episode severity score for each day in which an episode of dysphagia is reported divided by the number of days in the time period that the episodes of dysphagia are reported. The episode severity score is the mean of the PROSE symptom scores (i), (ii), and (iii). In some embodiments, the average daily episode severity score is calculated over a time period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 5 weeks, 6 weeks, 7 weeks, 8 weeks, 9 weeks, 10 weeks, 11 weeks, 12 weeks, 1 month, 2 months, 3 months, 4 months, 5 months, 6 months, 7 months, 8 months, 9 months, 10 months, 11 months, 12 months, 18 months, or 2 years. In some embodiments, the average daily episode severity score is calculated over 14 days. For example, if the average daily episode severity score is calculated over a time period of 14 days and the patient experiences episodes of dysphagia on 12 out of 14 days of the time period, the average daily episode score over the 14 day time period is the sum of daily episode severity score of the 12 days reported divided by 12.

In some embodiments, the methods of the disclosure lead to an improvement in symptom burden. The symptom burden is the average daily episode severity score over a specific time period, including days in which no episodes of dysphagia are reported. As discussed herein, the daily episode severity score is the episode severity score divided by the number of dysphagia episodes in one day. The episode severity score is the mean of the PROSE symptom scores (i), (ii), and (iii), wherein a day with no dysphagia episodes is assigned a daily episode severity score of zero. In some embodiments, symptom burden is calculated over a time period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 5 weeks, 6 weeks, 7 weeks, 8 weeks, 9 weeks, 10 weeks, 11 weeks, 12 weeks, 1 month, 2 months, 3 months, 4 months, 5 months, 6 months, 7 months, 8 months, 9 months, 10 months, 11 months, 12 months, 18 months, or 2 years. In some embodiments, the symptom burden is calculated over 14 days. For example, the symptom burden calculated over a time period of 14 days is the sum of the daily episode score of each of the 14 days divided by 14, wherein a day in which no dysphagia episodes are reported is assigned a daily episode score of 0.

In some embodiments, a daily episode severity score is the episode severity score for the worst episode of dysphagia. The worst episode of dysphagia in a given day has the highest episode severity score. The method to calculate the severity score id described herein.

In some embodiments, the methods of the disclosure lead to an improvement in the score of the worst symptom of dysphagia reported over a particular time period. In some embodiments, the worst symptom of dysphagia has the highest PROSE symptom score. For example, if a patient assigns (i) a score of 9, (ii) a score of 5, and (iii) a score of 1, (i) is the worst symptom.

In some embodiments, the PROSE symptom score includes the number of dysphagia episodes. In some embodiments, the PROSE symptom score includes the number of dysphagia episodes daily rate of dysphagia episodes. In some embodiments, the PROSE symptom score includes the number of dysphagia episodes daily rate of dysphagia episodes, a number of dysphagia-free days. In some embodiments, PROSE provides a daily mean composite score (e.g., for all reported incidences of dysphagia) over 14 days, a daily worst composite (e.g., for the reported incidences of dysphagia each day) score over 14 days, a daily worst composite score over 14 days, the number of episodes over 14 days, the daily rate of episodes over 14 days, or the number of dysphagia-free days over 14 days.

In some embodiments, the methods of the disclosure cause the PROSE score (e.g., the episode severity score described above) to improve by about 5%, or about 10%, or about 15%, or about 20%, or about 25%, or about 30%, or about 35%, or about 40%, or about 45%, or about 50%, or about 55%, or about 60%, or about 65%, or about 70%, or about 80%, or about 85%, or about 90%, or about 95%, or about 100%, or more. In some embodiments, the methods of the disclosure cause the number of episodes of dysphagia to decrease as determined by the PROSE instrument. In some embodiments, the methods of the disclosure cause the PROSE score to improve by about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, or more, inclusive of all ranges between these values.

In some embodiments, the PROSE instrument is described in International Publication Number WO/2019/165138, the contents of which are incorporated by reference herein in its entirety. The 24-hour diary refers to a device used for recording various events associated with dysphagia (e.g. associated with EoE) at the end of a 24 hour period, i.e. once a day. At the end of a 24 hour period, the patient recalls all the events associated with dysphagia that occurred over the previous 24 hour period, including inter alia, (i) the severity, intensity, duration, pain, discomfort, difficulty, and/or frequency of dysphagia, (ii) type (including dosage form and active agent) and timing of treatment, and (iii) avoidance measures. In some embodiments, the patient records entries in the 24-hour diary after the last meal. In some embodiments, the patient records entries in the 24-hour diary about 6 p.m., about 6:30 p.m., about 7:00 p.m., about 7:30 p.m., about 8:00 p.m., about 8:30 p.m., about 9:00 p.m., about 9:30 p.m., about 10:00 p.m., about 10:30 p.m., about 11:00 p.m., or about 12:00 a.m.

In some embodiments, methods of the present disclosure cause an improvement as suggested by the 24-hour diary outcome. U.S. Publication No. 2016/0078186 details the 24-hour diary outcome and is incorporated by reference in its entirety for all purposes.

In some embodiments, the methods of the present disclosure cause an improvement in a patient's EoE Endoscopic Reference score (EREFS). The EREFS identifies the severity of five endoscopic findings: edema, rings, exudates, furrows, and strictures. The EREFS classification system rates the severity of each of the endoscopic findings. The severity of edema is rated on a scale from 0 to 2. The severity of rings is rated from 0 to 3. The severity of exudates is rated from 0 to 2. The severity of furrows is rated from 0 to 2. The severity of strictures is rated from 0 to 1. The absence of a finding corresponds to a score of 0. The presence of a finding corresponds to a score of 1, 2, or 3. A higher score is correlated with higher severity. In some embodiments, the composite EREFS score, or the sum of the individual scores, is utilized to indicate the severity of EoE. In some embodiments, the inflammatory EREFS score, or the sum of the individual edeme, exudate, and furrows score, is utilized to indicate the severity of EoE. In some embodiments, a higher inflammatory or composite EREFS score corresponds to the severity of EoE. In some embodiments, the inflammatory or composite EREFS score decreases after treatment with a corticosteroid according to the methods of the disclosure. In some embodiments the inflammatory or composite EREFS score decreases by 0.1, or about 0.2, or about 0.3, or about 0.4, or about 0.5, or about 0.6, or about 0.7, or about 0.8, or about 0.9, or about 1.0, or about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4.0, or about 4.1, or about 4.2, or about 4.3, or about 4.4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0 points, or more, inclusive of all ranges between these values. In some embodiments, the EREFS score decreases by 1%, or 5%, or 10%, or 15%, or 20%, or 25%, or 30%, or 35%, or 40%, or 45%, or 50%, or 55%, or 60%, or 65%, or 70%, or 75%, or 80%, or 85%, or 90%, or 95% or more, inclusive of all ranges between these values. The following article, incorporated by reference in its entirety herein, describes the EREFS score: Wechsler, Clin Hepatol. 2018 July; 16(7): 1056-1063.

In some embodiments, the patient's symptom score is evaluated using the Visual Dysphagia Question (VDQ). The VDQ addresses the severity of dysphagia when consuming food of 8 distinct consistencies. The 8 food consistencies and examples of foods to illustrate those consistencies are: 1) solid meat (such as steak, chicken, turkey, lamb), 2) soft foods (such as pudding, jelly, apple sauce), 3) dry rice or sticky Asian rice, 4) ground meat (hamburger, meatloaf), 5) fresh white untoasted bread or similar foods (such as doughnut, muffin, cake), 6) grits, porridge (oatmeal), or rice pudding, 7) raw fibrous foods (such as apple, carrot, celery), and 8) French fries. The degree of perceived difficulties when eating a given food consistency is graded between 0 for 'No difficulties' and 3 for 'Severe difficulties'. A VDQ composite score is calculated using the individual grades for a given food consistency. The VDQ composite score is the sum of the grades for each food consistency divided by the maximum sum of individual grades for each food consistency that could be attained. The maximum sum of grades depends on the number of food consistencies consumed by a subject in a given recall period. In some embodiments, the VDQ composite score is improved after treating according to the methods of the disclosure. An improvement in the VDQ composite score is a decrease in VDQ composite score. In some embodiments, the VDQ composite score is improved by between about 1 and about 24 points, for example, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 points.

In some embodiments, outcomes of the methods of the disclosure are evaluated using the EoE Activity Index (EEsAI) avoidance modification, and slow swallowing (AMS) score. In some embodiments the EEsAI is improved by about 2 to 15 points. In some embodiments, the EEsAI score is improved by about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4.0, or about 4.1, or about 4.2, or about 4.3, or about 4.4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0, or about 10.1, or about 10.2, or about 10.3, or about 10.4, or about 10.5, or about 10.6, or about 10.7, or about 10.8, or about 10.9, or about 11.0, or about 11.1, or about 11.2, or about 11.3, or about 11.4, or about 11.5, or about 11.6, or about 11.7, or about 11.8, or about 11.9, or about 12.0, or about 12.1, or about 12.2, or about 12.3, or about 12.4, or about 12.5, or about 12.6, or about 12.7, or about 12.8, or about 12.9, or about 13.0, or about 13.1, or about 13.2, or about 13.3, or about 13.4, or about 13.5, or about 13.6, or about 13.7, or about 13.8, or about 13.9, or about 14.0, or about 14.1, or about 14.2, or about 14.3, or about 14.4, or about 14.5, or about 14.6, or about 14.7, or about 14.8, or about 14.9, or about 15 points, inclusive of all ranges between these values.

In some embodiments of the disclosure, the global EoE score is utilized to evaluate the outcomes of the methods of the disclosure. In some embodiments, the EoE score is improved by 1 point to 4 points. In some embodiments, the EoE score is improved by about 1 point, or about 2 points, or about 3 points, or about 4 points. In some embodiments, the EoE score is improved by 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%, or about 125%, or about 150%, or about 175%, or about 200%, or about 225%, or about 250%, or about 275%, or about 300% or more, inclusive of all ranges between these values.

In some embodiments, the adult eosinophilic oesophagitis quality of life questionnaire (EoE-QoL-A) is utilized to evaluate the outcomes of the methods of the disclosure. The EoE-QoL-A) provides a measure of health-related quality of life. The EoE-QoL-A is a self-reported questionnaire designed to assess disease-specific health-related quality of life in adults with EoE. Questions are designed to evaluate established domains of health-related quality of life, including social functioning, emotional functioning, and disease impact on daily life experiences. The EoE-QoL-A includes 47 questions on a five point scale. Higher scores indicate a better quality of life. In some embodiments, the methods of the present disclosure result in an improvement in the EoE-QoL-A. In some embodiments, the EoE-QoL-A score is improved by about 1 to about 3 points.

In some embodiments, the patient global impression of severity (PGIS) is utilized to evaluate the outcomes of the methods of the disclosure. The PGIS is a global index that may be used to rate the severity of EoE. The PGIS is measured on a scale of 1 to 7. A score of 1 corresponds to normal, and a score of 7 corresponds to extremely ill. A score of 4 corresponds to moderately ill. In some embodiments, the methods of the disclosure result in a reduction in PGIS score. In some embodiments, the PGIS score shifts to improvement by about 1 to 5 severity categories (e.g., about 1, 2, 3, 4 or 5 categories). In some embodiments, the PGIS is reduced by 1 point, or 2 points, or 3 points, or 4 points, or 5 points. In some embodiments, the PGIC is reduced by about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%, inclusive of all ranges between these values.

In some embodiments, the patient global impression of change (PGIC) is utilized to evaluate the outcomes of the methods of the disclosure. The PGIC is a global index that may be utilized to assess an improvement or a decline in clinical status. The PGIC is measured on a scale of 1 to 7. A score of 1 corresponds to very much improved, and a score of 7 corresponds to very much worse. A score of 4 corresponds to no change in a patient's symptoms. In some embodiments, the methods of the disclosure result in a reduction in PGIC score. In some embodiments, the PGIC is reduced by 1 point, or 2 points, or 3 points, or 4 points, or 5 points, or 6 points, inclusive of all ranges between these values. In some embodiments, the PGIC is reduced by about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%, inclusive of all ranges between these values.

In embodiments, a reduction in eosinophil count is associated with an improvement in EoE. In some embodiments, the methods of the disclosure lead to a reduction in a patient's eosinophil count compared to the patient's baseline eosinophil levels. In some embodiments, the methods of the disclosure lead to an eosinophil count that is reduced to no more than 6 eosinophils per high power field (hpf). In some embodiments, the methods of the disclosure lead to an eosinophil count that is reduced to no more than 5 eosinophils per high power field (hpf), or 4 eosinophils per high power field (hpf), or 3 eosinophils per high power field (hpf), or 2 eosinophils per high power field (hpf), or 1 eosinophils per high power field (hpf). In some embodiments, the methods of the disclosure involve measurement of the eosinophil count in the distal portion of the esophagus, the proximal portion of the esophagus, or both. In some embodiments, the methods of the disclosure lead to an eosinophil count in the distal portion of the esophagus of no more than 6 eosinophils per hpf. In some embodiments, the methods of the disclosure lead to an eosinophil count in the distal portion of esophagus that is reduced to no more than 5 eosinophils per high power field (hpf), or 4 eosinophils per high power field (hpf), or 3 eosinophils per high power field (hpf), or 2 eosinophils per high power field (hpf), or 1 eosinophils per high power field (hpf). In some embodiments, the methods of the disclosure lead to an eosinophil count in the proximal portion of the esophagus of no more than 6 eosinophils per hpf. In some embodiments, the methods of the disclosure lead to an eosinophil count in the proximal portion of esophagus that is reduced to no more than 5 eosinophils per high power field (hpf), or 4 eosinophils per high power field (hpf), or 3 eosinophils per high power field (hpf), or 2 eosinophils per high power field (hpf), or 1 eosinophils per high power field (hpf).

In some embodiments, a symptom of EoE is dysphagia. In some embodiments, the methods of the disclosure lead to a decreased number of dysphagia episodes compared to a patient that is administered the corticosteroid twice daily. In some embodiments, the methods of the disclosure lead to an increased number of dysphagia-free days compared to a patient that is administered the corticosteroid twice daily

EXAMPLES

Example 1. Phase IIb Study (SP-1011-002)

A clinical trial (e.g., study SP-1011-002) was performed to evaluate the effect of an orally disintegrating table comprising fluticasone propionate (FP), called "APT-1011." Study SP-1011-002 is a Phase IIb, randomised, double-blind, placebo-controlled, multicentre, dose-ranging, and maintenance study of APT-1011 in subjects (≥18 and ≤75 years of age) with EoE. SP-1011-002 examined four doses of APT-1011 to define the exposure-response of APT-1011 and the minimum effective dose to minimize significant hypothalamic-pituitary-adrenal (HPA) axis effects. APT-1011 is expected to offer the following advantages for patients with EoE:

(a) Oral formulations are generally more acceptable and more reliable in terms of accurate dose administration. Currently, the only available pharmaceutical form of FP is an MDI approved for the treatment of asthma that is sprayed into the mouth instead of being inhaled and then swallowed by the patient.

(b) Oral administration of APT-1011 has very low bioavailability due to the extensive first-pass metabolism in the liver, particularly when compared with alternative corticosteroid products such as budesonide. As such, the potential for systemic corticosteroid toxicity remains low, while offering a more potent topical effect compared to budesonide on a mg to mg basis.

The Phase IIb study was designed as follows.

(a) Screening: Patients with a confirmed diagnosis or presumptive diagnosis of EoE were selected for the study. An EoE diagnosis was confirmed by symptoms, histology, and historical documentation of failed treatment on ≥8 weeks of high-dose proton pump inhibitor (PPI). A high-dose PPI was defined as administration of a total dose of 20 to 40 mg of a marketed PPI once or twice daily.

(b) 4 week single-blind placebo run in/baseline symptom assessment: To assess baseline symptoms, all subjects that passed the screening part of the study received a placebo 30 minutes after breakfast and hora somni (before sleep; HS) (at bedtime).

(c) Part 1 (induction) (studies the effect of APT-1011 over 14 weeks): Patients that entered Part 1 of the study had evidence of EoE as defined by ≥15 peak eosinophils/HPF. At least five to six biopsies should have been taken including both proximal and distal specimens.

(d) Part 2 (maintenance) studies the effect of use of APT-1011 from 14 weeks to 52 weeks.

Subjects that participated in Part 1 studies were randomized and administered a treatment selected from:

(a) 1.5 mg HS: Placebo 30 minutes after breakfast and 1.5 mg HS (at bedtime);

(b) 1.5 mg BID: 1.5 mg 30 minutes after breakfast and at bedtime; total daily dose of 3 mg;

(c) 3 mg HS: Placebo 30 minutes after breakfast and 3 mg at bedtime; and (d) 3 mg BID: 3.0 mg 30 minutes after breakfast and at bedtime; total daily dose of 6 mg.

During Part 1 (Induction, Day 1 to Week 14), subjects received their randomized treatment for 14 weeks. At Week 12, the subjects underwent a response assessment, including an oesophagogastroduodenoscopy (EGD) to assess endoscopic and histologic status. Histologic responders and non-responders (at Week 12) entered Part 2.

Figure 1:
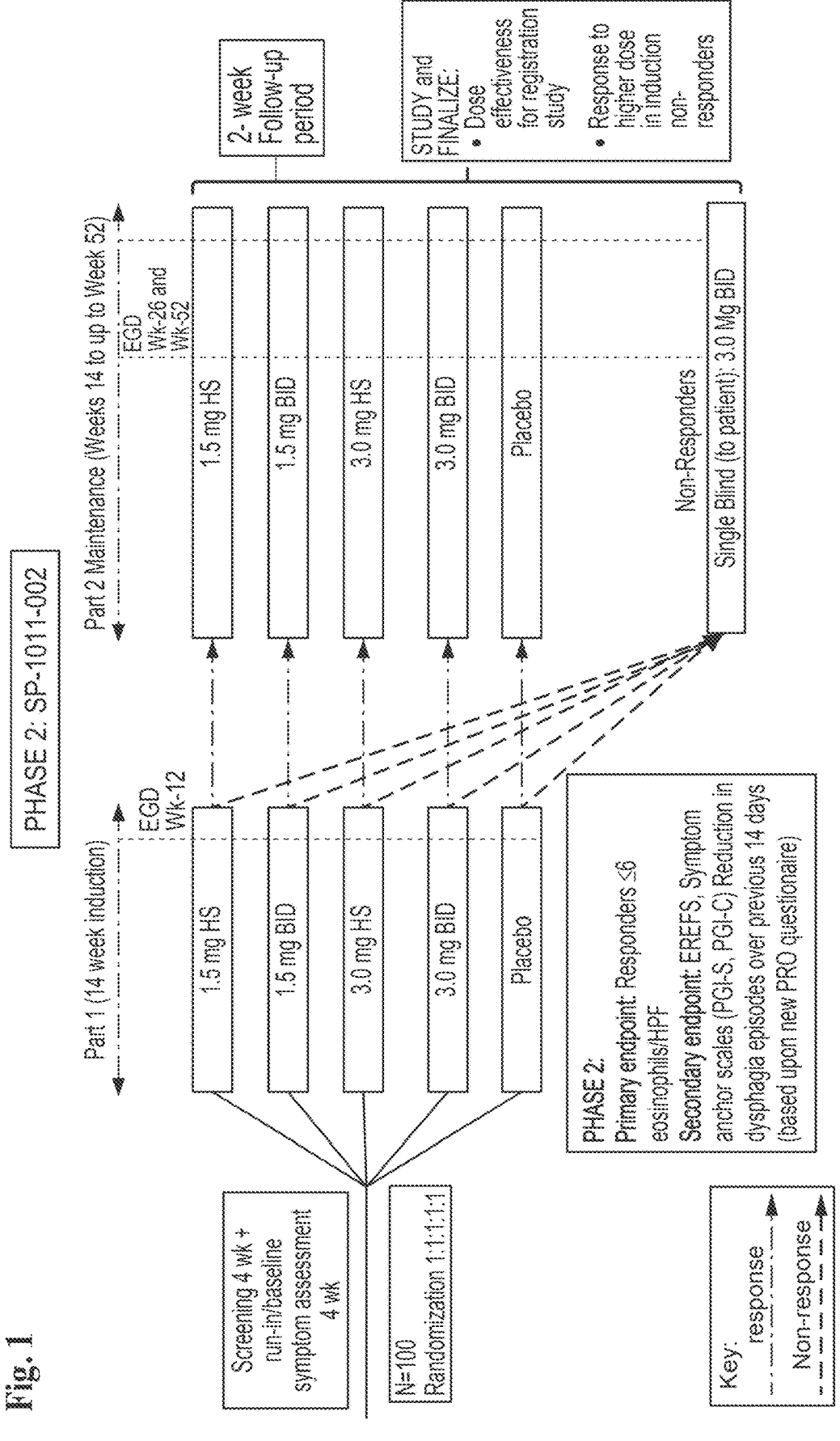
FIG. 1 depicts a schematic overview of the Phase II: SP-1011-002 corticosteroid studies.

In Part 2 (Maintenance, Weeks 14 to 52), all subjects classified as histologic responders at Week 12 continue to be treated according to the dosing group to which they were randomised for Part 1. Subjects can continue on this dose for up to 9 months after the completion of Part 1. Subjects who were histologic non-responders at Week 12 receive single-blind 3 mg BID in Part 2. A schematic overview of the study design is presented in FIG. 1.

Patient Population: 105 subjects received at least 1 dose of study drug in Part 1 of the study safety analysis set (SAF population), and 92 subjects (86.8%) of those subjects completed Week 14. The SAF population contained all subjects who were randomised and who did not meet any of the following criteria: subjects who did not receive any study drug, subjects given a wrong dose, or subjects mis-randomized. Subjects were classified according to their randomized treatment.

The subjects were on average 39.3 years old. There were more males than females and the majority of the subjects were white. The APT-1011 and placebo groups were similar in demographic and baseline characteristics. The mean BMI was similar across all treatment groups. There were no notable differences between the APT-1011 and placebo groups with respect to baseline disease characteristics.

The objectives of the study were as follows:

Primary Objective

The primary objective of the study was to evaluate the efficacy (histological response) of APT-1011 in adults with EoE.

Secondary Objectives:

To define the dose-response of APT-1011; To select a dose(s) of APT-1011 for Phase III; To evaluate the effect of APT-1011 on histology and endoscopic appearance; To evaluate maintenance of efficacy and long-term safety of APT-1011; To evaluate the population pharmacokinetics (PopPK) of APT-1011; To evaluate the effect of APT-1011 on dysphagia episodes.

Exploratory Objectives:

To evaluate the effect of APT-1011 on symptoms of EoE; To evaluate quality of life; To evaluate symptomatology over time; To evaluate the PK/PD relationship (with cortisol as the primary endpoint); To evaluate the dose-response relationship for the histological response and symptom response; To derive a scoring structure, and various endpoints from the Patient Reported Outcome Symptoms of EoE (PROSE); To evaluate the measurement properties of the PROSE, including reliability, construct validity, sensitivity to change; To produce guidelines for interpreting clinically meaningful change and derive the cut-off for treatment response on the PROSE, or a responder definition.

Endpoints:

Primary efficacy endpoints and secondary endpoints were measured.

The primary endpoint was the histologic responder rate at Week 12 of Part 1, defined as the percentage of subjects with ≤6 peak eosinophils/HPF after assessing at least 5 to 6 biopsies from the proximal and distal oesophagus (approximately 3 each) where the HPF area was 235 square microns (40 magnification lens with a 22 mm ocular).

The following secondary endpoints were evaluated through Week 12 for the interim analysis. Secondary endpoints included: EoE sustained response: Percentage of subjects who met the primary endpoint (histology) at Week 12 and maintained the primary endpoint at Weeks 26 and 52; Change from Baseline Eosinophilic Oesophagitis Endoscopic Reference Score (EREFS) at Weeks 12, 26, and 52: Endoscopic changes were as per the EREFS evaluation based on the following endoscopic features: Oedema, rings, exudates, furrows, stricture, and several miscellaneous features (crepe paper oesophagus, narrow calibre oesophagus, and oesophageal erosions); Percentage of subjects with a peak eosinophils/HPF number <1 and <15 at Weeks 12, 26, and 52; Change from Baseline Global EoE Symptom Score assessed prior to randomisation, which was assessed for the 7-day period prior to the following study visits: Weeks 4, 8, 12, 14, 18, 22, 26, 28, 36, 44, and 52; Dysphagia: Change in the number of dysphagia episodes at baseline (14-day period prior to randomisation) compared with the 14-day period prior to the time point of interest (Weeks 12, 26, and 52); Change from Baseline 7-day Eosinophilic Oesophagitis Activity Index (EEsAI) total score assessed prior to randomisation to those assessed at Weeks 12, 26, and 52; Change from Baseline 7-day EEsAI sub-scores to those assessed at Weeks 12, 26, and 52; Percentage of subjects with mean 7-day EEsAI total score <20 to those assessed at Weeks 12, 26, and 52; Change from Baseline Patient Global Impression of Severity (PGIS) assessed prior to randomisation at Weeks 4, 8, 12, 14, 18, 22, 26, 28, 36, 44, and 52; Patient Global Impression of Change (PGIC) at Weeks 4, 8, 12, 14, 18, 22, 26, 28, 36, 44, and 52; Assessment of treatment failure and relapse, including: Percentage of non-responders by dose at Weeks 12, 26, and 52; Percentage of subjects requiring emergency endoscopic food dis-impaction by dose before Week 14, between Week 14 and Week 28, and between Week 28 and Week 52; and Percentage of subjects requiring oesophageal dilation by dosing group and part of the study.

Exploratory efficacy endpoints were also analyzed. Exploratory efficacy endpoints include a change from Baseline in dysphagia-free days during the 14-day period prior to the following study visits: Weeks 12, 26, and 52; EoE sustained response (dysphagia): Percentage of all subjects who met the dysphagia secondary endpoint at Week 12 and maintained a dysphagia-related response at Week 26 and Week 52; Evaluation of PK/PD (cortisol) and exposure-response (efficacy) relationships; Subject's assessment of symptoms compared with the previous visit at Weeks 4, 8, 12, 14, 18, 22, 26, 28, 36, 44, 52, and the Early Termination Visit (if applicable); and Evaluation of Health-Related Quality of Life (HRQoL) based on the Adult Eosinophilic Esophagitis Quality of Life Questionnaire (EoE-QoL-A) at randomisation, Week 12, Week 26, Week 52 for all subjects by dose and subgroup.

Part 1 of study SP-1011-002 was completed, and efficacy and safety after 12 weeks of treatment with APT-1011 (1.5 mg HS, 1.5 mg BID, 3 mg HS, or 3 mg BID) or placebo are summarized below.

Primary Endpoint Results

Figure 2:
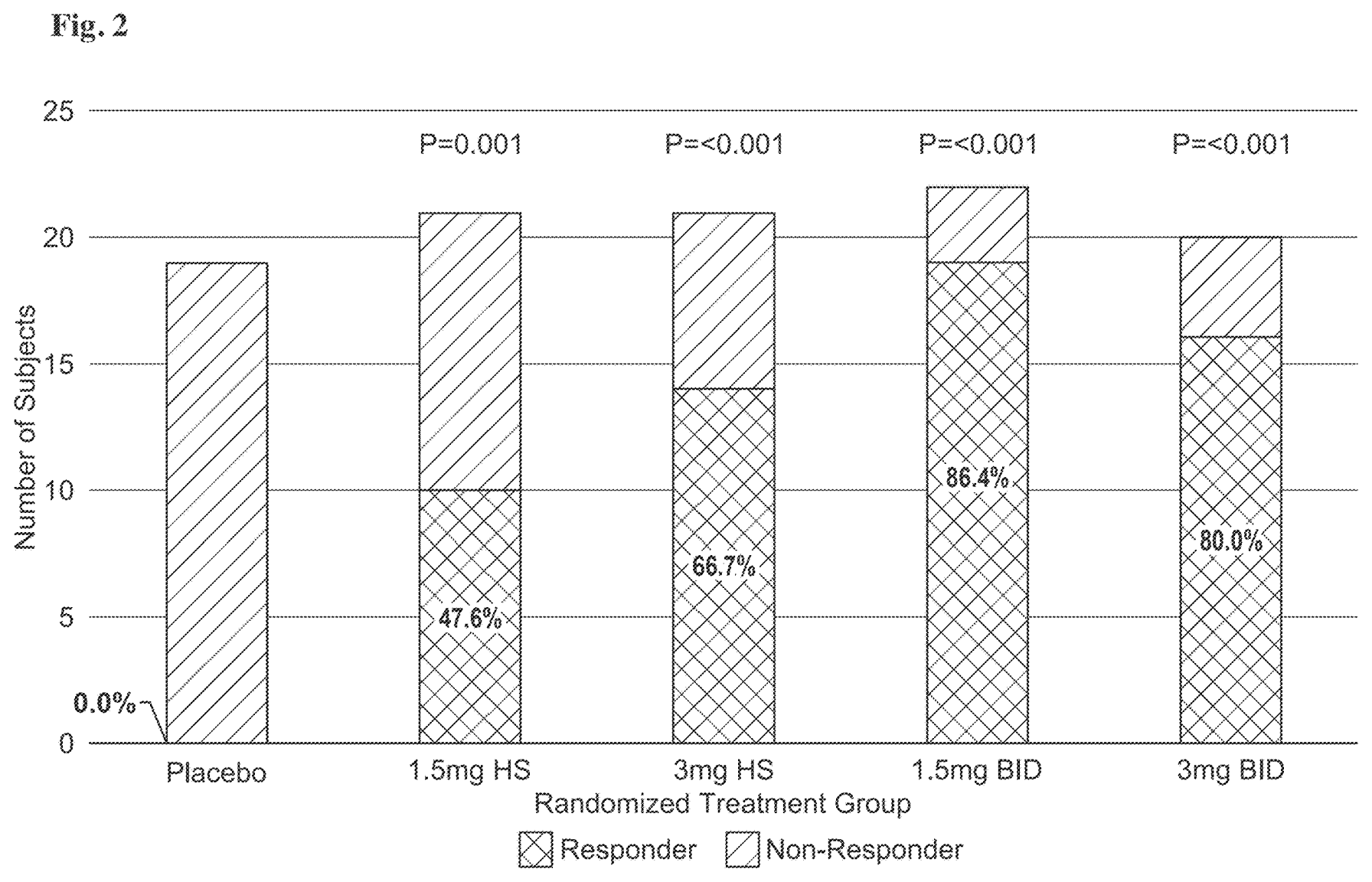

The primary endpoint, the EoE histologic response rate at Week 12 in the Full Analysis Set (FAS) population (N=103), was met at all APT-1011 doses versus placebo (FIG. 2 and Table 4). There were no histological responders in the placebo group. The primary analyses of the primary efficacy variable were repeated on the Per Protocol (PP) and Intent-to-Treat (ITT) analysis populations and there were no notable differences between the PP, ITT, and FAS populations. The 6 mg total daily dose (3 mg BID) did not provide additional benefit compared with the 3 mg total daily dose (3 mg HS or 1.5 mg BID) indicating that 3 mg per day is the minimally effective dose.

TABLE 4

| | EoE histologic response rate at Week 12 (FAS population) | | | | |
|---|---|---|---|---|---|
| | APT-1011 3 mg BID (N = 20) | APT-1011 3 mg HS (N = 21) | APT-1011 1.5 mg BID (N = 22) | APT-1011 1.5 mg HS (N = 21) | Placebo (N = 19) |
| Responder | 16 (80.0%) | 14 (66.7%) | 19 (86.4%) | 10 (47.6%) | 0 |
| Non-responder | 4 (20.0%) | 7 (33.3%) | 3 (13.6%) | 11 (52.4%) | 19 (100.0%) |
| 1-sided p-value | <0.001 | <0.001 | <0.001 | 0.001 | |

Abbreviations:
BID = twice a day,
CI = confidence interval,
EoE = eosinophilic esophagitis,
HS = hora somni (before sleep),
N = number,
N/A = not applicable.
Note:
Responder is defined as a subject with ≤6 peak eosinophils/HPF.
Note:
Common odds ratios, 90% Cis and 1-sided p-values are from a stratified Cochran Mantel-Haenzel (CMH) test comparing the response rate for each APT-1011 dose group with placebo. A gatekeeping strategy was used with tests performed in sequential order of doses from the following order (3 mg BID, 1.5 mg BID, 3 mg HS, 1.5 mg HS), with each test only performed if the previous test was significant at the 1-sided 0.05 significance level.
Note:
The strata used in the stratified CMH test were: History of or current presence of esophageal stricture (yes/no) and prior positive steroid response to any corticosteroid treatment previously received to treat EoE (yes/no).

Subjects receiving single-blind (to subject) treatment (3 mg twice daily [BID] in Part 2) will be tabulated separately: Percentage of subjects who were classified as histologic non-responders at Week 12 and have ≤6 peak eosinophils/HPF at all biopsied oesophageal locations at Week 26 and Week 52; Change from Baseline dysphagia episodes during the 14-day period prior to Week 26 and Week 52 for subjects who were classified as non-responders at Week 12; Percentage of subjects who were classified as histologic non-responders at Week 12 and meet the primary endpoint at Week 26 and Week 52.

A scoring structure, and various endpoints was derived from the PROSE; Psychometric measurement properties of the PROSE were evaluated; Anchor and distribution analyses to evaluate meaningful changes on the PROSE.

Safety endpoints were measured such as Frequency of treatment-emergent adverse event (TEAEs); TEAEs leading to discontinuation; Treatment-emergent serious adverse events (SAEs); Percentage of subjects with serum cortisol level ≤5 m/dL (≤138 nmol/L) or abnormal adrenocorticotropic hormone (ACTH) stimulation test (serum cortisol <16 μg/dL [≤440 nmol/L] at 60 minutes); The number of subjects discontinuing for HPA axis suppression will be recorded; and frequency of oral and oesophageal candidiasis.

Secondary Efficacy Endpoint Results

The following secondary efficacy endpoints were evaluated through Week 12 for the interim analysis: Change from Baseline in EREFs at Week 12, Percentage of subjects with a peak eosinophils/HPF number <1 and <15 at Week 12, Change from Baseline Global EoE Symptom Score assessed prior to randomisation, which was assessed for the 7-day period prior to the following study visits: Weeks 4, 8, and 12.

Change from Baseline in EREFS at Week 12

All APT-1011 dosing groups showed a statistically significant endoscopic remission measured as change from Baseline in EREFs total score at Week 12 based on the following endoscopic features: oedema, rings, exudates, furrows, stricture, and several miscellaneous features (crepe paper oesophagus, narrow calibre oesophagus, and oesophageal erosions).

Figure 3:
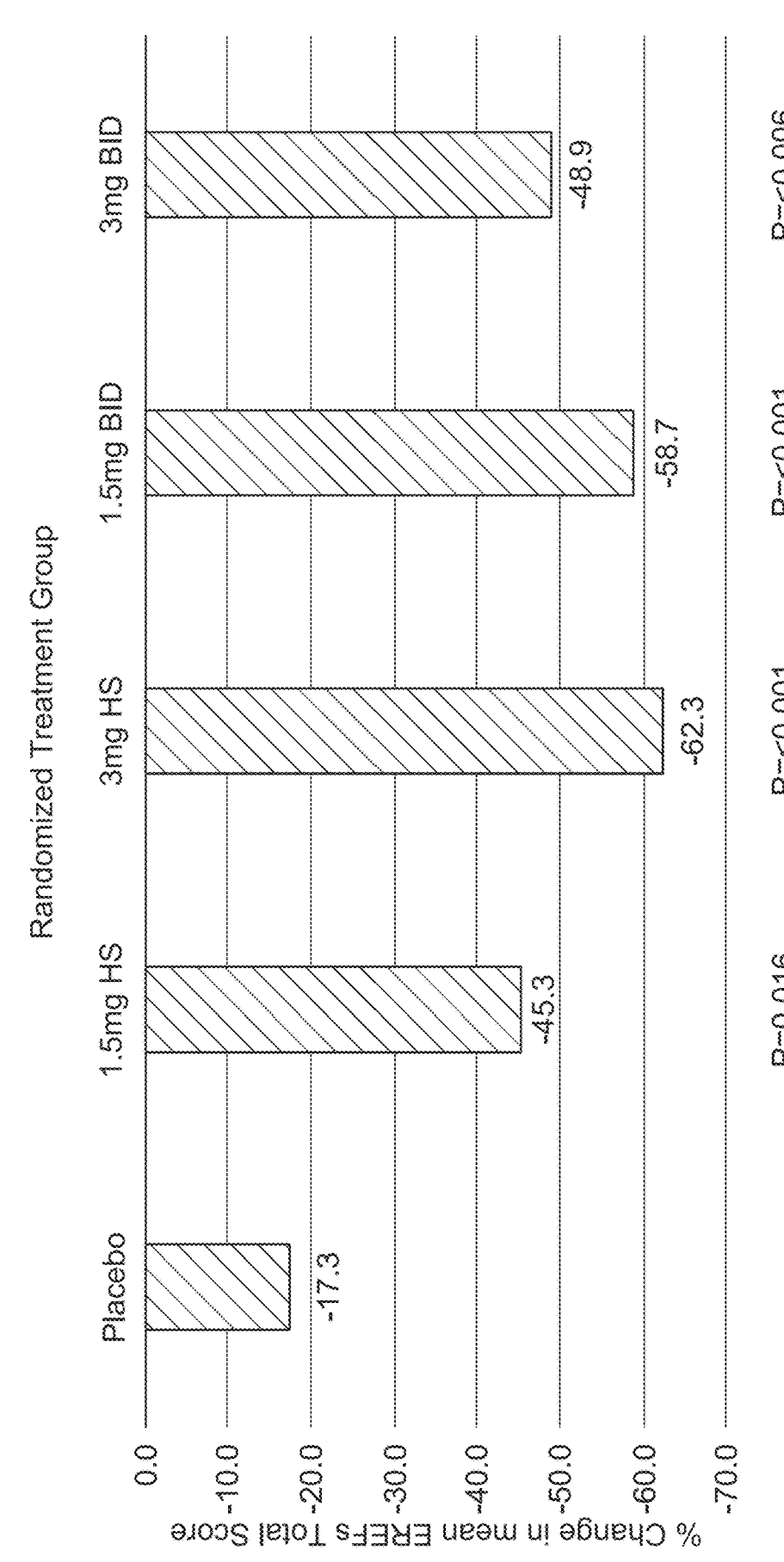
FIG. 3 depicts the percent change in mean EREFS total score from baseline at week 12 in the full analysis set population.

APT-1011 dosing groups, 3 mg HS and 1.5 mg BID showed the most improvement in EREFs compared with the other APT-1011 dosing groups supporting the 3 mg daily dose as the minimally effective dose (FIG. 3).

The mean baseline value for subjects with data at the visit and at baseline. Note: 1-sided p-values for comparisons of each APT-1011 dose group to Placebo at Week 12 are from an ANCOVA model including dosing group, history of or current presence of oesophageal stricture (yes/no), prior positive steroid response to any corticosteroid treatment previously received to treat EoE (yes/no), geographic region (North America/Western Europe), history of asthma/allergy (yes/no), and proton pump inhibitor status (Continuing into the study/Not continuing into the study) as factors, and EREF score at baseline as a covariate.

Percentage of Subjects with a Peak Eosinophils/HPF Number <1 and <15 at Week 12

All APT-1011 dosing groups were superior to placebo and there were no histological responders in the placebo group (Table 4).

Change from Baseline Global EoE Symptom Score Assessed Prior to Randomisation, which was Assessed for the 7-Day Period Prior to the Following Study Visits: Weeks 4, 8, and 12

APT-1011 HS dosing groups showed a greater trend in reducing the symptoms score compared with placebo than the APT-1011 BID dosing groups regardless of dose (Table 5).

TABLE 5

| | Change from Baseline in Global EoE Symptom Score at Week 12 (FAS population) | | | | |
|---|---|---|---|---|---|
| | APT-1011 3 mg BID (N = 20) | APT-1011 3 mg HS (N = 21) | APT-1011 1.5 mg BID (N = 22) | APT-1011 1.5 mg HS (N = 21) | Placebo (N = 19) |
| N | 18 | 20 | 21 | 17 | 16 |
| Visit Baseline[a] (mean) | 5.9 | 6.0 | 5.8 | 5.8 | 5.7 |
| Mean change | -1.7 | -3.1 | -1.6 | -3.2 | -1.8 |
| 1-sided p-value | 0.729 | 0.065 | 0.729 | 0.084 | |

The mean baseline value for subjects with data at the visit and at baseline.

Note:

1-sided p-values for comparisons of each APT-1011 dose group to Placebo at Week 12 are from an ANCOVA model including dosing group, history of or current presence of oesophageal stricture (yes/no), prior positive steroid response to any corticosteroid treatment previously received to treat EoE (yes/no), geographic region (North America/Western Europe), history of asthma/allergy (yes/no), and proton pump inhibitor status (Continuing into the study/Not continuing into the study) as factors, and EREF score at baseline as a covariate.

Dysphagia: Change in the Number of Dysphagia Episodes at Baseline (14-Day Period Prior to Randomisation) Compared with the 14-Day Period Prior to the Time Point of Interest (Week 12)

The number of dysphagia episodes at Baseline (14-day period prior to randomization) was compared with the 14-day period prior to Week 12. The APT-1011 3 mg HS, 3 mg BID and 1.5 mg HS dosing groups had better improvement compared with placebo and with the APT-1011 1.5 mg BID dosing group which had the least improvement overall (Table 6).

The change from Baseline to Week 12 in the number of dysphagia free days was highest in the APT-1011 1.5 mg HS dosing group (3.7), followed by APT-1011 3 mg HS (3.5) and 3 mg BID (3.4) compared with placebo (3.0), with the APT-1011 1.5 mg BID (0.2) dosing group having the least improvement overall.

TABLE 6

| | Change from Baseline in the number of dysphagia episodes at Week 12 (FAS population) | | | | |
|---|---|---|---|---|---|
| | APT-1011 3 mg BID (N = 20) | APT-1011 3 mg HS (N = 21) | APT-1011 1.5 mg BID (N = 22) | APT-1011 1.5 mg HS (N = 21) | Placebo (N = 19) |
| N | 19 | 20 | 21 | 18 | 17 |
| Visit Baseline[a] (mean) | 14.7 | 12.9 | 16.2 | 11.9 | 14.6 |
| Mean change | -9.1 | -9.3 | -4.4 | -8.2 | -5.5 |
| 1-sided p-value | 0.370 | 0.115 | 0.753 | 0.261 | |

The mean baseline value for subjects with data at the visit and at baseline.

Note:

1-sided p-values for comparisons of each APT-1011 dose group to Placebo at Week 12 are from an ANCOVA model including dosing group, history of or current presence of oesophageal stricture (yes/no), prior positive steroid response to any corticosteroid treatment previously received to treat EoE (yes/no), geographic region (North America/Western Europe), history of asthma/allergy (yes/no), and proton pump inhibitor status (Continuing into the study/Not continuing into the study) as factors, and EREF score at baseline as a covariate.

Change from Baseline in the 7-Day EEsAI Total Score and Sub Scores to Week 12

The improvement seen in the 7-day recall EEsAI scores in the APT-1011 3 mg HS and 3 mg BID dosing groups was similar and greater compared with the other APT-1011 dosing groups and placebo (Table 7).

The APT-1011 3 mg HS dosing group showed greater EEsAI total score improvement and greater Visual Dysphagia (VDQ) score improvement compared with placebo, and the second greatest improvement in the Avoidance, Modification, and Slow Eating (AMS) score, after the APT-1011 1.5 mg BID dosing group.

greater symptom improvement, however, the 1.5 mg HS dose did not address the underlying pathology as effectively as the 3 mg HS dose. Adverse event rates, particularly for candidiasis were low in both HS dosing groups and lower than the highest BID dosing group (see Safety section below); Systemic exposure was low across all doses. In totality, the APT-1011 3 mg HS dose provides the most favorable benefit-risk ratio.

Safety of APT-1011 after 12 Weeks Treatment in EoE Patients (Study SP-1011-002, Part 1)

The analyses of safety included the SAF population, and AEs were classified according to the MedDRA, Version

TABLE 7

| | Change from Baseline in the 7-day EEsAI total score at Week 12 (FASpopulation) | | | | |
| --- | --- | --- | --- | --- | --- |
| | APT-1011 3 mg BID (N = 20) | APT-1011 3 mg HS (N = 21) | APT-1011 1.5 mg BID (N = 22) | APT-1011 1.5 mg HS (N = 21) | Placebo (N = 19) |
| N | 19 | 20 | 20 | 18 | 17 |
| Visit Baseline[a] (mean) | 58.8 | 57.1 | 60.6 | 56.0 | 54.7 |
| Mean change | −22.6 | −22.7 | −15.6 | −20.4 | −9.6 |
| 1-sided p-value | 0.050 | 0.016 | 0.217 | 0.071 | |

The mean baseline value for subjects with data at the visit and at baseline.
Note:
1-sided p-values for comparisons of each APT-1011 dose group to Placebo at Week 12 are from an ANCOVA model including dosing group, history of or current presence of oesophageal stricture (yes/no), prior positive steroid response to any corticosteroid treatment previously received to treat EoE (yes/no), geographic region (North America/Western Europe), history of asthma/allergy (yes/no), and proton pump inhibitor status (Continuing into the study/Not continuing into the study) as factors, and EREF score at baseline as a covariate.

Change from Baseline Patient Global Impression of Severity (PGIS)/Patient Global Impression of Change (PGIC) Assessed Prior to Randomisation at Weeks 4, 8, and 12

The majority of subjects reported improvement overall. For all APT-1011 dosing groups at Week 12, the percentage of subjects in the "Much Improved" category was higher (25.0% to 45.0%) compared with the "Moderately Improved" category (15.0% to 29.4%), while the opposite was true in the placebo group, "Much Improved" (12.5%) and "Moderately Improved" (43.8%).

In summary, APT-1011 was superior to placebo in the treatment of EoE by demonstrating statistically significant and clinically relevant improvements in both primary and most secondary efficacy variables over a 12-week period (Part 1, Induction). These findings support the use of APT-1011 for the treatment of EoE for up to 12 weeks. The APT-1011 3 mg total daily dose is the most efficacious for both histological response and endoscopic appearance. Overall, the HS dosing groups showed the best trends for 21.0. Part 1 of the study was completed and the safety results at 12 weeks are summarised below. Treatment with APT-1011 3 mg BID, 3 mg HS, 1.5 mg BID, and 1.5 mg HS was safe and well tolerated in subjects with EoE disease during Part 1 of this study.

Brief Summary of Safety

A total of 63 (74.1%) subjects in the APT-1011 dosing group experienced at least 1 TEAE during the Part 1 of the study compared with 13 (65.0%) subjects in the placebo group (Table 8). The overall incidence of TEAEs that were reported as possibly or probably related to study drug was higher in the APT 1011 groups (24.7%) compared with the placebo group (20.0%). The majority of TEAEs were mild, followed by moderate in severity. There were no SAEs related to the study drug and no subject died. There was a higher incidence of AESIs in the APT-1011 dosing groups compared with the placebo group. In Part 1 of the study, no subject experienced HPA axis suppression as determined by abnormal ACTH stimulation tests.

TABLE 8

| | Overall summary of TEAEs during Part 1 (SAF population) | | | | | |
| --- | --- | --- | --- | --- | --- | --- |
| TEAE Category | APT-1011 3 mg BID (N = 20) n (%) | APT-1011 3 mg HS (N = 21) n (%) | APT-1011 1.5 mg BID (N = 23) n (%) | APT-1011 1.5 mg HS (N = 21) n (%) | Placebo (N = 20) n (%) | Total APT-1011 (N = 85) n (%) |
| TEAE | 17 (85.0%) | 16 (76.2%) | 17 (73.9%) | 13 (61.9%) | 13 (65.0%) | 63 (74.1%) |
| Maximum severity of TEAE | | | | | | |
| Mild | 12 (60.0%) | 6 (28.6%) | 14 (60.9%) | 11 (52.4%) | 10 (50.0%) | 43 (50.6%) |
| Moderate | 5 (25.0%) | 9 (42.9%) | 3 (13.0%) | 1 (4.8%) | 3 (15.0%) | 18 (21.2%) |

TABLE 8-continued

| | Overall summary of TEAEs during Part 1 (SAF population) | | | | | |
|---|---|---|---|---|---|---|
| TEAE Category | APT-1011 3 mg BID (N = 20) n (%) | APT-1011 3 mg HS (N = 21) n (%) | APT-1011 1.5 mg BID (N = 23) n (%) | APT-1011 1.5 mg HS (N = 21) n (%) | Placebo (N = 20) n (%) | Total APT-1011 (N = 85) n (%) |
| Severe | 0 | 1 (4.8%) | 0 | 1 (4.8%) | 0 | 2 (2.4%) |
| TEAE related to study drug | 10 (50.0%) | 4 (19.0%) | 5 (21.7%) | 2 (9.5%) | 4 (20.0%) | 21 (24.7%) |
| TEAE leading to study discontinuation | 1 (5.0%) | 0 | 2 (8.7%) | 0 | 2 (10.0%) | 3 (3.5%) |
| Serious TEAE | 0 | 1 (4.8%) | 0 | 0 | 0 | 1 (1.2%) |
| TEAE resulting in death | 0 | 0 | 0 | 0 | 0 | 0 |
| TEAE of special interest | 7 (35.0%) | 1 (4.8%) | 3 (13.0%) | 0 | 0 | 11 (12.9%) |

Abbreviations:
BID = twice a day,
HS = hora somni (before sleep),
N = number,
n = subject count,
TEAE = treatment-emergent adverse event.
Note:
TEAE = any adverse event that started or worsened in severity after the first dose of study drug in Part 1 of the study and prior to first dose of study drug in Part 2.
Note:
For maximum severity rows, if a subject has more than 1 TEAE, they are counted only once based on the maximum severity. "Total APT-1011" refers to all subjects on active treatment.

Analysis of Adverse Events

The most frequently reported system organ class (SOC) in the pooled APT-1011 dosing groups was infections and infestations, 36 (42.4%) subjects, particularly at the highest total daily doses (Table 9). The second most frequently reported SOC in the pooled APT-1011 dosing group was GI disorders, 23 (27.1%) subjects, particularly at the highest total daily doses. At the preferred term (PT) level, the most frequently reported TEAE was nasopharyngitis and oesophageal candidiasis, particularly at the highest total daily doses (Table 9).

TABLE 9

| | TEAEs ≥10% in APT-1011 dosing group during Part 1 by SOC and PT (SAF population) | | | | | |
|---|---|---|---|---|---|---|
| System organ class Preferred term | APT-1011 3 mg BID (N = 20) n (%) | APT-1011 3 mg HS (N = 21) n (%) | APT-1011 1.5 mg BID (N = 23) n (%) | APT-1011 1.5 mg HS (N = 21) n (%) | Placebo (N = 20) n (%) | Total APT-1011 (N = 85) n (%) |
| Number of subjects with at least 1 TEAE | 17 (85.0%) | 16 (76.2%) | 17 (73.9%) | 13 (61.9%) | 13 (65.0%) | 63 (74.1%) |
| Number of TEAEs | 44 | 35 | 34 | 40 | 27 | 153 |
| Number of subjects with at least 1 TEAE by SOC and PT | | | | | | |
| Infections and infestations | 14 (70.0%) | 8 (38.1%) | 10 (43.5%) | 4 (19.0%) | 3 (15.0%) | 36 (42.4%) |
| Nasopharyngitis | 0 | 2 (9.5%) | 3 (13.0%) | 3 (14.3%) | 2 (10.0%) | 8 (9.4%) |
| Oesophageal candidiasis | 6 (30.0%) | 0 | 2 (8.7%) | 0 | 0 | 8 (9.4%) |
| Oral candidiasis | 2 (10.0%) | 1 (4.8%) | 2 (8.7%) | 0 | 0 | 5 (5.9%) |
| Vulvovaginal mycotic infection | 2 (10.0%) | 0 | 0 | 0 | 0 | 2 (2.4%) |
| Gastrointestinal disorders | 5 (25.0%) | 9 (42.9%) | 6 (26.1%) | 3 (14.3%) | 4 (20.0%) | 23 (27.1%) |
| Investigations | 3 (15.0%) | 1 (4.8%) | 3 (13.0%) | 1 (4.8%) | 3 (15.0%) | 8 (9.4%) |
| Musculoskeletal and connective tissue disorders | 2 (10.0%) | 1 (4.8%) | 2 (8.7%) | 3 (14.3%) | 0 | 8 (9.4%) |
| Back pain | 2 (10.0%) | 1 (4.8%) | 0 | 2 (9.5%) | 0 | 5 (5.9%) |
| Nervous system disorders | 3 (15.0%) | 2 (9.5%) | 1 (4.3%) | 2 (9.5%) | 2 (10.0%) | 8 (9.4%) |
| Headache | 3 (15.0%) | 1 (4.8%) | 1 (4.3%) | 1 (4.8%) | 2 (10.0%) | 6 (7.1%) |
| Injury, poisoning and procedural complications | 2 (10.0%) | 2 (9.5%) | 1 (4.3%) | 1 (4.8%) | 0 | 6 (7.1%) |

TABLE 9-continued

| | TEAEs ≥10% in APT-1011 dosing group during Part 1 by SOC and PT (SAF population) | | | | | |
|---|---|---|---|---|---|---|
| System organ class<br>Preferred term | APT-1011<br>3 mg BID<br>(N = 20)<br>n (%) | APT-1011<br>3 mg HS<br>(N = 21)<br>n (%) | APT-1011<br>1.5 mg BID<br>(N = 23)<br>n (%) | APT-1011<br>1.5 mg HS<br>(N = 21)<br>n (%) | Placebo<br>(N = 20)<br>n (%) | Total<br>APT-1011<br>(N = 85)<br>n (%) |
| Respiratory, thoracic and mediastinal disorders | 1 (5.0%) | 0 | 1 (4.3%) | 4 (19.0%) | 2 (10.0%) | 6 (7.1%) |
| Psychiatric disorders | 2 (10.0%) | 1 (4.8%) | 0 | 1 (4.8%) | 0 | 4 (4.7%) |

Abbreviations:
AE = adverse event;
BID = twice a day;
HS = hora somni (before sleep);
MedDRA = Medical Dictionary for Regulatory Activities;
N = number;
PT = Preferred Term;
SOC = System Organ Class;
TEAE = treatment-emergent adverse event.
Note:
TEAE = any adverse event that started or worsened in severity after the first dose of study drug in Part 1 of the study and prior to first dose of study drug in Part 2.
Note:
AEs were coded to SOC and PT using MedDRA Version MEDDRA211_MIXED.
Note:
"Total APT-1011" refers to all subjects on active treatment.

Deaths, Serious Adverse Events, and Other Significant Adverse Events:

No deaths were reported during the Part 1 of the study (Table 8). One subject in the pooled APT-1011 dosing groups experienced 1 serious TEAE of ureterolithiasis due to the worsening symptoms of obstructing ureteral stone; and the TEAE was not considered to be related to the study drug.

Adverse Events Leading to Discontinuation:

Three (3.5%) subjects in the pooled APT-1011 dosing groups and 2 (10.0%) subjects in the placebo group discontinued due to an AE during Part 1 of the study (Table 8). The AEs that resulted in discontinuation included oral candidiasis, oesophageal candidiasis, and oesophageal food impaction in the APT-1011 dosing groups.

Other Clinically Relevant Adverse Events (AESI)s:

The primary AESIs were those AEs related to HPA axis suppression. There were no AEs of HPA axis suppression, abnormal ACTH stimulation test results, or symptoms of hypercorticism. Oral and oesophageal candidiasis were also considered AESIs. The overall incidence of AESIs was higher in the APT-1011 dosing groups compared with the placebo group (Table 10). Within the APT-1011 dosing groups, the 3 mg BID dosing group had a higher incidence of AESIs. The lowest incidence was observed with the HS dosing groups. The majority of AESIs were mild and none were severe in severity.

TABLE 10

| | TEAEs of special interest during Part 1 by SOC and PT (SAF population) | | | | | |
|---|---|---|---|---|---|---|
| System organ class<br>Preferred term | APT-1011<br>3 mg BID<br>(N = 20)<br>n (%) | APT-1011<br>3 mg HS<br>(N = 21)<br>n (%) | APT-1011<br>1.5 mg BID<br>(N = 23)<br>n (%) | APT-1011<br>1.5 mg HS<br>(N = 21)<br>n (%) | Placebo<br>(N = 20)<br>n (%) | Total<br>APT-1011<br>(N = 85)<br>n (%) |
| Number of subjects with TEAEs of special interest | 7 (35.0%) | 1 (4.8%) | 3 (13.0%) | 0 | 0 | 11 (12.9%) |
| Number of TEAEs of special interest | 8 | 1 | 5 | 0 | 0 | 14 |
| Number of subjects with at least 1 TEAE of special interest by SOC and PT | | | | | | |
| Infections and infestations | 7 (35.0%) | 1 (4.8%) | 3 (13.0%) | 0 | 0 | 11 (12.9%) |
| Oesophageal candidiasis | 5 (25.0%) | 0 | 2 (8.7%) | 0 | 0 | 7 (8.2%) |
| Oral candidiasis | 2 (10.0%) | 1 (4.8%) | 2 (8.7%) | 0 | 0 | 5 (5.9%) |
| Oropharyngeal candidiasis | 1 (5.0%) | 0 | 0 | 0 | 0 | 1 (1.2%) |

Abbreviations:
Ae = adverse event;
BID = twice a day;
HS = hora somni (before sleep);
MedDRA = Medical Dictionary for Regulatory Activities;
PT = Preferred Term;
N = number;
SOC = System Organ Class;

TABLE 10-continued

| TEAEs of special interest during Part 1 by SOC and PT (SAF population) | | | | | | |
|---|---|---|---|---|---|---|
| System organ class<br>Preferred term | APT-1011<br>3 mg BID<br>(N = 20)<br>n (%) | APT-1011<br>3 mg HS<br>(N = 21)<br>n (%) | APT-1011<br>1.5 mg BID<br>(N = 23)<br>n (%) | APT-1011<br>1.5 mg HS<br>(N = 21)<br>n (%) | Placebo<br>(N = 20)<br>n (%) | Total<br>APT-1011<br>(N = 85)<br>n (%) |

TEAE = treatment-emergent adverse event.

Note:

TEAE = any adverse event that started or worsened in severity after the first dose of study drug in Part 1 of the study and prior to first dose of study drug in Part 2.

Note:

AEs were coded to SOC and PT using MedDRA Version MEDDRA211_MIXED.

Note:

"Total APT-1011" refers to all subjects on active treatment.

Clinical Laboratory Evaluation:

There were no trends of abnormal safety signals related to laboratory values. No relevant treatment group differences were noted for any laboratory parameter.

Vital Signs, Physical Examination Findings and Other Observations Related to Safety:

Analyses of vital sign and physical findings did not reveal any clinically relevant effect of APT-1011 treatment.

Safety Results in a 24-Hour Follow Up Period after Discontinuation of Treatment (Study PR-022):

Out of 22 subjects that completed the Study PR-021, 14 subjects enrolled in PR-022 study where they received no treatment with APT-1011. All subjects completed the study and were analysed for safety. Twelve subjects experienced 59 post-APT-1011 treatment adverse events (PTAEs) and of those 12 subjects, 9 experienced 30 PTAEs after receiving APT-1011 and 3 experienced 29 TEAEs after receiving placebo. No subjects had PTAEs that were possibly related to study drug as determined by the investigator or PTAEs of special interest, including hypercorticism, a predefined AE of special interest. In total 11 subjects experienced 47 newly occurring AEs. There were no SAEs or deaths in this study.

The most common AEs experienced by at least 2 subjects who received APT-1011 were diarrhoea and nasopharyngitis. The most common newly occurring AE was arthralgia (2/14 subjects, 14.3%). The majority of PTAEs were of mild severity (47/59 PTAEs). No subject experienced a TEAE that led to discontinuation of study drug.

Mean changes from baseline laboratory parameters at Week 8, Week 16, Week 24 and Final Evaluation were generally small and not clinically meaningful in any treatment group. Changes from baseline values in laboratory parameters that resulted in shifts in or out of normal laboratory reference ranges were generally infrequent. For any laboratory parameters, shifts from baseline values out of normal laboratory reference ranges were not observed by more than 1 subject. None of the subjects had significant abnormalities to be considered as AEs of special interest. Mean changes from baseline vital signs measurements at Week 8, Week 16, Week 24 and at Final Evaluation were generally small and not clinically meaningful in each treatment group Safety Results after APT-1011 Treatment of Healthy Volunteers (Study PR-023 and SP1011-011):

The administration of a single dose of APT-1011 (6 mg) in male and female healthy adult volunteers was safe and well tolerated when administered under fasted, fed, or bed-time conditions (Study SP-1011-001). No AESIs, no SAEs, and no deaths were reported for any of the subjects enrolled in this study. No subject was withdrawn by the investigator for safety reasons. The TEAEs reported in this study were experienced with a low incidence; drug-related TEAEs were reported with a similar trend as the total TEAE incidence: 9% for Treatment A (morning fast), 5% for Treatment B (morning fed), and 17% for Treatment C (at bedtime, HS). Furthermore, none of the subjects had clinically significant abnormal values in AM cortisol, urinalysis, vital signs, and electrocardiogram.

APT-1011 was also generally well tolerated by healthy volunteers after multiple dosing conditions (fasting and fed) and regimens (3 mg BID and 6 mg QD) were investigated (Study PR-023). No significant study drug-related safety issues were identified that would preclude further clinical investigation. All AEs were mild in severity, and none of the events were deemed to be treatment-related AEs. No severe or serious adverse events occurred, and no deaths were reported. One subject withdrew from the study, but the withdrawal was not associated with adverse events from the study drug. No clinically significant study drug-related changes from baseline were noted in routine haematology or serum chemistry panels, complete blood count, vital signs, electrocardiogram, or physical examinations.

Completed Clinical Studies in Paediatric Population (Study PR-021):

The completed study PR-021 included 8 patients between 12-17 years. This study was conducted in US in 2011-2012 with in total 24 patients randomized to 3 groups (8 per group). Two adolescents received placebo and 6 active treatment (1.5 mg BID or 3.0 mg QD). The results of the study demonstrated a signal of efficacy based upon histologic and overall symptom improvement. Overall adverse event reports, routine safety laboratory assessments, and physical examinations did not evidence any safety concerns. The number of subjects in this study was too small to evaluate efficacy or safety in subsets.

Safety and Efficacy of APT-1011 in Part 2 (Weeks 26 and 52)

Part 2 of the study provides placebo-controlled data to confirm the maintenance of efficacy and long-term safety of APT-1011 over a treatment period of 52 weeks in patient with EoE. Sixteen (16) subjects in the placebo group in Part 1 entered Part 2 and received the single-blind 3 mg BID dose. Of the pooled APT-1011 groups, 17 histologic non-responders received the single-blind 3 mg BID dose in Part 2. The remaining subjects continued to be treated in Part 2 according to their blinded Part 1 dosing regimen.

Figures 4A, 4B:
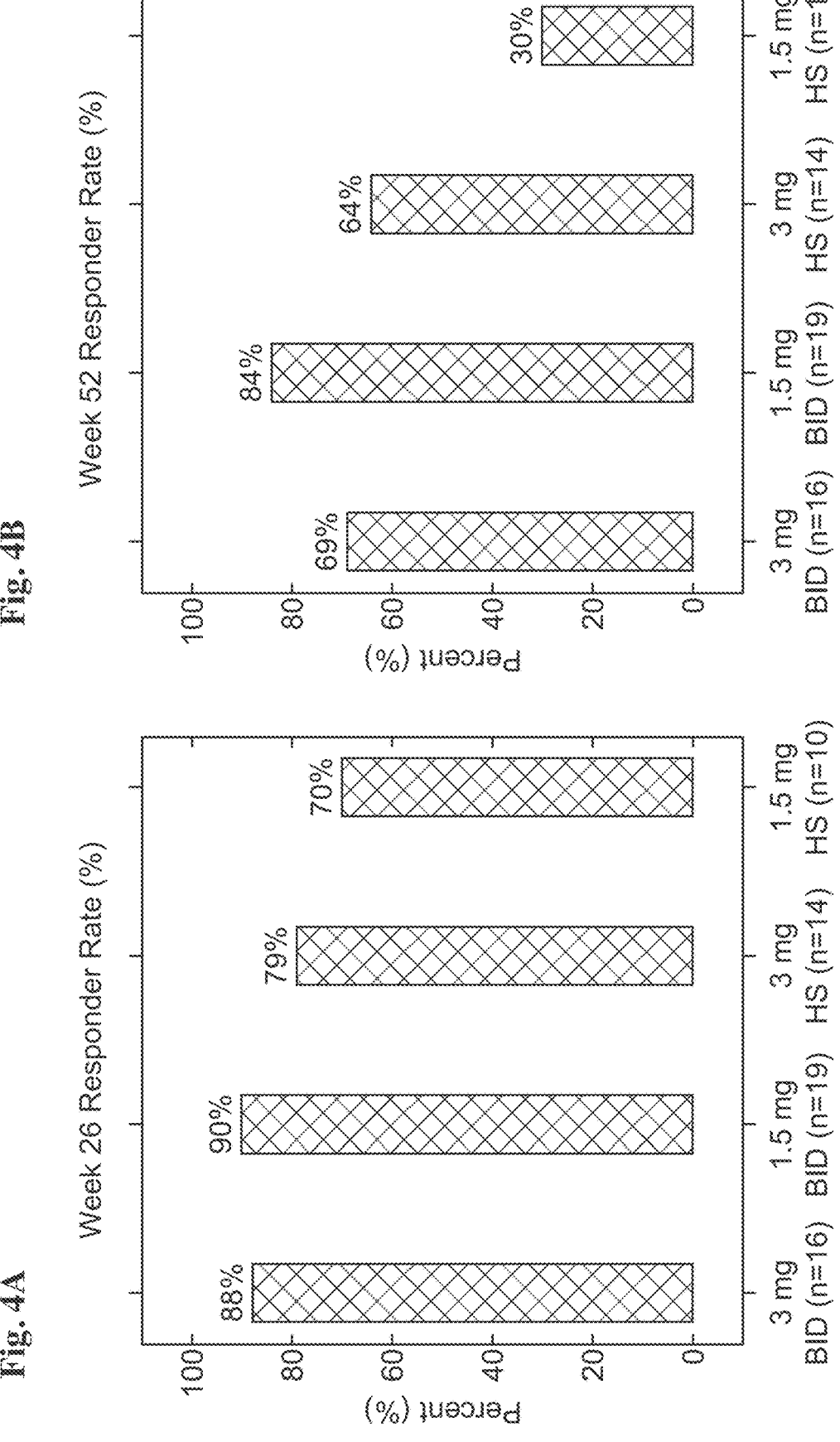
FIG. 4A depicts the EoE histologic response rate at week 26.
FIG. 4B depicts the EoE histologic response rate at week 52. Responder=histological responder defined as a subject with ≤6 peak eosinophils/high-power field (HPF); BID=twice daily; HS=hora somni (at bedtime).

Subjects determined to be histological responders in part 1 of the study were administered maintenance doses as described herein. A histological responder was defined as a subject with ≤6 peak eosinophils/high-power field (HPF). Histological response rate was measured after week 26 and week 52. These results are presented in FIG. 4A and FIG. 4B, respectively.

Figure 5A:
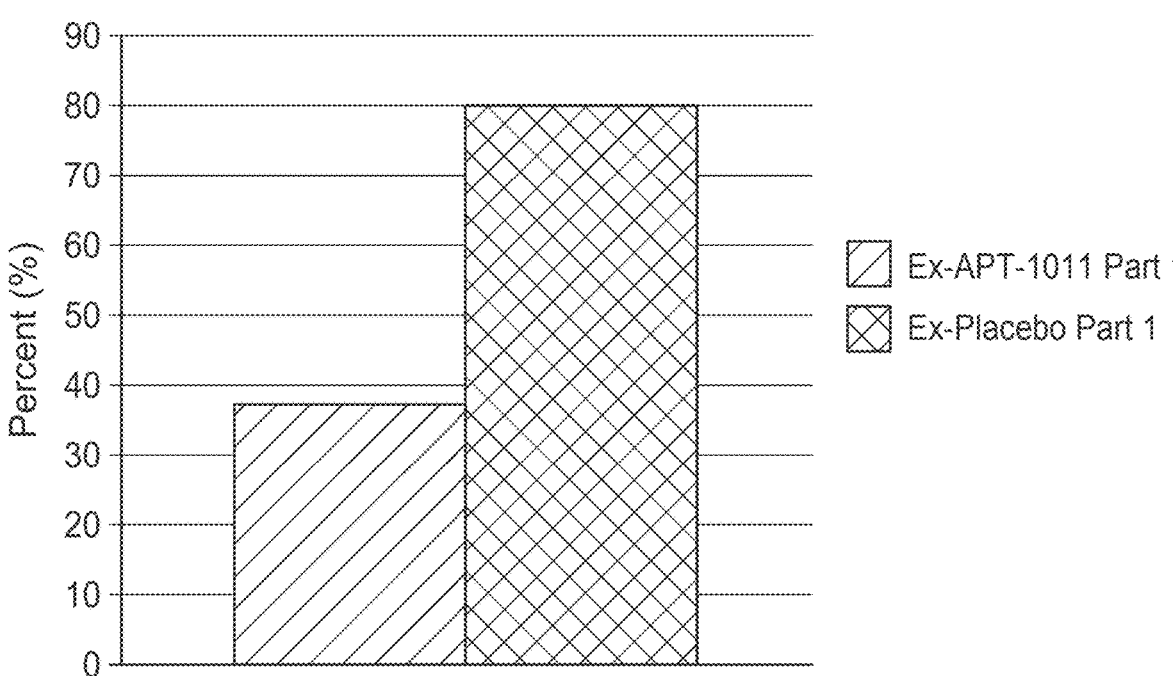
FIG. 5A depicts the histological response at EoE histologic response rate at week 26.
Figure 5B:
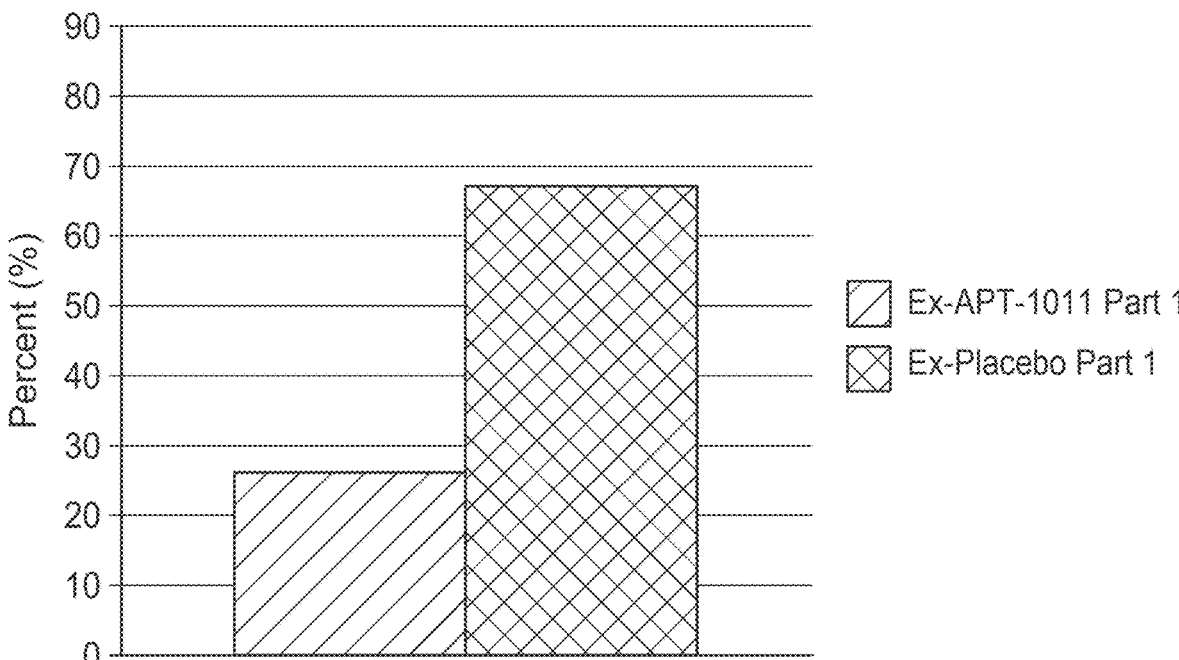
FIG. 5B depicts the histological response at EoE histologic response rate at week 52.

Histological non-responders from part 1 of the study (at week 12) were administered 3 mg BID. Histological responder rates were measured at weeks 26 and 52, and these results are presented in FIG. 5A and FIG. 5B, respectively.

Various clinically relevant end points were measured throughout the course of the 52 week study. Data are displayed for all groups to Week 12, and thereafter only for histological responders. All responders at Week 12 continued double-blind randomized dosing regimen in Part 2. Histological non-responders at Week 26 exited the study per protocol.

FIG. 6 shows endoscopic severity scores measured by EREFS over 52 weeks. All APT-1011 dosing regimens showed greater reduction in endoscopic severity measures by EREFs Scores as compared to placebo at Week 12. This improvement continued through Week 52.

FIG. 7 shows the reduction in episodes of dysphagia over 52 weeks. All APT-1011 dosing regimens, except 1.5 mg BID, showed greater reduction in mean number of dysphagia episodes as compared to placebo at Week 12. This improvement continued through Week 52.

FIG. 8 shows the reduction in global EoE scores over 52 weeks. Only the HS APT-1011 dosing regimens showed greater reduction in Global EoE Scores as compared to placebo at Week 12. This improvement continued through Week 52.

A comparison of the part 1 and part 2 safety data is shown in Table 11 and Table 12 below. 1 subject (3 mg BID) had reported adrenal suppression at Week 52 with falling cortisol 2-weeks off study drug. Concomitant meds included 19-nortestosterone 2-weeks off study drug; 1 subject (3 mg HS) had reported abnormal ACTH stimulation test at Week 52; follow-up normal. FIG. 9 compares the incidence rates of candidiasis (esophageal, oral, and oropharyngeal) in part 1 and part 2 of the study.

TABLE 21

| Part 1 Safety Data | | |
| --- | --- | --- |
| Part 1 | APT-1011 Total (N = 84) | Placebo (N = 19) |
| Subjects with ≥1 TEAE | 63 (74.1%) | 13 (65.0%) |
| Serious TEAE | 1 (3.6%) | 0 |
| Deaths | 0 | 0 |
| TEAEs with >5% Frequency* | | |
| Esophageal candidiasis | 8 (9.4%) | 0 |
| Oral Candidiasis | 5 (5.9%) | 0 |
| Dyspepsia | 5 (5.9%) | 1 (5.0%) |
| Back Pain | 5 (5.9%) | 0 |

*higher frequency in APT-1011 total groups vs. placebo

TABLE 32

| Part 2 Safety Data | |
| --- | --- |
| Part 2 | APT-1011 Total (N = 93) |
| Subjects with ≥1 TEAE | 68 (73.1%) |
| Serious TEAE | 2 (2.2%) |
| Deaths | 0 |
| TEAEs with >5% Frequency | |
| Nasopharyngitis | 12 (12.9%) |
| Headache | 7 (7.5%) |
| Esophageal candidiasis | 5 (5.4%) |

TABLE 32-continued

| Part 2 Safety Data | |
| --- | --- |
| Part 2 | APT-1011 Total (N = 93) |
| Oral Candidiasis | 5 (5.4%) |
| Upper Respiratory Tract Infection | 5 (5.4%) |
| Cortisol decreased^ | 5 (5.4%) |

^repeat testing normal for all subjects; no associated adrenal suppression

Example 2

Pharmacokinetic, Pharmacodynamics, and Efficacy Studies (Study PR-023 and SP-1011-001, PR-021)

Study SP-1011-001 demonstrated that systemic exposure of FP is very low (pg/mL concentrations) following oral APT-1011 single dose administration (total dose 6 mg) under fast, fed and at bedtime dosing. The lower limit of quantitation of the very sensitive analytical method used was 0.5 pg/mL. Maximal concentrations were 31, 34 and 24 pg/ml (geo.mean) under fast, fed and at bedtime dosing respectively. The interindividual variability (CV %) for Cmax was over 100% for all three regimens.

Following repeat-dose administration of APT-1011 (6 mg once-daily ("QD") or 3 mg BID), apparent steady-state exposure of FP was attained within 4 days based on visual examination of trough concentration-time profiles for individual subjects (Study PR-023). There was no discernible difference between steady-state, systemic exposure of APT-1011 for a 6 mg QD or 3 mg BID dosing regimen.

At steady-state, systemic exposure of APT-1011 for the 6 mg QD dosing regimen and the 3 mg BID dosing regimen were as follows: geometric mean AUCτ estimates of 500 (80.8) h·pg/ml for BID dosing and 471 (30.0) h·pg/ml for QD dosing. Maximal plasma concentrations were 38.4 (69.2) pg/ml and 34.7 (26.2) pg/ml respectively.

This Phase I PK study confirmed that systemic exposure of FP is low following administration of orally administered FP (APT-1011 up to a total daily dose of 6.0 mg). These data are consistent with a reported oral bioavailability of FP as less than 1%.

Small food effects were observed on both Cmax and AUC ratios after single dosing under fast, fed and at bedtime dosing. For morning dosing, Cmax, AUClast and AUCinf Test Fed/Test Fast ratios were 120.65%, 76.97% and 71.10% respectively, while Cmax, AUClast and AUCinf Test Bed-Time/Test Fed ratios were 67.79%, 120.03 and 122.36%, respectively. Administration of a single dose APT-1011 following a high-fat meal was associated with a 41% decrease in AUC(0-24 h) and 30% decrease in Cmax of FP, indicating that food influences the absorption of oral FP. When a subject in the fasted arm with very high exposures was excluded as part of a post-hoc exploratory analysis, food was associated with a 31% decrease in AUC (0-24 h) and a 18% decrease in Cmax. The oral bioavailability is very low (<200 ng/mL on the individual level (assay sensitivity 0.5 pg/mL)) with mean values of 42.0 48.5 and 35.3 pg/mL for fast, fed and HS treatment respectively.

The observed extent of cortisol suppression was substantially less than the pre-defined threshold of clinical concern in this study (35% suppression). At steady-state of drug exposure, mean serum cortisol suppression was 5.51% (QD regimen) and 10.8% (BID regimen) relative to baseline (Day 0), with SD of 13.4% and 15.3%, respectively.

Changes in spot urinary cortisol levels were associated with substantially greater between-subject variability than serum cortisol levels. Despite this greater variability, the trend for spot urinary cortisol changes was similar to that observed in serum. At steady state of drug exposure, based on spot urine samples, mean urinary cortisol suppression was 1.1% (QID regimen) and 16% (BID regimen) relative to baseline (Day 0), with SD of 21% and 33%, respectively.

Efficacy of APT-1011 after 8 Weeks Treatment (Study PR-021)

Study PR-021 was a prospective Phase I/IIa study in 24 adolescent and adult patients with EoE diagnosed by the presence of typical clinical symptoms, histologic evidence of oesophageal mucosal eosinophilia (>24 EOS/HPF) on biopsy samples, and lack of histologic response after previously administered high-dose PPIs. The study was double-blind, randomised, and placebo-controlled. Placebo or study drug (APT-1011) at doses of 1.5 mg BID or 3 mg QD was administered for an 8-week treatment period, to 8 subjects per treatment cohort. Efficacy endpoints included: the modified EEsAI Pathologist Questionnaire as an assessment of treatment response (defined as reduction in tissue eosinophil count to <15 per high power field at the end of therapy 8-week point); change in the modified EEsAI Endoscopy Questionnaire (absent, mild, moderate or severe rating of endoscopic features including fixed rings, strictures, whitish exudates, furrowing, decrease of vascular pattern, and linear shearing); overall oesophagitis symptom severity and other categories indicative of general health, social activity impairment, trouble swallowing and time to eat a meal with food unaltered, based on changes in the modified EEsAI Adult Patient Questionnaire and the Global Eosinophilic Esophagitis Score.

These parameters are all well established and validated tools to measure the efficacy in EoE. All parameters are indicative for the clinical efficacy of the product and represent clinically relevant measurements. The results of the study are presented in Table 13.

at <15 EOS/HPF) was observed in the proximal oesophagus in all 10 assessed subjects treated with APT-1011 (100% of available patient biopsies) and in the distal oesophagus in 11 APT-1011 treated subjects (68.8% of available patient biopsies); the response rate was higher at all oesophageal biopsied sites in the APT-1011 treatment groups relative to placebo. There was no clear difference in treatment response between cohorts receiving divided dose (1.5 mg BID) compared to single daily dose (3 mg QD). Complete response (defined as 0 EOS/HPF) was five-fold higher among subjects who received APT-1011 rather than placebo (62.5% vs. 12.5% complete responders in APT-1011 and placebo groups, respectively).

Improvement in the endoscopy questions from the modified EEsAI Physician Questionnaire was found in 10 subjects (62.5%) treated with APT-1011, but not in any subject treated with placebo (Table 13). Two subjects (one each on placebo and APT-1011 1.5 mg BID) worsened at Week 8. Of additional interest, strictures found at screening were followed in 5 subjects: 3 subjects on active APT-1011 treatment showed resolution of strictures or remained unchanged, compared to two strictures in the placebo cohort which worsened during the study. Decreased vascularity (indicating oedema), furrowing, and white exudates were the most common endoscopic findings at baseline. Improvement in vascularity (normalization) and furrowing were more frequent among subjects receiving APT-1011 relative to placebo suggesting an anti-inflammatory effect of APT-1011.

Greater mean overall improvement in oesophagitis symptomatology (assessed by modified EEsAI Adult Patient Questionnaire) was reported at Week 8/End of Treatment for the past week by subjects in the APT-1011 treatment group than in the placebo treatment group with a numerical trend for greater improvement in dysphagia symptoms for the BID regimen arm compared to the QD regimen arm: 87.5% of subjects in the BID regimen arm had no trouble swallowing in the week prior to the Week 8/EOT assessment compared to 37.5% in the QD regimen arm. Relative to Baseline, mean

TABLE 13

Efficacy results in study PR-021 (week 8; end of treatment)

| Efficacy Endpoint (ITT population) | Placebo N = 8 | APT-1011 1.5 mg BID N = 8 | APT-1011 3 mg QD N = 8 | All APT-1011 N = 16 |
|---|---|---|---|---|
| Subjects with Peak Eos <15 per HPF, n (%) | 1 (12.5) | 6 (75.0) | 5 (62.5) | 11 (68.7) |
| Subjects with zero Eos per HPF, n (%) | 1 (12.5) | 6 (75.0) | 4 (50.0) | 10 (62.5) |
| Subjects with at least 30% decrease in severity of EoE as based on Question 2.2[1] (, n (%) | 3 (37.5) | 6 (75.0) | 6 (75.0) | 12 (75.0) |
| Subjects with at least 30% decrease in severity of EoE as based on EEsAI, Adult Patient Questionnaire, n (%) | 4 (50.0) | 5 (63.0) | 5 (63.0) | 10 (63.0) |
| Subjects with no trouble swallowing in the prior week, n (%) | 1 (12.5) | 7 (87.5) | 3 (37.5) | 10 (62.5) |
| Subjects with improved Endoscopic EoE Activity, n (%) | 0 | 5 (62.5) | 5 (62.5) | 10 (62.5) |
| Change from baseline Gastrointestinal Symptom Rating Scale (GSRS) Average Score, mean (SD) | −0.38 (0.645) | −0.13 (0.479) | −0.30 (0.523) | −0.21 (0.492) |
| Change from baseline Mayo Dysphagia Questionnaire (MDQ-30), mean (SD) | −6.3 (14.33) | −6.3 (21.00) | −7.5 (14.64) | −6.9 (17.50) |
| Subjects with improved Physician Global Assessment (PGA), n (%) | 7 (87.5) | 6 (75) | 7 (87.5) | 13 (81.3) |

Abbreviations:
EoE = eosinophilic oesophagitis,
EEsAI = Eosinophilic Esophagitis Activity Index,
HPF = high-power field,
ITT = Intention-to-Treat
[1]Question 2.2: In the past 7 days please think of all your symptoms due to eosinophilic esophagitis and make an over-all statement by selecting one of the numbers (scale from 0 [no symptoms] to 10[most severe symptoms])

A treatment response based on the peak eosinophil count/HPF (the highest eosinophil count from any biopsy that was scores for subjects in the combined APT-1011 treatment groups decreased with clinical significance, from 4.40 to 1.67 (49.8% decrease), versus from 5.00 to 3.63 (23.2% decrease) in the placebo treatment group. Subjects in each APT-1011 treatment group also had greater mean improvement in baseline symptoms of oesophagitis at Week 4 than subjects in the placebo treatment group. The study was too small to evaluate any potential impact on food impaction.

Other efficacy endpoints, i.e. change in scores on the Gastrointestinal Symptom Rating Scale Questionnaire, the Mayo Dysphagia Questionnaire-30, and the modified EEsAI Physician Global Assessment, showed little change between study groups.

In this study, APT-1011 demonstrated improvements in histology, overall symptoms and overall endoscopic activity supporting further development in EoE.

Follow-Up after Discontinuation of Treatment (Study PR-022)

Of the subjects who completed PR-021, 14 subjects (58%) enrolled into the extension study (Study PR-022). Response or relapse based on dysphagia score could only be assessed for 4 placebo and 7 active subjects. Of these 11 subjects, two patients at Week 4 and no patient after Week 8 were assessed by the investigator as ongoing responders to previous treatment with APT-1011 (Table 14). Based on the investigator's independent assessment, two patients at Week 8 and no patient after Week 12 were assessed as an ongoing responder to treatment with APT-1011.

TABLE 14

Clinical Response/relapse in study PR-022 based on dysphagia scores

| | | Treatment Received During PR-021 | | |
| | | | APT-1011 | |
| Week Clinical Response/Relapse, n (%) | Placebo N = 4 | 1.5 mg BID N = 4 | 3 mg QD N = 3 | All N = 7 |
|---|---|---|---|---|
| Baseline Responder | 2 (50.0) | 2 (50.0) | 2 (66.7) | 4 (57.1) |
| Week 4 Continued to be a Responder | 1 (25.0) | 0 | 2 (66.7) | 2 (28.6) |
| Week 8 Continued to be a Responder | 1 (25.0) | 0 | 0 | 0 |
| Week 12 and Week 16 Continued to be a Responder | 1 (25.0) | 0 | 0 | 0 |

At Week 24/Final Evaluation, all 14 subjects (4 randomised to placebo, and 5 each randomised to APT-1011 at 1.5 mg BID or 3.0 mg QD in PR-021) had relapsed. Most subjects that were on APT-1011 during PR-021 and entered the PR-022 study, relapsed by Week 4 (80%) in PR-022 with all relapsing by Week 8; whereas those who were on placebo in PR-021 who entered the PR-022 study relapsed later, with one of these placebo responder continuing to be a Responder until Week 20.

All subjects started rescue therapy during the extension study. All subjects had administered at least 1 form of rescue therapy during the study to treat relapsing EoE symptoms and/or histological relapse. Of the 14 subjects who participated in this study, 13 had administered concomitant rescue medication. The most frequently administered concomitant rescue medication was swallowed fluticasone propionate for inhalation.

As the efficacy of APT-1011 did not appear maximal at 8 weeks given continuing improvement between 4 and 8 weeks, a potential benefit of longer treatment (12 weeks) was explored in future clinical studies.

Example 3. Improved Safety Profile Over Longer Treatment Period Compared to FP Suspension and Jorveza®

Relapse of successful corticosteroid therapy is not uncommon and was observed 8 to 9 weeks after completion of fluticasone propionate (FP) therapy indicating that prolonged treatment may be necessary. This was recently confirmed by a long-term study demonstrating that swallowed FP (in a metered dose inhaler, "MDI") is effective as a long-term maintenance therapy for children with EoE, without growth impediment or serious side effects. However, with long term FP use, the incidence of candidiasis increases. For example, oesophageal candidiasis rates of 5% to 31% were reported in short-term/induction studies and rates of 5 to 6% were reported in long-term/maintenance studies.

Applicant conducted a large randomized, double-blind, placebo-controlled study Phase IIb study in an EoE patient population previously found to be acceptable by the CHMP. Applicant found that APT-1011 was superior to placebo in the treatment of EoE by demonstrating statistically significant and clinically relevant improvements in both primary and most secondary efficacy variables over a 12-week period with a well-tolerated safety profile. Based on the totality of the data, 3 mg HS was identified and selected as the dose with the most favorable benefit-risk ratio. A low rate of candidiasis infections was reported with this dosing regimen. Notably, the rate of candidiasis infections with the FP ODT is substantially lower than the candidiasis rate reported with Jorveza®.

Currently, only Jorveza® is authorized for the treatment of EoE. Applicant's FP ODT as described herein represents a significant benefit in terms of improved safety due to a lower rate of candidiasis infections observed with APT-1011 when compared with the approved treatment option.

Oral, oropharyngeal, and oesophageal candidiasis infections are known side effects of swallowed budesonide and FP used for the treatment of EoE. As described in the Jorveza® summary of product characteristic (SmPC), fungal infections in the mouth, pharynx and the oesophagus were the most frequently observed adverse reactions in the clinical studies with Jorveza (Jorveza SmPC 2019). In the pivotal study, 11.5% patients experienced cases of suspected fungal infections associated with clinical symptoms and the total rate of infections including those diagnosed by endoscopy and histology without symptoms was 31%. Although, most cases were of mild severity, they required treatment with local and systemic antimycotic medication during the trial (Jorveza® European assessment report [EPAR] 2017). It is further stated in the EPAR that the concern of the high rate of oesophageal infections (>20%) may be less strong in a setting where treatment is stopped after the course of 6 or 12 weeks treatment, however it may be more relevant once the need for ongoing treatment (maintenance) is defined. According to the SmPC, treatment with Jorveza is limited to 6 to 12 weeks; the dosing schedule is twice daily: morning and evening (Jorveza SmPC 2019).

In the completed Part 1 of study SP-1011-002 (induction therapy, Day 1 to Week 14) oral candidiasis was only reported in 1 of 21 subjects (4.8%) for the dose group APT-1011 3 mg HS, which is the dose with the most favorable benefit-risk ratio. There were no cases of oesophageal or oropharyngeal candidiasis in this dose group (Table 10, See Example 1). No cases of candidiasis were observed in the dose group of APT-1011 1.5 mg HS and in the placebo arm. Higher rates were reported in the BID dosing groups, APT-1011 1.5 mg BID (oesophageal candidiasis and oral candidiasis, 2/23 (8.7%) each), and APT-1011 3 mg BID (oesophageal candidiasis, 5/20 (25%); oral candidiasis, 2/20 (10%); and oropharyngeal candidiasis, 1/20 (5.0%)). These data indicate that the once daily HS dosing regimen is associated with a lower risk of candidiasis infections.

Part 2 (maintenance therapy) of study SP-1011-002 evaluating safety and efficacy of APT-1011 over an additional 38-week period (Week 14 to 52) is currently ongoing. This study confirmed the low rates of candidiasis in this maintenance part and established the superiority of APT-1011 over Jorveza based on a lower rate of candidiasis. Although most cases of candidiasis cases were of mild severity with Jorveza® treatment, they required treatment with additional local and systemic antimycotic medication. This is of special concern when treatment with local-acting corticosteroids over a long period is required to alleviate the symptoms of EoE. This is likely to be the case as relapse after successful treatment of EoE is common. Chronic or recurrent treatment of EoE is likely to be required, and recurrent candidiasis could therefore necessitate repeated antimycotic treatment. Antimycotic treatments such as fluconazole, which is used to treat corticosteroid-induced candidiasis in EoE patients, have a high interaction potential as it is a potent inhibitor of cytochrome (CYP) isoenzyme $2C_9$ and a moderate inhibitor of CYP3A4 with a risk of increasing plasma levels of an array of other medicinal products. A reduction of the need for antimycotic treatment is therefore a significant benefit for the patient.

As EoE is a chronic disease and relapse after successful induction therapy is common, the ongoing Part 2 of the Phase IIb provided the necessary confirmation of the maintenance of efficacy and long-term safety of APT-1011.

The invention claimed is:

1. A method of treating eosinophilic esophagitis (EoE) in a patient in need thereof comprising administering to the patient an orally disintegrating tablet (ODT) comprising about 1.5 mg to about 3 mg of fluticasone propionate, wherein the ODT is orally administered once daily for at least 12 weeks, wherein at Week 12:
  a. the patient's risk of candidiasis is less than about 10%, and
  b. the patient shows an improvement in at least one of the following outcomes compared to a patient that is administered the fluticasone propionate twice daily:
    i. at least one symptom score measured using a patient reported outcome symptom evaluation (PROSE) instrument after an episode of dysphagia;

ii. EoE Endoscopic Reference (EREFS) score;
    iii. EoE Activity Index (EEsAI) avoidance, modification, and slow swallowing (AMS) score;
    iv. Global EoE score;
    v. Patient global impression of severity (PGIS); and
    vi. Patient global impression of change (PGIC).

2. The method of claim 1, wherein fluticasone propionate is administered at bedtime or at nighttime.

3. The method of claim 1, wherein the patient's risk of candidiasis about 5% or less.

4. The method of claim 1, wherein the candidiasis is oral candidiasis or esophageal candidiasis.

5. The method of claim 1, wherein the candidiasis is oral candidiasis.

6. The method of claim 5, wherein the patient's risk of oral candidiasis is less than about 4%, less than about 3%, less than about 2%, or less than about 1%.

7. The method of claim 1, wherein the candidiasis is esophageal candidiasis.

8. The method of claim 7, wherein the patient's risk of esophageal candidiasis is about 4.8%.

9. The method of claim 1, wherein the symptom score comprises:
  (i) on a scale ranging from 0 to 10, a difficulty getting food down;
  (ii) on a scale ranging from 0 to 10, a worst discomfort with food;
  (iii) on a scale ranging from 0 to 10, a worst pain with food;
  (iv) a mean score of any combination of (i), (ii), and (iii);
  (v) a number of dysphagia episodes;
  (vi) a daily rate of dysphagia episodes; or
  (vii) a number of dysphagia-free days.

10. The method of claim 9, wherein the symptom score is:
  (a) a daily mean of (i), (ii), and (iii) over a 14 day period;
  (b) a mean score of (i), (ii), and (iii) for the worst episode per day of dysphagia over a 14 day period;
  (c) a score for the worst symptom of dysphagia over a 14 day period;
  (d) a number of dysphagia episodes;
  (e) a daily rate of dysphagia episodes; or
  (f) a number of dysphagia-free days.

11. The method of claim 1, wherein at least one symptom score is improved by 0.5 to 4 points.

12. The method of claim 1, wherein the symptom score, the mean score, the worst episode score, or the worst symptom score is determined using data from 2 weeks of entries immediately prior to Week 12 and Week 26.

13. The method of claim 1, wherein the EREFS score is improved by about 0.3 to 1.5 points.

14. The method of claim 1, wherein the Global EoE score is improved by about 1 to 4 points.

15. The method of claim 1, wherein the PGIS score shifts to improvement by about 1 to 5 severity categories.

16. The method of claim 1, wherein the EEsAI score is improved by about 2 to 15 points.

17. The method of claim 1, wherein the patient further shows improvement in Eosinophilic Esophagitis Quality of Life Questionnaire (EoO-QoL-A).

18. The method of claim 17, wherein the EoO-QoL-A score is improved by about 1 to 3 points.

19. The method of claim 1, wherein the eosinophil count in the patient's esophagus is reduced compared to the patient's baseline eosinophil level.

20. The method of claim 19, wherein the eosinophil count is reduced to no more than 6 eosinophils per high power field (hpf).

21. The method of claim 20, wherein the eosinophil count is measured in the distal portion of the esophagus, the proximal portion of the esophagus, or both.

22. The method of claim 21, wherein eosinophil count in the distal portion of the esophagus is no more than 6 eosinophils per hpf.

23. The method of claim 21, wherein eosinophil count in the proximal portion of the esophagus is no more than 6 eosinophils per hpf.

24. The method of claim 1, wherein the number of dysphagia episodes is decreased compared to a patient that is administered the fluticasone propionate twice daily.

25. The method of claim 1, the number of dysphagia-free days is increased compared to a patient that is administered the fluticasone propionate twice daily.

26. The method of claim 1, wherein (a) and (b) are measured at week 12.

27. The method of claim 1, wherein (a) and (b) are measured again at week 26 and/or week 52.

28. The method of claim 1, wherein the patient shows an improvement in at least one of the following outcomes compared to a patient that is administered the fluticasone propionate twice daily:

i. at least one symptom score measured using a patient reported outcome symptom evaluation (PROSE) instrument after an episode of dysphagia;

ii. EoE Endoscopic Reference (EREFS) score; or iii. Global EoE score.

29. The method of claim 1, wherein the symptom score is the number of dysphagia episodes over 14 days.

30. The method of claim 1, wherein the symptom score is one or more of:

i. number of dysphagia free days over a 14 day period;

ii. the average daily episode severity score over a 14 day period;

iii. symptom burden over a 14 day period.

31. The method of claim 1, wherein the patient shows an improvement in the visual dysphagia question (VDQ) composite score compared to a patient that is administered the fluticasone propionate twice daily.

32. The method of claim 1, wherein the patient shows an improvement in the EEsAI total score compared to a patient that is administered the fluticasone propionate twice daily.

\* \* \* \* \*